(12) United States Patent
Abbott et al.

(10) Patent No.: US 10,996,146 B2
(45) Date of Patent: May 4, 2021

(54) DEVICES FOR DISSOCIATING A BIOLOGICAL TISSUE SAMPLE AND METHODS OF USE THEREOF

(71) Applicant: BECTON, DICKINSON AND COMPANY, Franklin Lakes, CA (US)

(72) Inventors: Richard Abbott, Raleigh, NC (US); Alexander G. Lastovich, Raleigh, NC (US); Friedrich G. Hahn, Durham, NC (US); Jacob Jones, Durham, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 347 days.

(21) Appl. No.: 15/978,026

(22) Filed: May 11, 2018

(65) Prior Publication Data

US 2018/0348097 A1    Dec. 6, 2018

Related U.S. Application Data

(60) Provisional application No. 62/513,907, filed on Jun. 1, 2017.

(51) Int. Cl.
*G01N 1/28* (2006.01)
*B02C 18/02* (2006.01)
*C12M 1/33* (2006.01)

(52) U.S. Cl.
CPC ............. *G01N 1/286* (2013.01); *B02C 18/02* (2013.01); *C12M 45/02* (2013.01); *G01N 2001/2866* (2013.01); *G01N 2001/2873* (2013.01)

(58) Field of Classification Search
CPC ........... G01N 1/286; G01N 2001/2866; G01N 2001/2873; B02C 18/02; C12M 45/02
See application file for complete search history.

(56) References Cited

U.S. PATENT DOCUMENTS

| | | | |
|---|---|---|---|
| 3,028,314 A | 4/1962 | Means et al. |
| 3,298,411 A | 1/1967 | Theodore |
| 3,666,187 A | 5/1972 | Norris |
| 3,938,784 A | 2/1976 | Moreton |
| 4,828,395 A | 5/1989 | Saito et al. |

(Continued)

FOREIGN PATENT DOCUMENTS

| | | |
|---|---|---|
| KR | 10-2013-0045465 A | 5/2013 |
| WO | WO2005030936 A1 | 4/2005 |
| WO | WO2016036464 A1 | 3/2016 |

OTHER PUBLICATIONS

Burden, David W. "Guide to the Homogenization of Biological Samples", Random Primers, Issue No. 7, Sep. 2008, pp. 1-14.

(Continued)

*Primary Examiner* — Omar Flores Sanchez
(74) *Attorney, Agent, or Firm* — Bret E. Field; Bozicevic, Field & Francis LLP

(57) ABSTRACT

Tissue dissociators configured to disrupt a biological tissue sample are provided. Aspects of the tissue dissociators according to certain embodiments include a blade holder having a blade and a sample holder that includes a tissue actuator having a distal end pliable stopper where the tissue actuator is configured to be displaced along a longitudinal axis with the sample holder. Also provided are methods of dissociating a biological tissue sample with the tissue dissociators, as well as kits including the tissue dissociators.

19 Claims, 21 Drawing Sheets

(56) References Cited

U.S. PATENT DOCUMENTS

| | | | |
|---|---|---|---|
| 5,035,708 | A | 7/1991 | Alchas et al. |
| 5,330,914 | A | 7/1994 | Uhlen et al. |
| 5,372,945 | A | 12/1994 | Alchas et al. |
| 5,409,833 | A | 4/1995 | Hu et al. |
| 5,610,074 | A | 3/1997 | Beritashvili et al. |
| 5,731,199 | A | 3/1998 | Roggero |
| 5,786,207 | A | 7/1998 | Katz et al. |
| 9,458,190 | B2 * | 10/2016 | Lazarev ............. B01D 11/0288 |
| 9,663,760 | B2 * | 5/2017 | Taghizadeh ............. B02C 18/30 |
| 10,518,267 | B2 * | 12/2019 | Hjelseth ................. C12M 45/06 |
| 2004/0018575 | A1 | 1/2004 | Rappin et al. |
| 2004/0043701 | A1 | 3/2004 | Garland |
| 2004/0158226 | A1 | 8/2004 | Soo Hoo et al. |
| 2005/0139704 | A1 | 6/2005 | Liao et al. |
| 2007/0148756 | A1 | 6/2007 | Bullen et al. |
| 2007/0156129 | A1 | 7/2007 | Kovalcheck |
| 2007/0166834 | A1 | 7/2007 | Williamson |
| 2008/0253935 | A1 * | 10/2008 | Kane ....................... G01F 11/18 422/400 |
| 2009/0084202 | A1 | 4/2009 | Mimori |
| 2009/0136384 | A1 * | 5/2009 | Bucher ................ B01F 7/1695 422/400 |
| 2009/0155878 | A1 * | 6/2009 | Becker ................... G01N 1/286 435/173.9 |
| 2012/0052559 | A1 | 3/2012 | Haraguchi et al. |
| 2012/0201726 | A1 | 8/2012 | Pearcy et al. |
| 2013/0028813 | A1 | 1/2013 | Shioyama et al. |
| 2016/0024450 | A1 | 1/2016 | Quick et al. |
| 2016/0069781 | A1 | 3/2016 | Middlebrook et al. |
| 2017/0145369 | A1 | 5/2017 | Poggel et al. |
| 2018/0043352 | A1 * | 2/2018 | Saul .................... C12N 15/1003 |
| 2018/0231438 | A1 * | 8/2018 | Mi ......................... G01N 1/06 |
| 2019/0212233 | A1 * | 7/2019 | Jovanovich ............ G01N 35/00 |

OTHER PUBLICATIONS

Cunningham, Robert E. "Chapter 27: Tissue Disaggregation", Immunocytochemical Methods and Protocols, Methods in Molecular Biology, vol. 34, 1994, pp. 225-228.

Cunningham, Robert E. "Chapter 32: Tissue Disaggregation", Immunocytochemical Methods and Protocols Methods in Molecular Biology, vol. 588, 2010, pp. 327-330.

Invitrogen Corporation, "Tissue Homogenization Procedures for use with ELISA", Product Sheet, 2008, pp. 1-8.

Smeets et al. "Comparison of Tissue Disaggregation Techniques of Transitional Cell Bladder Carcinomas for Flow Cytometry and Chromosomal Analysis", Cytometry 8, 1987, pp. 14-19.

Notification of the First Office Action for Chinese patent application serial No. 201580045929.9, dated Jul. 27, 2018, 4 pages.

* cited by examiner

DEVICES FOR DISSOCIATING A BIOLOGICAL TISSUE SAMPLE AND METHODS OF USE THEREOF

CROSS-REFERENCE TO RELATED APPLICATION

Pursuant to 35 U.S.C. § 119(e), this application claims priority to the filing date of U.S. Provisional Patent Application Ser. No. 62/513,907 filed Jun. 1, 2017; the disclosure of which application is incorporated herein by reference.

INTRODUCTION

Processing a biological tissue sample to achieve cell compositions is often necessary in numerous therapeutic, diagnostic and research applications. To separate a cell from its attachment to other cells and extracellular matrix, tissue structure is generally dissociated by mechanical disruption and enzymatic digestion. Mechanical disruption can include mincing and chopping with scissors or a scalpel or with a handheld or benchtop motorized tissue processor with the aim of preparing tissue samples of smaller dimensions. Tissue dissociation is often laborious requiring numerous manipulations of the tissue. The large number of processing steps to separate the desired tissue sample from other biological material can result in over-processing and reduce the viability of the cells. Likewise, the time required to process certain sample types (e.g., healthy tissues) may require a different extent of dissociation than others (e.g., cancerous or necrotic tissue), making dissociation of complex biological samples difficult and inefficient.

SUMMARY

Aspects of the present disclosure include tissue dissociators configured to disrupt a biological tissue sample. Tissue dissociators according to certain embodiments include a blade holder having a blade and a sample holder having a tissue actuator that includes a distal end pliable stopper where the tissue actuator is configured to be displaced along a longitudinal axis within the sample holder. The pliable stopper is, in some embodiments, positioned to be cut by at least one of the blades of the blade holder when the tissue actuator is displaced to the distal end of the sample holder. In other embodiments, the pliable stopper is positioned at the distal end of the tissue actuator and is configured to be pressed through the blades of the blade holder. In certain instances, when the pliable stopper is pressed through the blades, the pliable stopper contacts the side edges of the blades. In these instances, the pliable stopper is configured to remove tissue remaining on the blades during dissociation of the biological tissue sample.

In embodiments, the blade holder includes a mount having an orifice and one or more cutting blades extending across the mount orifice and a cap having an orifice and one or more cutting blades extending across the cap orifice. In certain instances, the pliable stopper is configured to be pressed through the cap cutting blades. In other instances, the pliable stopper is configured to be pressed through the cap cutting blades and the mount cutting blades. The mount may be coupled to the cap, such as with one or more aligners. The aligners are configured to position the mount cutting blades and the cap cutting blades at an angle to each other, such as at an angle of from 1° to 90°. In certain embodiments, the mount cutting blades and the cap cutting blades are positioned orthogonal to the mount cutting blades. The cutting blades may be coupled to the mount and the cap with one or more fasteners. In certain instances, the cutting blades are co-molded to the mount and the cap. In some instances, the distal end of sample holder is coupled to the proximal end of the cap. In other embodiments, the sample holder is co-molded to the cap. In yet other embodiments, the sample holder and cap form a single integrated sample holder having one or more blades. The tissue dissociator is, in certain embodiments, configured to be coupled to a container. In some instances, the container is fastened to the blade holder with one or more fasteners. In other instances, the container is fastened to the sample holder with one or more fasteners. In these embodiments, tissue dissociators of interest include a container, a blade holder releasably coupled to the container and a sample holder having a tissue actuator with a distal end pliable stopper.

In some embodiments, the tissue actuator and the sample holder include aligners which provide audible or tactile feedback to indicate that the tissue actuator has been displaced a predetermined distance within the sample holder. In certain embodiments, the tissue actuator includes one or more protrusions for providing audible or tactile feedback. In certain instances, the tissue actuator includes one or more aligners. In some instances, the tissue actuator includes one or more indicators (e.g., protrusions, markings, notches, indentations, etc.) which provide feedback, such as visual, audible or tactile feedback, that indicates that the tissue actuator has been displaced to the distal end of the sample holder. In one example, the tissue actuator includes an indicator (e.g., a marking, indentation, protrusion, etc.) that provides visual feedback that the tissue actuator has been displaced to the distal end of the sample holder. In other instances, the tissue actuator includes one or more protrusions or indentations which provide audible or tactile feedback which indicates that the cutting motion is complete and the tissue has been dissociated.

Aspects of the disclosure also include methods for dissociating a biological tissue sample. Methods according to certain embodiments include positioning a biological tissue into the sample holder of the tissue dissociator, pressing the biological tissue against the cutting blades by displacing the tissue actuator to the distal end of the sample holder in a manner sufficient to dissociate the biological tissue. In embodiments, the pliable stopper positioned at the distal end of the tissue actuator is pressed through the cutting blades. In some embodiments, pressing the pliable stopper through the cutting blades is sufficient to cut the pliable stopper. In other embodiments, pressing the pliable stopper through the cutting blades displaces the pliable stopper through while contacting the inner walls of the cutting blades. To dissociate tissue, the tissue actuator may be displaced continuously or in discrete increments along the longitudinal axis of the sample holder to press the tissue through the cutting blades. In some instances, the tissue actuator is displaced so that the pliable stopper contacts the inner walls of the cutting blades and removes any residual tissue from the cutting blades.

Kits which include a sample holder and a tissue actuator with a pliable stopper at the distal end are also provided. In some embodiments, kits further include a blade holder, such as a mount having one or more cutting blades and a cap having one or more cutting blades. In certain instances, kits further include one or more tissue biopsy utensils, such as tweezers, needles, scalpels and scissors. In other instances, kits further include digestive enzyme and buffer solutions.

Kits may also include one or more labelling reagents, such as reagents for preparing a flow cytometry sample.

BRIEF DESCRIPTION OF THE FIGURES

The invention may be best understood from the following detailed description when read in conjunction with the accompanying drawings. Included in the drawings are the following figures.

DETAILED DESCRIPTION

Figure 1:
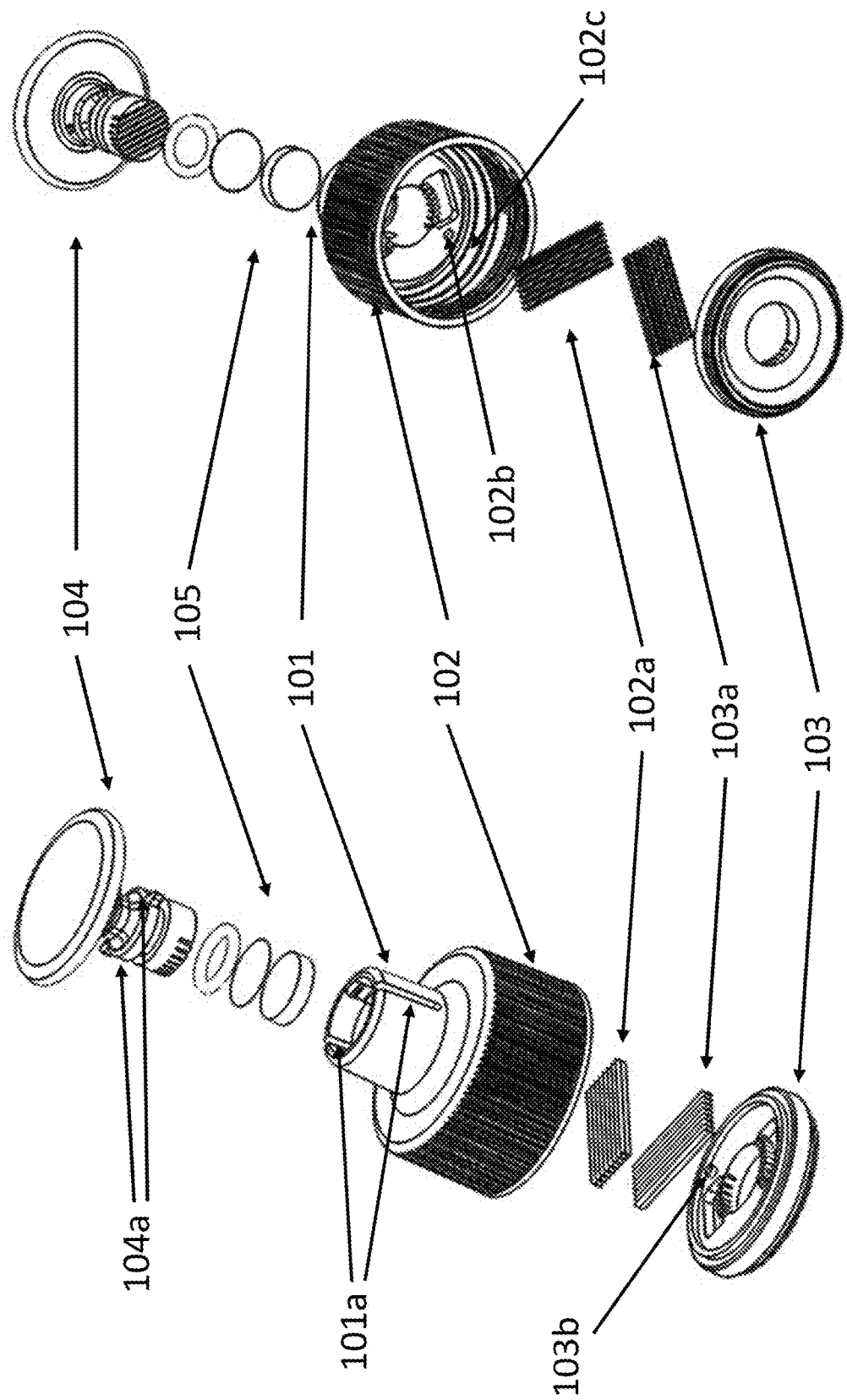
FIG. 1 depicts a tissue dissociator according to certain embodiments of the present disclosure.

Tissue dissociators configured to disrupt a biological tissue sample are provided. Aspects of the tissue dissociators according to certain embodiments include a blade holder having a blade and a sample holder that includes a tissue actuator having a distal end pliable stopper where the tissue actuator is configured to be displaced along a longitudinal axis with the sample holder. Also provided are methods of dissociating a biological tissue sample with the tissue dissociators, as well as kits including the tissue dissociators.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the present disclosure provides a tissue dissociator configured to disrupt a biological tissue sample. In further describing embodiments of the disclosure, tissue dissociators that include a blade holder and a sample holder that includes a tissue actuator having a distal end pliable stopper are first described in greater detail. Next, methods for preparing a dissociated biological tissue sample with the subject tissue dissociators are described. Kits for preparing a dissociated biological tissue sample are also provided.

Devices for Dissociating a Biological Tissue Sample

As summarized above, aspects of the present disclosure include a tissue dissociator configured to dissociate a biological tissue sample. The term "dissociate" is used herein in its conventional sense to refer to breaking up and separating the biological tissue sample into a plurality of smaller tissue fragments, such as into 2 or more tissue fragments, such as 5 or more, such as 10 or more, such as 25 or more, such as 50 or more, such as 100 or more, such as 250 or more, such as 500 or more, such as 1000 or more, such as 5000 or more and including breaking up and separating a biological tissue sample into 10,000 or more tissue fragments. In embodiments, a given biological tissue sample is considered dissociated, if following dissociation, 2 or more, such as 5 or more, such as 10 or more, such as 25 or more, such as 50 or more, such as 100 or more tissue fragments which were originally stably associated with each other are no longer stably associated with other, i.e., they can be freely moved relative to each other. In certain embodiments, methods include breaking up an organ or tissue in order to collect the smaller components which collectively make up the organ or tissue.

In embodiments, the subject tissue dissociators are configured to dissociate a biological tissue sample in a manner sufficient to facilitate the preparation of a single cell composition from the dissociated tissue fragments. The phrase "single cell" is used herein in its conventional sense to refer to a composition having distinct and separated cells of the tissue that is dissociated. In certain embodiments, the tissue dissociator is configured to prepare tissue fragments that are suitable for further treatment (e.g., with a digestive enzyme) to prepare a single cell composition (e.g., suspension) of the target tissue sample. For example, the subject tissue dissociator may be configured to dissociate the biological tissue sample to produce tissue fragments having substantially increased surface area as compared to the undissociated tissue such that the tissue fragments are suitable for treatment to produce a single cell composition of the tissue sample. In other instances, the tissue dissociator produces tissue fragments having a total cumulative surface area that is 2-fold greater than the undissociated tissue sample, such as 5-fold or greater, such as 10-fold or greater, such as 25-fold or greater, such as 50-fold or greater, such as 100-fold or greater, such as 1000-fold or greater, such as 5000-fold or greater, such as 10,000-folder or greater, such as 100,000-fold or greater and including tissue fragments having a total cumulative surface area that is 1,000,000-fold greater than the undissociated tissue sample. In these embodiments, the produced tissue fragments are suitable for treatment to produce a single cell composition from the tissue fragments.

In embodiments, the subject tissue dissociators are configured to dissociate a tissue sample such that the dissociated tissue fragments have a cell viability of 50% or greater, such as 60% or greater, such as 70% or greater, such as 75% or greater, such as 80% or greater, such as 85% or greater, such as 90% or greater, such as 95% or greater, such as 97% or greater, such as 99% or greater and including tissue fragments having a cell viability of 99.9% or greater. The term "cell viability" is used herein in its conventional sense to refer to the percentage of cells that remain viable in the tissue sample after being dissociated into fragments with the tissue dissociator. In certain embodiments, the subject tissue dissociators are configured to provide tissue fragments that retain 100% of the viable cells of the tissue sample. Any convenient protocol may be used to determine the percent cell viability of the sample, including by not limited to a cell analyzer (e.g., ViCell cell analyzer) or flow cytometry. In some embodiments, the subject tissue dissociators are configured to dissociate a tissue sample such that the dissociated tissue fragments have a cell viability of 50% or greater as determined by a cell analyzer, such as 60% or greater, such as 70% or greater, such as 75% or greater, such as 80% or greater, such as 85% or greater, such as 90% or greater, such as 95% or greater, such as 97% or greater, such as 99% or greater and including tissue fragments having a cell viability of 99.9% or greater as determined by a cell analyzer. In other embodiments, the subject tissue dissociators are configured to dissociate a tissue sample such that the dissociated tissue fragments have a cell viability of 50% or greater as determined by flow cytometry, such as 60% or greater, such as 70% or greater, such as 75% or greater, such as 80% or greater, such as 85% or greater, such as 90% or greater, such as 95% or greater, such as 97% or greater, such as 99% or greater and including tissue fragments having a cell viability of 99.9% or greater as determined by flow cytometry.

As used herein, the term "biological tissue sample" is used in its conventional sense to refer to a whole organism, plant, fungi or a subset of tissues or component parts of the organism. Biological tissue samples may be obtained from an in vitro source (e.g., tissue grown in laboratory culture) or from an in vivo source (e.g., a mammalian subject, a human subject, etc.). In some embodiments, the tissue sample is obtained from an in vitro source. In some embodiments, the biological tissue sample is obtained from an in vivo source, where in some instances, tissues derived from a subject are cultured, stored, or manipulated prior to evaluation. In vivo sources include living multi-cellular organisms and can yield non-diagnostic or diagnostic tissue samples.

In certain embodiments the source of the tissue sample is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. Biological tissue samples may include tissue from human subjects of both genders and at any stage of development (i.e., neonates, infant, juvenile, adolescent, adult), where in certain embodiments the human subject is a juvenile, adolescent or adult. While the present disclosure may be applied to samples from a human subject, it is to be understood that the methods may also be carried out on samples from other animal subjects (that is, in "non-human subjects") such as, but not limited to, birds, mice, rats, dogs, cats, livestock and horses.

In some embodiments, biological tissue samples include tissue from a component part of a human subject, such as organs, including but not limited to integumentary tissue (e.g. sections of the skin), oral tissue (e.g., buccal, tongue, palatal, gums), respiratory tissue (e.g., pharynx, larynx, trachea, bronchi, lungs, diaphragm) gastrointestinal tissue (e.g., esophagus, stomach, liver, gallbladder, pancreas, intestines, colon, rectum and anus), cardiovascular tissue (e.g., heart, blood vessels), endocrine tissue (e.g., hypothalamus, pituitary gland, pineal body or pineal gland, thyroid, parathyroids, adrenal glands) and genitourinary tissue (kidneys, ureters, bladder, urethra, ovaries, fallopian tubes, uterus, vagina, mammary glands, testes, vas deferens, seminal vesicles, prostate, penis), muscular tissue, nervous tissue (e.g., brain, spinal cord, nerves) as well as soft skeletal tissue (cartilage, ligaments, tendons). Biological samples may be any type of organismic tissue, including both healthy and diseased tissue (e.g., cancerous, malignant, necrotic, etc.)

The subject tissue dissociator devices are configured to dissociate biological tissue samples of any size, depending on the type of tissue and size of the sample holder where in some instances the length of biological tissue samples dissociated with the subject tissue dissociators may range from 0.01 cm to 5 cm, such as from 0.02 cm to 4.5 cm, such as from 0.03 cm to 4 cm, such as from 0.04 cm to 3.5 cm, such as from 0.05 cm to 3 cm, such as from 0.06 cm to 2.5 cm, such as from 0.07 cm to 2 cm, such as from 0.08 cm to 1.5 cm, such as from 0.09 cm to 1 cm and including from 0.1 cm to 0.5 cm. The width of the biological sample may range from 0.01 cm to 5 cm, such as from 0.02 cm to 4.5 cm, such as from 0.03 cm to 4 cm, such as from 0.04 cm to 3.5 cm, such as from 0.05 cm to 3 cm, such as from 0.06 cm to 2.5 cm, such as from 0.07 cm to 2 cm, such as from 0.08 cm to 1.5 cm, such as from 0.09 cm to 1 cm and including from 0.1 cm to 0.5 cm. The thickness of biological tissue samples may also vary, ranging from 0.001 mm to 50 mm, such as from 0.002 mm to 25 mm, such as from 0.003 mm to 22.5 mm, such as from 0.004 mm to 20 mm, such as from 0.005 mm to 15 mm, such as from 0.005 mm to 12.5 mm and including from 0.01 mm to 10 mm. such as from 0.05 mm to 10 mm and including from 0.1 mm to 5 mm. For example, tissue dissociator devices of interest may be configured to dissociate biological tissue samples having a surface area ranging from 0.001 to 100 $cm^2$, such as from 0.05 to 100 $cm^2$, 0.01 to 100 $cm^2$, such as 0.05 to 50 $cm^2$, such as 0.1 to 25 $cm^2$, such as 0.5 to 15 $cm^2$, such as 0.75 to 10 $cm^2$, such as 1 to 7.5 $cm^2$, and including 2 to 5 $cm^2$. The subject tissue dissociators may be configured to dissociate biological tissue samples having a volume ranging from 0.001 to 10 $cm^3$, such as from 0.005 to 9 $cm^3$, such as from 0.0075 to 8 $cm^3$, such as from 0.01 to 7 $cm^3$, such as 0.02 to 6 $cm^3$, such as 0.05 to 5 $cm^3$, such as 0.1 to 4 $cm^3$, such as 0.5 to 3 $cm^3$, and including 0.75 to 2 $cm^3$.

In certain embodiments, the biological tissue sample is a specimen that has been preloaded into a dissociator sample holder and is stored in the sample holder for a predetermined period of time before the biological tissue sample is dissociated. For example, the biological tissue sample may preloaded into a dissociator sample holder and frozen in a freezer. The amount of time the biological tissue sample is stored before dissociating the biological tissue sample may vary, such as 0.1 hours or more, such as 0.5 hours or more, such as 1 hour or more, such as 2 hours or more, such as 4 hours or more, such as 8 hours or more, such as 16 hours or more, such as 24 hours or more, such as 48 hours or more, such as 72 hours or more, such as 96 hours or more, such as 120 hours or more, such as 144 hours or more, such as 168 hours or more and including preloading the biological tissue sample into the dissociator sample holder 240 hours or more before dissociating the biological tissue sample or may range such as from 0.1 hours to 240 hours before dissociating the biological tissue sample, such as from 0.5 hours to 216 hours, such as from 1 hour to 192 hours and including from 5 hours to 168 hours before disrupting the biological tissue sample. For example, the biological tissue sample may be preloaded into a dissociator sample holder at a remote location (e.g., in a physician's office) and sent to a laboratory for processing in accordance with the subject methods. By "remote location" is meant a location other than the location at which the tissue sample is obtained and preloaded into the container. For example, a remote location could be another location (e.g. office, lab, etc.) in the same city, another location in a different city, another location in a different state, another location in a different country, etc., relative to the location of the tissue dissociator device, e.g., as described in greater detail below. In some instances, two locations are remote from one another if they are separated from each other by a distance of 10 m or more, such as 50 m or more, including 100 m or more, e.g., 500 m or more, 1000 m or more, 10,000 m or more, etc.

As summarized above, tissue dissociators according to certain embodiments include a sample holder having a tissue actuator with a distal end pliable stopper where the tissue actuator is configured to be displaced along a longitudinal axis within the sample holder. The sample holder has a distal end and a proximal end with walls between the distal end and proximal end that together form an inner chamber within the sample holder that is configured to receive one or more biological tissue samples. In some embodiments, the outer walls of the sample holder and inner chamber have the same cross-sectional shape where cross-sectional shapes of interest include, but are not limited to rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. For example, both the outer walls of the sample holder and the inner chamber may have circular or oval cross sections or both the outer walls of the sample holder and the inner chamber may have polygonal (e.g., octagonal) cross sections. In other embodiments, the outer walls of the sample holder and inner chamber within the sample holder have different cross-sectional shapes (e.g., housing having a circular cross-section and inner chamber having a square or polygonal cross-section)

Depending on the amount and type of tissue sample being processed, the size of the inner chamber of the sample holder may vary, where in some instances the length of the inner chamber of the sample holder may range from 0.25 cm to 5 cm, such as from 0.5 cm to 4.5 cm, such as from 1 cm to 4 cm, such as from 1.5 cm to 3 cm and including from 0.5 cm to 3 cm and the width of the inner chamber of the sample holder may range from 0.25 cm to 5 cm, such as from 0.5 cm to 4.5 cm, such as from 1 cm to 4 cm, such as from 1.5 cm to 3.5 cm and including from 1 cm to 3 cm. Where the inner chamber of the sample holder has a cylindrical cross-section, the diameter may vary, in some embodiments, ranging from 0.1 cm to 10 cm, such as from 0.5 cm to 9 cm, such as from 0.75 cm to 8 cm and including from 1 cm to 7 cm. Accordingly, the volume of the inner chamber within the sample holder may vary, ranging from 0.001 to 10 $cm^3$, such as from 0.005 to 9 $cm^3$, such as from 0.0075 to 8 $cm^3$, such as from 0.01 to 7 cm³, such as 0.02 to 6 cm³, such as 0.05 to 5 cm³, such as 0.1 to 4 cm³, such as 0.5 to 3 cm³, and including 0.75 to 2 cm³.

In some embodiments, the sample holder is cylindrical having a proximal portion and a distal portion along a longitudinal axis which terminates in an orifice that is transverse to the longitudinal axis of the sample holder. The length of the cylindrical sample holder (as measured along the longitudinal axis) may vary ranging from 0.25 cm to 5 cm, such as from 0.5 cm to 4.5 cm, such as from 1 cm to 4 cm, such as from 1.5 cm to 3 cm and including from 0.5 cm to 3 cm. In embodiments, the orifice may extend across all or part of the inner chamber at the distal end of the sample holder (as measured from central axis of the sample holder). In some instances, the orifice extends across 10% or more of the inner chamber of the sample holder, such as 15% or more, such as 25% or more, such as 50% or more, such as 75% or more, such as 80% or more, such as 85% or more, such as 90% or more, such as 95% or more, such as 97% or more and including 99% or more. In certain instances, the orifice at the distal end extends across the entire (i.e., 100%) inner chamber of the sample holder. Depending on the shape of the biological tissue sample, the orifice may be any suitable shape where shapes of interest include, but are not limited to rectilinear shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. In certain embodiments, the orifice is circular. In other embodiments, the orifice is oval. In yet other embodiments, the orifice is polygonal, such as a square, triangular or rectangular.

As discussed in greater detail below, the tissue actuator is displaced along a longitudinal axis within the inner chamber of the sample. In some embodiments, the tissue actuator is displaced in discrete increments, where in certain instances one or more of the inner chamber of the sample holder and the tissue actuator may include one or more notches or protrusions which provide predetermined increments for displacing the tissue actuator within the sample holder. For example, in some instances the inner chamber of the sample holder includes 2 or more notches, such as 3 or more notches, such as 4 or more notches, such as 5 or more notches and including 10 or more notches. In other instances, the inner chamber of the sample holder includes 2 or more protrusions, such as 3 or more protrusions, such as 4 or more protrusions and including 10 or more protrusions. In yet other instances, the inner chamber of the sample holder includes 2 or more notches and protrusions, such as 3 or more notches and protrusions, such as 4 or more notches and protrusions and including 10 or more notches and protrusions.

In some embodiments, the inner chamber of the sample holder has one or more grooves (e.g., complimentary to protrusions on the tissue actuator, as described below) that extends along a length of the sample holder. For example, the sample holder may include 2 or more grooves, such as 3 or more grooves, such as 4 or more grooves, such as 5 or more grooves and including 6 or more grooves. Each groove may extend all or part of the length of the sample chamber, such as 10% or more of the length of the inner chamber, such as 15% or more, such as 20% or more, such as 25% or more, such as 30% or more, such as 40% or more, such as 50% or more, such as 60% or more, such as 75% or more, such as 80% or more, such as 90% or more and including 95% or more. In some embodiments, the grooves extend the entire length (i.e., 100%) of inner chamber of the sample holder. Each groove may be the same length or different. In certain embodiments, each groove is the same length. In other embodiments, two or more grooves extends the same length of sample holder and one or more groove extends a different length. In yet other embodiments, each of the grooves is a different length.

In some embodiments, the inner chamber of the sample holder has threaded walls and is configured to be screw threaded with the outer walls of the tissue actuator. All or part of the walls of the inner chamber may be threaded, such as 10% or more of the length of the inner chamber, such as 15% or more, such as 20% or more, such as 25% or more, such as 30% or more, such as 40% or more, such as 50% or more, such as 60% or more, such as 75% or more, such as 80% or more, such as 90% or more and including 95% or more. In some embodiments, the entire length (i.e., 100%) of inner chamber of the sample holder is threaded.

The sample holder may be formed from any suitable material including, but not limited to, glass, metal or plastic, such as a flexible or rigid plastic, polymeric or thermoplastic materials. For example, suitable polymeric plastics may include acrylonitrile butadiene styrene (ABS), polypropylene, polycarbonates, polyurethanes, polyethers, polyamides, polyimides, or copolymers of these thermoplastics among other polymeric plastic materials. In certain embodiments, the housing is formed from a polyester, where polyesters of interest may include, but are not limited to, housings made of poly(alkylene 2,6-naphthalene-dicarboxylates) such as poly(ethylene 2,6-naphthalene-dicarboxylate); poly(alkylene sulfonyl-4,4'-dibenzoates) such as poly(ethylene sulfonyl-4,4'-dibenzoate); poly(p-phenylene alkylene dicarboxylates) such as poly(p-phenylene ethylene dicarboxylates); poly(trans-1,4-cyclohexanediyl alkylene dicarboxylates) such as poly(trans-1,4-cyclohexanediyl ethylene dicarboxylate); poly(1,4-cyclohexane-dimethylene alkylene dicarboxylates) such as poly(1,4-cyclohexane-dimethylene ethylene dicarboxylate); poly([2.2.2]-bicyclooctane-1,4-dimethylene alkylene dicarboxylates) such as poly([2.2.2]-bicyclooctane-1,4-dimethylene ethylene dicarboxylate); lactic acid polymers and copolymers such as (S)-polylactide, (R,S)-polylactide, poly(tetramethylglycolide), and poly(lactide-co-glycolide); combinations thereof, and the like.

As summarized above, the subject tissue dissociators include a tissue actuator configured to be displaced along a longitudinal axis within the sample holder. The term "displace" refers to moving the tissue actuator within the inner chamber of the sample holder in a manner sufficient to bring the biological tissue sample into contact with and to press the biological tissue sample against the cutting blades to dissociate the tissue into a plurality of tissue fragments. In embodiments, the subject tissue dissociator is configured to be displaced along the longitudinal axis within the sample holder and can be displaced along all or part of the length of the inner chamber of the sample holder, such as 25% or more of the length of the housing, such as 35% or more, such as 50% or more, such as 60% or more, such as 75% or more, such as 90% or more, such as 95% or more, such as 97% or more and including 99% or more of the length of the housing. In certain embodiments, the tissue actuator can be displaced along the entire (i.e., 100%) length of the sample holder.

In some embodiments, the tissue actuator is configured to be displaced in a back-and-forth motion within the sample holder, such as moving from the proximal end to the distal end within the sample holder and back from the distal end to the proximal end. For example, the tissue actuator is configured to be displaced in a back-and-forth motion along 25% or more of the length of the sample holder, such as 35% or more, such as 50% or more, such as 60% or more, such as 75% or more, such as 90% or more, such as 95% or more, such as 97% or more and including 99% or more of the length of the sample holder. In certain embodiments, the tissue actuator can be displaced in a back-and-forth motion along the entire length (i.e., from the proximal end to the distal end) of the sample holder.

The cross-sectional shape of the tissue actuator may vary, depending on the shape of the inner chamber within the sample holder, where cross-sectional shapes of interest include, but are not limited to rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. In some embodiments, the tissue actuator and the inner chamber of the sample holder have the same cross-sectional shape. For example, both the tissue actuator and the inner chamber of the sample may have circular or oval cross sections or both the tissue actuator and the inner chamber of the sample may have a polygonal (e.g., octagonal) cross section. In other embodiments, the tissue actuator and inner chamber within the sample holder have different cross-sectional shapes. For example, the tissue actuator may have a curvilinear cross section and the inner chamber of the sample holder may have a polygonal cross section or the tissue actuator may have a polygonal cross section and the inner chamber of the sample holder may have a curvilinear cross section.

Depending on the amount and type of tissue sample being processed and size of the inner chamber of the sample holder, the dimensions of the tissue actuator may vary where in some instances the length of tissue actuator may range from 1 cm to 50 cm, such as from 2.5 cm to 45 cm, such as from 5 cm to 40 cm, such as from 7.5 cm to 35 cm and including from 10 cm to 25 cm and the width of the tissue actuator may range from 1 cm to 50 cm, such as from 2.5 cm to 45 cm, such as from 5 cm to 40 cm, such as from 7.5 cm to 35 cm and including from 10 cm to 25 cm. Where the tissue actuator has a cylindrical cross-section, the diameter of the of the tissue actuator may vary, in some embodiments, ranging from 0.1 cm to 5 cm, such as from 0.25 cm to 5 cm, such as from 0.5 cm to 4.5 cm, such as from 1 cm to 4 cm, such as from 1.5 cm to 3.5 cm and including from 1 cm to 3 cm. For example, the diameter of the tissue actuator may range from 0.1 cm to 2 cm, such as from 0.2 cm to 1.9 cm, such as from 0.3 cm to 1.8 cm, such as from 0.4 cm to 1.7 cm, such as from 0.5 cm to 1.6 cm, such as from 0.6 cm to 1.5 cm and including from 0.75 cm to 1.25 cm.

In some embodiments, all or part of tissue actuator has a cross-section that is substantially the same size as the inner chamber of the sample holder. In other words, the outer walls of the tissue actuator are flush with the inner walls of the sample holder. For example, 5% or more of the length of the tissue actuator may have a cross section that is substantially the same size as the inner chamber of the sample holder, such as 10% or more, such as 25% or more, such as 50% or more, such as 75% or more, such as 90% or more and including 95% or more of the length of the tissue actuator may have a cross section that is substantially the same size as the inner chamber of the sample holder. In certain embodiments, the entire length of the tissue actuator has a cross section that is substantially the same size as the inner chamber of the sample holder. In some embodiments, one or more of the proximal end and the distal end of the tissue actuator has a cross section that is substantially the same size as the inner chamber of the sample holder with the remaining portion of the tissue actuator having a cross section that is less than the cross section of the inner chamber of the sample holder. For example, in one example, the distal end of the tissue actuator has a cross section that is substantially the same size as the inner chamber of the sample holder with the remaining portion of the tissue actuator having a cross section that is less than the cross section of the inner chamber of the sample holder. In another example, the proximal end of the tissue actuator has a cross section that is substantially the same size as the inner chamber of the sample holder with the remaining portion of the tissue actuator having a cross section that is less than the cross section of the inner chamber of the sample holder. In still another example both the distal end and the proximal end of the tissue actuator has a cross section that is substantially the same size as the inner chamber of the sample holder with the remaining portion of the tissue actuator having a cross section that is less than the cross section of the inner chamber of the sample holder.

In some instances, the outer walls of the tissue actuator form a fluidic seal with the inner chamber of the sample holder. The term "fluidic seal" is used herein in its conventional sense to refer to the absence of space sufficient for fluid to flow between the outer walls of the tissue actuator and the inner chamber of the sample holder. For instance, the distal portion of the tissue actuator may form a fluidic seal with the inner chamber of the sample holder. In other instances, both the distal portion and the proximal portion of the tissue actuator forms a fluidic seal with the inner chamber of the sample holder. In other instances, the entire length of the tissue actuator forms a fluidic seal with the inner chamber of the sample holder. In certain embodiments, the tissue actuator forms a fluidic seal with the sample holder by employing one or more gaskets or O-rings.

As described in greater detail below, tissue is pressed into contact and through the cutting blades by the distal end of the tissue actuator. As such, the distal end of the tissue actuator is configured for contacting the biological tissue sample. In some embodiments, the distal end of the actuator is flat. In other embodiments, the distal end of the tissue actuator has a convex shape. In embodiments, the distal end of the tissue actuator includes a pliable stopper. The term "pliable" is used in its conventional sense to mean that the stopper is capable of being compressed, flexed or otherwise bent without breaking. In these embodiments, the pliable stopper is flexible and is not rigid or stiff. As described in greater detail below, to dissociate biological tissue according to certain embodiments, the tissue actuator is displaced along the longitudinal axis of the sample holder, pressing the pliable stopper through at least one of the cutting blades, such as the mount cutting blades or the cap cutting blades. In certain embodiments, the pliable stopper is configured to be cut by the cutting blades when the tissue actuator is displaced to the distal end of the sample holder. Depending on the thickness of the distal end pliable stopper, the blades may be pressed through 10% or more of the distal end pliable stopper when the tissue actuator is displaced to the distal end of the sample holder, such as 15% or more, such as 25% or more, such as 50% or more, such as 75% or more, such as 90% or more, such as 95% or more, such as 97% or more and including 99% or more of the distal end pliable stopper. In certain embodiments, when the tissue actuator is displaced to the distal end of the sample holder, the blades are pressed through the entire distal end pliable stopper (i.e., the blades cut completely (100%) through the pliable stopper) and contact the tissue actuator).

In some embodiments, the pliable stopper is configured to contact the side edges (i.e., are flush with the side edges) of the cutting blades when the tissue actuator is displaced along the longitudinal axis of the sample holder, such as where the pliable stopper contacts the edges of the cutting blade as the pliable stopper is pressed through the cutting blade. In certain instances, the pliable stopper forms a fluidic seal with the side edges of the cutting blade as the pliable stopper is pressed through the cutting blade. In these embodiments, the pliable stopper is flush with the edge of the cutting blade such that the pliable stopper removes remaining tissue or fluid from the dissociated biological tissue sample on the cutting blades.

In embodiments, when the pliable stopper is pressed through the cutting blades, little to no tissue or fluid from the dissociated biological tissue sample remains on the cutting blades, such as 50% by weight or less of the total amount of biological tissue being dissociated, such as 45% by weight or less, such as 40% by weight or less, such as 35% by weight or less, such as 30% by weight or less, such as 25% by weight or less, such as 20% by weight or less, such as 15% by weight or less, such as 10% by weight or less, such as 9% by weight or less, such as 8% by weight or less, such as 7% by weight or less, such as 6% by weight or less, such as 5% by weight or less, such as 4% by weight or less, such as 3% by weight or less, such as 2% by weight or less, such as 1% by weight or less, such as 0.5% by weight or less, such as 0.1% by weight or less, such as 0.01% by weight or less, such as 0.001% by weight or less and including 0.0001% by weight or less of the total amount of biological tissue being dissociated remains on the cutting blades after the pliable stopper is pressed through the cutting blades. In certain embodiments, when the pliable stopper is pressed through the cutting blades, no biological tissue remains on the cutting blades. As such, tissue dissociators of the present disclosure are configured to dissociate and collect the dissociated biological tissue with little to no excess tissue remaining on the cutting blades or in the sample holder.

Depending on the chemical constitution of specific pliable stoppers employed, pliable stoppers of interest have a compressive strength that ranges from 10 N to 100 N, such as from 20 N to 95 N, such as from 30 N to 90 N, such as from 35 N to 85 N, such as from 40 N to 80 N, such as from 45 N to 75 N and including from 50 N to 70 N. In certain embodiments, the pliable stopper has a compressive strength of from about 50 N to about 60 N, such as from about 50 N to about 55 N. The durometer hardness of pliable stoppers of interest may vary. The durometer hardness of pliable stoppers may range from 10 Shore OO to 100 Shore OO, such as 20 Shore OO to 90 Shore OO, such as 30 Shore OO to 80 Shore OO and including 40 Shore OO to 70 Shore OO. In other embodiments, the durometer hardness of pliable stoppers of interest ranges from 10 Shore A to 100 Shore A, such as 20 Shore A to 90 Shore A, such as 30 Shore A to 80 Shore A and including 40 Shore A to 70 Shore A.

The pliable stopper may be formed from any suitable pliable material, including but not limited to flexible and compressible plastic, polymeric or thermoplastic materials. For example, suitable pliable materials may include polydimethylsiloxane, polybutadiene, chloroprenes, polychloroprenes, butyl rubber, halogenated butyl rubber, styrene-butadiene rubber, nitrile rubber, hydrogenated nitrile rubber, ethylene propylene rubber, ethylene propylene diene rubber, epichlorohydrin rubber, polyacrylic rubber, silicone rubbers, fluorosilicone rubber, fluoroelastomers, perfluoroelastomers, polyether block amides, chlorosulfonated polyethylene, ethylene-vinyl acetate, polysulfide rubber, as well as other soft plastics such as pliable polycarbonates, polyurethanes, polyethers, polyamides, polyimides, or copolymers of these thermoplastics among other polymeric plastic materials. In certain embodiments, the pliable stopper is formed from polydimethylsiloxane.

The cross-sectional shape of the distal end pliable stopper may vary, depending on the shape of the tissue actuator and the inner chamber within the sample holder, where cross-sectional shapes of interest include, but are not limited to rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. In some embodiments, the distal end pliable stopper and the tissue actuator have the same cross-sectional shape. In other embodiments, the distal end pliable stopper and the tissue actuator have different cross-sectional shapes. In some instances, the distal end pliable stopper has a cross-sectional shape that is the same as the orifice of the sample holder. For example, the distal end pliable stopper is flush with the orifice of the sample holder when the tissue actuator is displaced to the distal end of the sample holder.

The pliable stopper may cover all or part of the distal end of the tissue actuator, such as 10% or more of the distal end, such as 15% or more, such as 20% or more, such as 25% or more, such as 50% or more, such as 60% or more, such as 75% or more, such as 80% or more, such as 90% or more, such as 95% or more, such as 97% or more and including 99% or more of the distal end of the tissue actuator. In certain embodiments, the pliable stopper covers the entire distal end of the tissue actuator. As such, the width of the distal end pliable stopper may range from 0.1 cm to 5 cm, such as from 0.5 cm to 4.5 cm, such as from 0.75 cm to 4 cm and including from 1 cm to 3.5 cm. Where the tissue actuator has a cylindrical cross-section, the diameter of the of the distal end pliable stopper may range from 0.1 cm to 5 cm, such as from 0.5 cm to 4.5 cm, such as from 0.75 cm to 4 cm and including from 1 cm to 3.5 cm. Depending on the thickness of the cutting blades as well as the spacing between cutting blades (as described below), the pliable stopper may have a thickness (as measured along the longitudinal axis of the sample holder) that is 0.1 mm or greater, such as 0.5 mm or greater, such as 1 mm or greater, such as 1.5 mm or greater, such as 2 mm or greater, such as 2.5 mm or greater, such as 3 mm or greater, such as 3.5 mm or greater, such as 4 mm or greater, such as 5 mm or greater, such as 7.5 mm or greater, such as 10 mm or greater, such as 15 mm or greater, such as 20 mm or greater and including 25 mm or greater. For example, the thickness of the pliable stopper may range from 0.1 mm to 25 mm, such as from 0.5 mm to 22.5 mm, such as from 1 mm to 20 mm, such as from 2 mm to 17.5 mm, such as from 3 mm to 15 mm, such as from 4 mm to 12.5 mm and including from 5 mm to 10 mm.

In some embodiments, the pliable stopper is affixed to the distal end of the tissue actuator, such as with a fastener where suitable fasteners may include, but are not limited to, hook and loop fasteners, latches, notches, grooves, pins, tethers, hinges as well as permanent or non-permanent adhesives or a combination thereof. In other embodiments, the pliable stopper is added to the distal end of the tissue actuator by stereolithography (3-D printing). In other embodiments, the pliable stopper is co-molded with the tissue actuator. In certain embodiments, the pliable stopper is an integrated part of the tissue actuator. For example, the distal end of the tissue actuator may be formed from a flexible or compressible plastic, polymeric or thermoplastic as described above, such as polydimethylsiloxane, polyisoprene (natural or synthetic), polybutadiene, chloroprenes, polychloroprenes, neoprenes, butyl rubber, halogenated butyl rubber, styrene-butadiene rubber, nitrile rubber, hydrogenated nitrile rubber, ethylene propylene rubber, ethylene propylene diene rubber, epichlorohydrin rubber, polyacrylic rubber, silicone rubber, fluorosilicone rubber, fluoroelastomers, perfluoroelastomers, polyether block amides, chlorosulfonated polyethylene, ethylene-vinyl acetate, polysulfide rubber, as well as other soft plastics such as pliable polycarbonates, polyurethanes, polyethers, polyamides, polyimides, or copolymers of these thermoplastics, such as PETG (glycol-modified polyethylene terephthalate), among other polymeric plastic materials.

In some embodiments, the outer walls of the tissue actuator include one or more aligners configured to orient the tissue actuator within the inner chamber of the sample holder. For example, the outer walls of the tissue actuator may include an alignment protrusion, an alignment rail, an alignment notch, an alignment groove, an alignment slot or a combination thereof. Where the outer walls of the tissue actuator include one or more aligners, the walls of the inner chamber of the sample holder may also include an aligner, such as an aligner which is complimentary to the aligner on the outer walls of the tissue actuator. For example, where the tissue actuator includes an alignment protrusion, the inner chamber of the sample holder inner chamber may include an alignment groove. In another example, where the tissue actuator includes an alignment groove, the inner chamber of the sample holder inner chamber may include an alignment rail.

In certain embodiments, one or more of the tissue actuator and the sample holder includes an indicator that provides for feedback to indicate that a cutting stroke is complete. In these embodiments, when the tissue actuator is displaced to a predetermined location within the sample holder, the indicator provides visual, audible or tactile feedback to the user that the tissue actuator has been displaced a predetermined distance. In some instances, the indicator provides feedback to the user that the tissue actuator has been displaced to the distal end of the sample holder. In other instances, the indicator provides feedback to the user that the cutting motion is complete and that tissue in the sample holder has been dissociated.

In some embodiments, the feedback indicator is a visual marking or a displacement identifier. The visual marking may be any convenient identifier, including but not limited to a colored line, an indentation, a protrusion or tab that provides for a user to visually determine the displacement distance of the tissue actuator. In certain instances, the tissue actuator may include more than one visual marking, such as 2 or more visual markings, such as 3 or more, such as 4 or more, such as 5 or more and including 10 or more visual markings. The visual markings, in certain embodiments, may be positioned at discrete increments along the tissue actuator to provide visual feedback to the user for a plurality of displacement distances. For example, the visual markings may be spaced apart by 1 mm or more, such as 2 mm or more, such as 3 mm or more, such as 4 mm or more, such as 5 mm or more, such as 10 mm or more, such as 15 mm or more, such as 25 mm or more and including 50 mm or more.

In other embodiments the tissue actuator may include one or more tabs, protrusions or some other aligner that makes a sound or produces a vibration when it reaches a predetermined part of the sample holder. The sample holder may also include an aligner (e.g., a hole or groove) that provides for a vibration or audible indication that the aligner on the tissue actuator has reached a predetermined position within the sample holder. The position on the sample holder where the audible or tactile feedback is provided may vary as desired and may be 1 mm or more from the proximal end of the sample holder, such as 2 mm or more, such as 3 mm or more, such as 4 mm or more, such as 5 mm or more, such as 10 mm or more, such as 15 mm or more, such as 25 mm or more and including 50 mm or more from the proximal end of the sample holder. In some instances, tissue dissociators are configured to provide audible or tactile feedback when the tissue actuator has reached 25 mm or less from the distal end of the sample holder, such as 20 mm or less, such as 15 mm or less, such as 10 mm or less, such as 5 mm or less, such as 2 mm or less and including 1 mm or less from the distal end of the sample holder. In certain embodiments, tissue dissociators are configured to provide audible or tactile feedback when the tissue actuator has reached the distal end of the sample holder.

Depending on the displacement of the tissue actuator within the inner chamber of the sample holder, the size of the aligner may vary. For example, the aligner may extend along all or part of the length of the tissue actuator, such as 10% or more of the length of the tissue actuator, such as 15% or more, such as 20% or more, such as 25% or more, such as 30% or more, such as 40% or more, such as 50% or more, such as 60% or more, such as 75% or more, such as 80% or more, such as 90% or more and including 95% or more. In some embodiments, the aligner extends the entire length (i.e., 100%) of the tissue actuator. Accordingly, in embodiments the length of the aligner may vary ranging from 0.1 cm to 25 cm, such as from 0.5 cm to 22.5 cm, such as from 1 cm to 20 cm, such as from 2.5 cm to 15 cm and including from 5 cm to 10 cm and the width of the aligner may vary ranging from 0.01 cm to 5 cm, such as from 0.05 cm to 2.5 cm, such as from 0.1 cm to 2 cm and including from 0.5 cm to 1.5 cm.

The outer walls of the tissue actuator may include 1 or more aligners, such as 2 or more aligners, such as 3 or more aligners, such as 4 or more aligners and include 5 or more aligners. Where the tissue actuator includes more than one aligner, each aligner may be positioned anywhere on the tissue actuator as desired. For example, an aligner may be positioned at a distal end, a proximal end, between the proximal end and the distal end or a combination thereof. Aligners may be positioned on opposite sides of the tissue actuator, such as two aligners on opposite sides at the distal end of the tissue actuator or two aligners on opposite sides at the proximal end of the tissue actuator. In some embodiments, the tissue actuator includes a first aligner at the distal end and a second aligner at the proximal end. In certain embodiments, the aligners are positioned equidistantly from each other. In some instances, each aligner is equidistantly spaced from the distal end of the tissue actuator or the proximal end of the tissue actuator.

In embodiments of the present disclosure, tissue dissociators include a blade holder having a mount with one or more cutting blades and a cap with one or more cutting blades. The cap has a proximal end and distal end with walls between the distal end and proximal end that together form an inner chamber where the proximal end is coupled to the distal end of the sample holder. As described above, in some instances the sample holder is coupled to the cap by a fastener, such as a latch, a notch, a groove, a pin, a tether, a hinge, a non-permanent adhesive. In other instances, the sample holder is coupled to the cap by screw threading the cap to the sample holder. In yet other instances, the sample holder is co-molded to the cap. In still other instances, the sample holder and the cap form a single integrated sample holder having one or more cutting blades.

The cap may be any cross-sectional shape where suitable cross-sectional shapes include but are not limited to rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. In certain embodiments, the cap has polygonal cross-sectional shape such as a square or a polygon. In other embodiments, the mount has a circular cross-sectional shape. The cross-sectional shape of the cap may be the same or different from the mount (as described below). In some instances, the cross-sectional shape of the cap is the same as the mount. In other instances, the cross-sectional shape of the cap is different from the mount.

Depending on the size of the cutting blades (as described below), the cap may have a length that varies, ranging from 0.1 cm to 10 cm, such as from 0.5 cm to 9.5 cm, such as from 1 cm to 9 cm, such as from 1.5 cm to 8.5 cm, such as from 2 cm to 8 cm, such as from 2.5 cm to 7.5 cm, such as from 3 cm to 7 cm, such as from 3.5 cm to 6.5 cm and including from 4 cm to 6 cm. The cross-sectional width of the cap may range from 0.5 cm to 15 cm, such as from 1 cm to 14 cm, such as from 2 cm to 13 cm, such as from 3 cm to 12 cm, such as from 4 cm to 11 cm and including from 5 cm to 10 cm.

The cap has an orifice that extends across the cross-sectional width of the cap. The orifice may be co-axial with the longitudinal axis of the cap (i.e., share a center with the cap cross-section) or may be off-center. In some embodiments, the orifice is positioned at the proximal end of the cap (i.e., at the distal end of the sample holder). In other embodiments, the orifice is positioned at the distal end of the cap. The orifice may extend across 10% or more of the cross-sectional width of the cap, such as 15% or more, such as 20% or more, such as 25% or more, such as 30% or more, such as 35% or more, such as 40% or more, such as 45% or more, such as 50% or more, such as 75% or more, such as 90% or more, such as 95% or more and including an orifice that extends 99% of the cap cross-section. Accordingly, the mount orifice may range from 0.5 cm to 15 cm, such as from 1 cm to 14 cm, such as from 2 cm to 13 cm, such as from 3 cm to 12 cm, such as from 4 cm to 11 cm and including from 5 cm to 10 cm.

In embodiments, the cap and mount include 1 or more cutting blades, such as 2 or more cutting blades, such as 3 or more cutting blades, such as 5 or more cutting blades, such as 10 or more cutting blades and including 25 or more cutting blades. The term "cutting blade" is used herein in its conventional sense to refer to any surface having an edge that is sufficiently narrow to puncture, slice or otherwise cut through a biological tissue sample. Cutting blades according to embodiments may be formed from any suitable cutting material, including but not limited to metal, glass, ceramic, or plastic. In some embodiments, the cutting blades are formed from a metal, such as aluminum, gold, indium, iron, nickel, tin, steel (e.g., stainless steel), silver and combinations and alloys thereof. In other embodiments, the cutting blades are formed from a metal alloy, such as an aluminum alloy, aluminum-lithium alloy, an aluminum-nickel-copper alloy, an aluminum-copper alloy, an aluminum-magnesium alloy, an aluminum-magnesium oxide alloy, an aluminum-silicon alloy, an aluminum-magnesium-manganese-platinum alloy, a copper-gold alloy, a gold alloy, a gold-silver alloy, an indium alloy, an indium-tin alloy, an indium-tin oxide alloy, an iron alloy, an iron-chromium alloy (e.g., steel), an iron-chromium-nickel alloy (e.g., stainless steel), an iron-silicon alloy, an iron-chromium-molybdenum alloy, an iron-carbon alloy, an iron-boron alloy, an iron-magnesium alloy, an iron-manganese alloy, an iron molybdenum alloy, an iron-nickel alloy, an iron-phosphorus alloy, an iron-titanium alloy, an iron-vanadium alloy, a nickel alloy, a nickel-manganese-aluminum-silicon alloy, a nickel-chromium alloy, a nickel, molybdenum-chromium-tungsten alloy, a nickel-copper-iron-manganese alloy, a nickel-carbon alloy, a nickel-chromium-iron alloy, a nickel-silicon alloy, a nickel-titanium alloy, a silver alloy, a silver-copper alloy (e.g., sterling silver) a silver-copper-germanium alloy (e.g., Argentium sterling silver), a silver-gold alloy, a silver-copper-gold alloy, a silver-platinum alloy, a tin alloy, a tin-copper-antimony alloy, a titanium alloy, a titanium-vanadium-chromium alloy, a titanium-aluminum alloy, a titanium-aluminum-vanadium alloy, a zirconium alloy, a zirconium-tin alloy or a combination thereof.

In certain embodiments, the cutting blades are formed from a plastic, such as a rigid plastic, polymeric or thermoplastic material. For example, suitable plastics may include polycarbonates, polyurethanes, polyethers, polyamides, polyimides, or copolymers of these thermoplastics among other polymeric plastic materials. In certain embodiments, the cutting blades are formed from a polyester, where polyesters of interest may include, but are not limited to poly(alkylene adipates) such as poly(ethylene adipate), poly(1,4-butylene adipate), and poly(hexamethylene adipate); poly(alkylene suberates) such as poly(ethylene suberate); poly(alkylene sebacates) such as poly(ethylene sebacate); poly(ε-caprolactone) and poly(β-propiolactone); poly(alkylene 2,6-naphthalene-dicarboxylates) such as poly(ethylene 2,6-naphthalene-dicarboxylate); poly(alkylene sulfonyl-4,4'-dibenzoates) such as poly(ethylene sulfonyl-4,4'-dibenzoate); poly(p-phenylene alkylene dicarboxylates) such as poly(p-phenylene ethylene dicarboxylates); poly(trans-1,4-cyclohexanediyl alkylene dicarboxylates) such as poly(trans-1,4-cyclohexanediyl ethylene dicarboxylate); poly(1,4-cyclohexane-dimethylene alkylene dicarboxylates) such as poly(1,4-cyclohexane-dimethylene ethylene dicarboxylate); poly([2.2.2]-bicyclooctane-1,4-dimethylene alkylene dicarboxylates) such as poly([2.2.2]-bicyclooctane-1,4-dimethylene ethylene dicarboxylate); lactic acid polymers and copolymers such as (S)-polylactide, (R,S)-polylactide, poly(tetramethylglycolide), and poly(lactide-co-glycolide), combinations thereof, and the like.

In embodiments, tissue dissociators include a cap having one or more cutting blades. Depending on the shape of the dissociated tissue fragments desired, the configuration of the cap cutting blades may vary. In some instances, the cutting blade includes a single blade traversing the cap orifice. For instance, in one example the single blade is positioned across the midline of the cap orifice. In another example, the single blade is positioned a predetermined distance from the midline of the distal end of the cap, such as 1 mm or more from the midline of the cap, such as 2 mm or more, such as 3 mm or more, such as 5 mm or more, such as 7 mm or more and including 10 mm or more from the midline of the distal end of the cap.

In some embodiments, the cap cutting blade is configured as an array of blades, such as a plurality of blades arranged in parallel rows that extend across the cap orifice. For example, the cap cutting blade may be arranged in 2 parallel rows or more, such as 3 parallel rows or more, such as 4 or parallel rows or more, such as 5 parallel rows or more, such as 10 parallel rows or more, such as 15 parallel rows or more, such as 25 parallel rows or more and including 50 parallel rows or more. The distance between each blade may vary, depending the size of dissociated tissue fragments desired and may be 0.01 mm or greater, such as 0.05 mm or greater, such as 0.1 mm or greater, such as 0.5 mm or greater, such as 1 mm or greater, such as 1.5 mm or greater, such as 2 mm or greater, such as 3 mm or greater, such as 5 mm or greater and including a distance between blades of 10 mm or greater. The distance between each row may be the same, different or some combination thereof. In some instances, the distance between each blade row is the same. In other instances, the distance between each blade row is different. In yet other instances, a first portion of the blade rows are positioned equidistant from each other while a second portion of blade rows are positioned at varying distances from each other.

The one or more cap cutting blades may be coupled to the cap by any convenient protocol. In some embodiments, the one or more cap cutting blades are an integrated part of the mount, including where the cutting blade is soldered, welded or affixed to the cap using a permanent adhesive. In certain embodiments, the cutting blade is co-molded to the mount. In other embodiments, the one or more cap cutting blades are releasably attached to the cap. By "releasably" is meant that one or more of the cap cutting blades can be freely detached from and re-attached to the cap. Where the cutting blade is releasably attached to the cap, the cutting blade may be non-permanently fastened to the cap by any convenient attachment protocol, including but not limited to a latch, a notch, a groove, a pin, a tether, a hinge, non-permanent adhesive, a threaded screw, or a combination thereof. In certain instances, the cutting blade includes a threaded outer wall and is screw threaded with the internal walls of the cap.

In embodiments, the subject blades holder also includes a mount having one or more cutting blades that is configured to be coupled to the cap. The mount may be any cross-sectional shape where suitable cross-section shapes include but are not limited to rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. In certain embodiments, the mount has polygonal cross-sectional shape such as a square or a polygon. In other embodiments, the mount has a circular cross-sectional shape. Depending on the size of the cutting blades (as described below), the mount may have a length that varies, ranging from 0.1 cm to 10 cm, such as from 0.5 cm to 9.5 cm, such as from 1 cm to 9 cm, such as from 1.5 cm to 8.5 cm, such as from 2 cm to 8 cm, such as from 2.5 cm to 7.5 cm, such as from 3 cm to 7 cm, such as from 3.5 cm to 6.5 cm and including from 4 cm to 6 cm. The cross-sectional width of the mount may range from 0.5 cm to 15 cm, such as from 1 cm to 14 cm, such as from 2 cm to 13 cm, such as from 3 cm to 12 cm, such as from 4 cm to 11 cm and including from 5 cm to 10 cm.

The mount has an orifice that extends across the width of the mount. The orifice may be co-axial with the longitudinal axis of the mount (i.e., share a center with the mount cross-section) or may be off-center. The orifice may extend across 10% or more of the cross-sectional width of the mount, such as 15% or more, such as 20% or more, such as 25% or more, such as 30% or more, such as 35% or more, such as 40% or more, such as 45% or more, such as 50% or more, such as 75% or more, such as 90% or more, such as 95% or more and including an orifice that extends 99% of the mount cross-section. Accordingly, the mount orifice may range from 0.5 cm to 15 cm, such as from 1 cm to 14 cm, such as from 2 cm to 13 cm, such as from 3 cm to 12 cm, such as from 4 cm to 11 cm and including from 5 cm to 10 cm.

In embodiments, the mount includes 1 or more cutting blades, such as 2 or more cutting blades, such as 3 or more cutting blades, such as 5 or more cutting blades, such as 10 or more cutting blades and including 25 or more cutting blades. Depending on the shape of the dissociated tissue fragments desired, the configuration of the mount cutting blades may vary. In some instances, the cutting blade includes a single blade traversing the orifice of the mount. For instance, in one example the single blade is positioned across the midline of the mount orifice. In another example, the single blade is positioned a predetermined distance from the midline of the distal end of the mount, such as 1 mm or more from the midline of the mount, such as 2 mm or more, such as 3 mm or more, such as 5 mm or more, such as 7 mm or more and including 10 mm or more from the midline of the distal end of the mount.

In some embodiments, the mount cutting blade is configured as an array of blades, such as a plurality of blades arranged in parallel rows that extend across the mount orifice. For example, the mount cutting blade may be arranged in 2 parallel rows or more, such as 3 parallel rows or more, such as 4 or parallel rows or more, such as 5 parallel rows or more, such as 10 parallel rows or more, such as 15 parallel rows or more, such as 25 parallel rows or more and including 50 parallel rows or more. The distance between each blade may vary, depending the size of dissociated tissue fragments desired and may be 0.01 mm or greater, such as 0.05 mm or greater, such as 0.1 mm or greater, such as 0.5 mm or greater, such as 1 mm or greater, such as 1.5 mm or greater, such as 2 mm or greater, such as 3 mm or greater, such as 5 mm or greater and including a distance between blades of 10 mm or greater. The distance between each row may be the same, different or some combination thereof. In some instances, the distance between each blade row is the same. In other instances, the distance between each blade row is different. In yet other instances, a first portion of the blade rows are positioned equidistant from each other while a second portion of blade rows are positioned at varying distances from each other.

The one or more cutting blades may be coupled to the mount by any convenient protocol. In some embodiments, the one or more mount cutting blades are an integrated part of the mount, including where the cutting blade is soldered, welded or affixed to the mount using a permanent adhesive. In other embodiments, the one or more mount cutting blades are releasably attached to the mount. In these embodiments, the one or more of the mount cutting blades can be freely detached from and re-attached to the mount. Where the cutting blade is releasably attached to the mount, the cutting blade may be non-permanently fastened to the mount by any convenient attachment protocol, including but not limited to a latch, a notch, a groove, a pin, a tether, a hinge, non-permanent adhesive, a threaded screw, or a combination thereof. In certain instances, the cutting blade includes a threaded outer wall and is screw threaded with the internal walls of the mount.

In embodiments, the mount and the cap cutting blades are oriented at an angle with respect to each other, e.g., an angle of from 1° to 90° with respect to each other, such as where the mount cutting blades are oriented at an angle of from 5° to 85° with respect to the cap cutting blades, such as from 10° to 80°, such as from 15° to 75°, such as from 20° to 70°, such as from 25° to 65° and including where the mount cutting blades are oriented at an angle of from 30° to 60° with respect to the cap cutting blades. In certain embodiments, the mount cutting blades are positioned orthogonally (90°) with respect to a cap cutting blades. In embodiments, the mount cutting blades and cap cutting blades combine to form a grid-shaped cutting surface (i.e., the cutting surfaces of the mount cutting blades and the cap cutting blades form rectilinear intersecting cutting surfaces, such as e.g., cutting surfaces in the shape of squares, rectangles or curvilinear shapes). Each unit (e.g., square, rectangle) of the grid-shaped cutting blades of interest may be congruent or incongruent or a combination thereof. Depending on the size of the cutting blade and size of dissociated tissue desired, the area of each unit may vary, ranging from 0.01 mm$^2$ to 100 mm$^2$, such as 0.1 mm$^2$ to 90 mm$^2$, such as 0.5 mm$^2$ to 80 mm$^2$, such as 0.75 mm$^2$ to 70 mm$^2$, such as 1 mm$^2$ to 60 mm$^2$, and including 2 mm$^2$ to 50 mm$^2$.

Where the mount cutting blades are positioned orthogonally with respect to the cap cutting blades, the mount cutting blades and cap cutting blades combine to form a grid-shaped cutting surface that is configured to dissociate a biological tissue sample into a plurality of components having substantially the same size and shape. By substantially the same size and shape is meant that the subject tissue dissociators are configured to dissociate a biological tissue sample into tissue fragments which vary in shape or size by 5% or less, such as by 4.5% or less, such as by 4% or less, such as by 3.5% or less, such as by 3% or less, such as by 2.5% or less, such as by 2% or less, such as by 1.5% or less, such as by 1% or less, such as by 0.5% or less, such as by 0.1% or less and including being configured to dissociate a biological tissue sample into tissue fragments which vary in shape or size which vary by 0.01% or less.

For example, the tissue dissociators may be configured to dissociate the biological tissue sample into a plurality of tissue fragments which vary in size by 5% or less, such as by 4.5% or less, such as by 4% or less, such as by 3.5% or less, such as by 3% or less, such as by 2.5% or less, such as by 2% or less, such as by 1.5% or less, such as by 1% or less, such as by 0.5% or less, such as by 0.1% or less and including being configured to dissociate a biological tissue sample into a plurality of tissue fragments which vary in size by 0.01% or less. In certain instances, the tissue dissociator is configured to dissociate a biological tissue sample into a plurality of tissue fragments that have identical sizes. For example, the tissue dissociator may be configured to dissociate the biological tissue sample into a plurality of tissue fragments having a cross section that varies by 5% or less, such as by 4.5% or less, such as by 4% or less, such as by 3.5% or less, such as by 3% or less, such as by 2.5% or less, such as by 2% or less, such as by 1.5% or less, such as by 1% or less, such as by 0.5% or less, such as by 0.1% or less and including being configured to dissociate a biological tissue sample into a plurality of tissue fragments having a cross section that varies by 0.01% or less.

In some embodiments, the tissue dissociator is configured to dissociate a biological tissue sample into tissue fragments which vary in shape by 5% or less, such as by 4.5% or less, such as by 4% or less, such as by 3.5% or less, such as by 3% or less, such as by 2.5% or less, such as by 2% or less, such as by 1.5% or less, such as by 1% or less, such as by 0.5% or less, such as by 0.1% or less and including being configured to dissociate a biological tissue sample into tissue fragments which vary in shape by 0.01% or less. In certain instances, the tissue dissociator is configured to dissociate a biological tissue sample into a plurality of tissue fragments that have identical shape.

In some embodiments, the cutting blades of the mount and the cap are reusable. By "reusable" is meant that the cutting blade is capable of more than a single use where there is little to no degradation or reduction in performance by the cutting blade after each use. As such, cutting blades in the subject tissue dissociators may be reused 1 more or times, such as 2 or more times, such as 3 or more times, such as 5 or more times, such as 10 or more times, such as 25 or more times, such as 50 or more times and including 100 or more times.

In embodiments, cutting blades show little to no degradation or reduction in performance after each use. The subject cutting blades degrade by 5% or less during each use, such as by 4.5% or less, such as by 4% or less, such as by 3.5% or less, such as by 3% or less, such as by 2.5% or less, such as by 2% or less, such as by 1.5% or less, such as by 1% or less, such as by 0.5% or less and including degrading by 0.1% or less during each use. In certain embodiments, there is no (i.e., 0%) degradation of the cutting blades after each use. Accordingly, the performance of the cutting blades is reduced by 5% or less after each use, such as by 4.5% or less, such as by 4% or less, such as by 3.5% or less, such as by 3% or less, such as by 2.5% or less, such as by 2% or less, such as by 1.5% or less, such as by 1% or less, such as by 0.5% or less and including a reduction in performance by 0.1% or less after each use. In certain embodiments, the performance of the cutting blades is entirely unaffected by each use.

Where the cutting blades are reused, methods may further include washing the cutting blades after use or prior to subsequent use, as described in greater detail below. The cutting blades may be washed by any convenient protocol, such as by washing with a solvent, using heat, electromagnetic radiation (e.g., ultraviolet light) or by ultrasound, among other washing protocols.

In certain embodiments, the blade holder includes one or more aligners for maintaining alignment between the mount cutting blades and the cap cutting blades. In some instances, maintaining alignment between the mount cutting blades and the cap cutting blades includes aligning the mount orifice and the cap orifice. The mount and cap may include any number of aligners, so long as coupling of the aligners on the mount to the aligners on the cap is sufficient to position and maintain alignment between the mount and the cap. For example, the mount and cap may each include 2 or more aligners, such as 3 or more aligners, such as 4 or more aligners, such as 5 or more aligners, such as 7 or more aligners and including 10 or more aligners. Any suitable type of aligner may be employed, such as an alignment holes, protrusions, grooves, pins, notches, countersinks, counterbores, dowels, magnets or any combination thereof. In one example, the cap includes one or more alignment holes or bores and is coupled to a mount having one or more alignment pins or protrusions. In another example, the cap includes one or more alignment pins or protrusions and the mount includes one or more alignment holes or bores. In yet another example, the cap includes one or more alignment grooves and the mount includes one or more alignment notches. In still another example, the cap includes one or more alignment notches and the mount includes one or more alignment grooves. In still another example, the cap includes one or more press-fit dowels and the mount includes one or more holes to receive the press-fit dowel. In still another example, the mount includes one or more press-fit dowels and the cap includes one or more holes to receive the press-fit dowel. In still another example, the cap and the mount each include one or more alignment magnets which couple together to align the cap with the mount.

The shape of aligners on the mount and cap may vary, where cross-sectional shapes of interest include, but are not limited to rectilinear cross sectional shapes, e.g., squares, rectangles, trapezoids, triangles, hexagons, etc., curvilinear cross-sectional shapes, e.g., circles, ovals, as well as irregular shapes, e.g., a parabolic bottom portion coupled to a planar top portion. In some embodiments, the aligners are cylindrically shaped. In other embodiments, the aligners are spherical. In yet other embodiments, the aligners are polygonal-shaped, such as square-shaped or rectangular.

The width of each aligner may vary, ranging in some instances from 1 mm to 25 mm, such as from 2 mm to 22 mm, such as from 3 mm to 20 mm, such as from 4 mm to 17 mm and including from 5 mm to 15 mm. The length of each aligner on the mount or cap ranges from 1 mm to 50 mm, such as from 2 mm to 45 mm, such as from 3 mm to 40 mm, such as from 4 m to 35 mm, such as from 5 mm to 30 mm and including from 10 mm to 20 mm. Where the aligner on the mount or the cap is an alignment recess, such as a notch, a countersink, a counter-bore, a slot, a groove or a hole, the depth of the aligner may range from 1 mm to 50 mm, such as from 2 mm to 45 mm, such as from 3 mm to 40 mm, such as from 4 m to 35 mm, such as from 5 mm to 30 mm and including from 10 mm to 20 mm.

The aligners may be positioned at any location on the mount. For example, in some embodiments one or more aligners are positioned adjacent to outer peripheral edge of the mount, such as 1 mm or more from the edge of the mount, such as 2 mm or more, such as 3 mm or more, such as 4 mm or more and including 5 mm or more from the outer edge of the mount. Where the cross-sectional shape of the mount is polygonal, one or more aligners may be positioned at the corners of the mount. For example, where the mount has a square or rectangular cross-section, the aligners may be positioned at one or more of the four corners of the square or rectangle distal end of the mount.

Where the mount includes more than one aligner, the distance between each aligner may vary, being spaced apart by 2 mm or more, such as by 3 mm or more, such as by 5 mm or more, such as by 7 mm or more, such as by 10 mm or more and including by 25 mm or more. Where the mount includes three or more aligners, the distance between each aligner may be the same or different or a combination thereof. In some embodiments, the distance between each aligner is different. In other embodiments, each aligner is spaced equidistant from each other. In certain embodiments, the mount includes 4 aligners that are positioned equidistantly spaced along the outer edge of the mount. For instance, the mount may include 4 polygonal-shaped (e.g., square or rectangular) recesses positioned at the four corners of the mount.

The aligners may also be positioned at any location on the cap. For example, in some embodiments one or more aligners are positioned adjacent to outer peripheral edge of the cap, such as 1 mm or more from the edge of the cap, such as 2 mm or more, such as 3 mm or more, such as 4 mm or more and including 5 mm or more from the outer edge of the cap. Where the cross-sectional shape of the cap is polygonal, one or more aligners may be positioned at the corners of the cap. For example, where the cap has a square or rectangular cross-section, the aligners may be positioned at one or more of the four corners of the square or rectangle cap.

Where the cap includes more than one aligner, the distance between each aligner may vary, being spaced apart by 2 mm or more, such as by 3 mm or more, such as by 5 mm or more, such as by 7 mm or more, such as by 10 mm or more and including by 25 mm or more. Where the cap includes three or more aligners, the distance between each aligner may be the same or different or a combination thereof. In some embodiments, the distance between each aligner is different. In other embodiments, each aligner is spaced equidistant from each other. In certain embodiments, the cap includes 4 aligners that are positioned equidistantly spaced along the outer edge of the cap. For instance, the cap may include 4 polygonal-shaped (e.g., square or rectangular) recesses positioned at the four corners of the cap.

The mount and cap may also include one or more fasteners for coupling the mount to the cap. In some cases the mount is configured to be releasably attached to the cap. In these embodiments, the mount may be freely detached and re-attached to the cap. Suitable fasteners for releasably attaching the mount to the cap may include, but are not limited to latches, notches, countersinks, counter-bores, grooves, pins, tethers, hinges non-permanent adhesives or a combination thereof. In certain instances, the mount includes one or more screw threads for coupling to the cap. In certain embodiments, the mount permanently affixed to the cap, such as by soldering, welding or affixing to the mount to the cap using a permanent adhesive.

In some embodiments, tissue dissociators of interest are configured to be releasably attached to a container. In these embodiments, the tissue dissociator can be freely detached from and re-attached to the container. In some embodiments, the tissue dissociator is configured to be placed inside and attached to the container. All or part of the tissue dissociator housing may be configured to fit inside of the container, such as 10% or more, such as 25% or more, such as 50% or more, such as 75% or more, such as 90% or more and including 95% or more of the tissue dissociator housing may be configured to fit within the container.

In certain embodiments, the container is configured to be attached to the blade holder of the tissue dissociator. For example, the container may be coupled to the cap component of the blade holder. In other embodiments, the container is coupled to the mount component of the blade holder. The blade holder may include one or more fasteners for attaching the dissociator to the container. Suitable fasteners may include, but are not limited to, latches, notches, grooves, pins, tethers, hinges, non-permanent adhesives or a combination thereof.

In certain instances, the inner wall of the cap is threaded and is configured to be screw threaded with the outer wall of the container. Depending on the type of container employed, all or part of the inner wall of cap may be threaded, such as 10% or more of the length of the inner wall of cap, such as 15% or more, such as 20% or more, such as 25% or more, such as 30% or more, such as 40% or more, such as 50% or more, such as 60% or more, such as 75% or more, such as 80% or more, such as 90% or more and including 95% or more. In some embodiments, the entire length (i.e., 100%) of inner wall of the cap is threaded.

Containers of interest may vary and may include but are not limited to a blood collection tube, test tube, centrifuge tube, culture tube, falcon tube, microtube, Eppendorf tube, specimen collection container, specimen transport container, petri dish and syringe.

FIG. 1 depicts a tissue dissociator 100 according to certain embodiments of the present disclosure. Each component of tissue dissociator 100 has a circular cross-section includes sample holder 101, cap 102, cap cutting blades 102a, mount 103, mount cutting blades 103a and tissue actuator 104 having a distal end pliable stopper 105. Distal end pliable stopper is attached to the tissue actuator with an adhesive, in some instances with an O-ring (e.g., to provide a fluidic seal). Tissue actuator 104 includes protrusions 104a for maintaining alignment during displacement in sample holder 101. Two smaller tabs are also present on the tissue actuator to provide for audible or tactile feedback indicating that tissue actuator 104 has reached a predetermined distance within sample holder 101 or that the cutting stroke is complete. These tabs are located just below the tissue actuator push button and are positioned at an angle (e.g., 90° angle) with respect to alignment protrusions 104a. Sample holder 101 includes grooves 101a which align with protrusions 104a. Mount 103 also includes alignment protrusion 103b for maintaining positioning with respect to cap 102 by fitting into alignment hole 102b in cap 102. Sample holder 104 also includes wall features on the inside wall which are configured to couple with the feedback tabs of the tissue actuator, providing one or more of audible or tactile feedback that tissue actuator 101 has reached an predetermined distance within sample holder 101. Cap 102 also includes screw thread 102c along the internal walls such that tissue dissociator 100 is configured to be releasably attached to a container, such as a test tube (e.g., conical tube, culture tube, falcon tube, blood collection tube, etc.)

Figure 2:
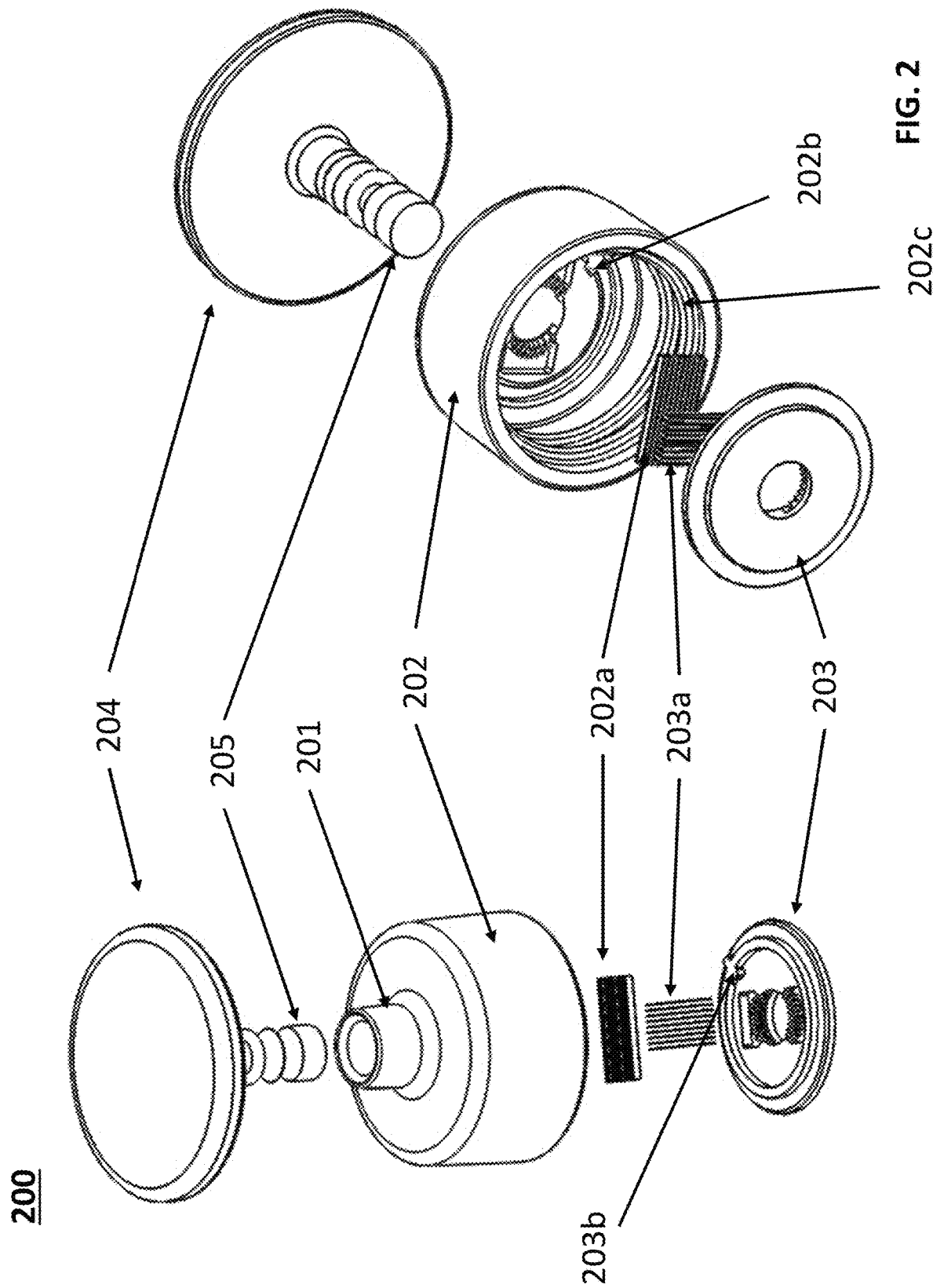
FIG. 2 illustrates aspects of a tissue dissociator according to another embodiment of the present disclosure.

FIG. 2 depicts a tissue dissociator according to another embodiment of the present disclosure. Each component of tissue dissociator 200 has a circular cross-section and includes sample holder 201, cap 202, cap cutting blades 202a, mount 203, mount cutting blades 203a and tissue actuator 204 having a distal end pliable stopper 205. Mount 203 also includes alignment protrusion 203b for maintaining positioning with respect to cap 202 by fitting into alignment groove 202b in cap 202. Cap 202 also includes screw thread 202c along the internal walls such that tissue dissociator 200 is configured to be releasably attached to a container, such as a test tube (e.g., conical tube, culture tube, falcon tube, blood collection tube, etc.)

Figure 3:
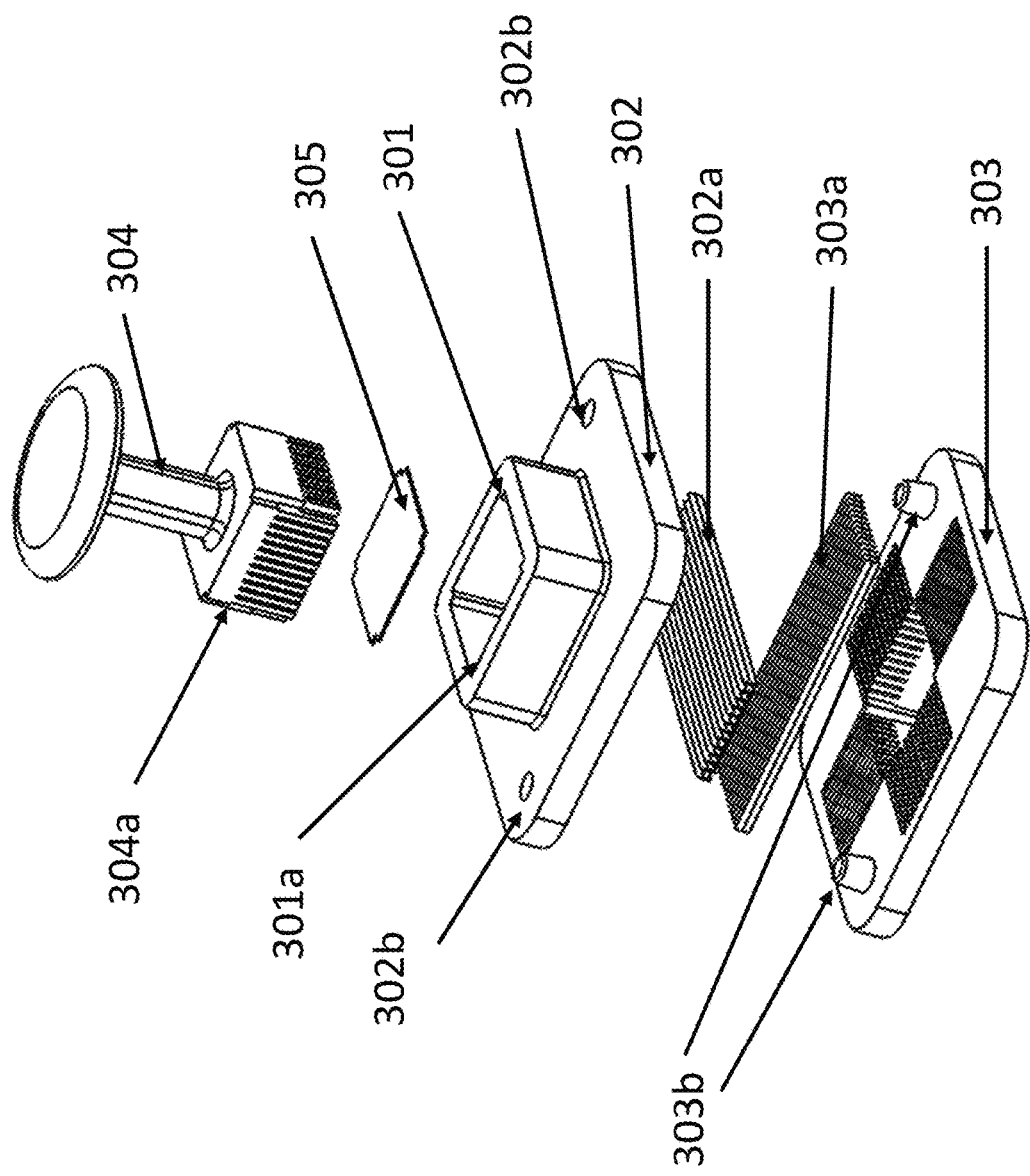
FIG. 3 depicts a tissue dissociator according to another embodiment of the present disclosure.

FIG. 3 depicts a tissue dissociator according to another embodiment of the present disclosure. Each component of tissue dissociator 300 has a square cross-section and includes sample holder 301, cap 302 with cap cutting blades 302a, mount 303 with mount cutting blades 303a and tissue actuator 304 having a distal end pliable stopper 305. Mount 303 also includes two alignment protrusions 303b for maintaining positioning with respect to cap 302 by fitting into alignment holes 302b in cap 302. Tissue actuator 304 also includes four alignment cutouts 304a at each corner which provide for alignment with four alignment ribs 301a at the corners of sample holder 301.

Figure 4:
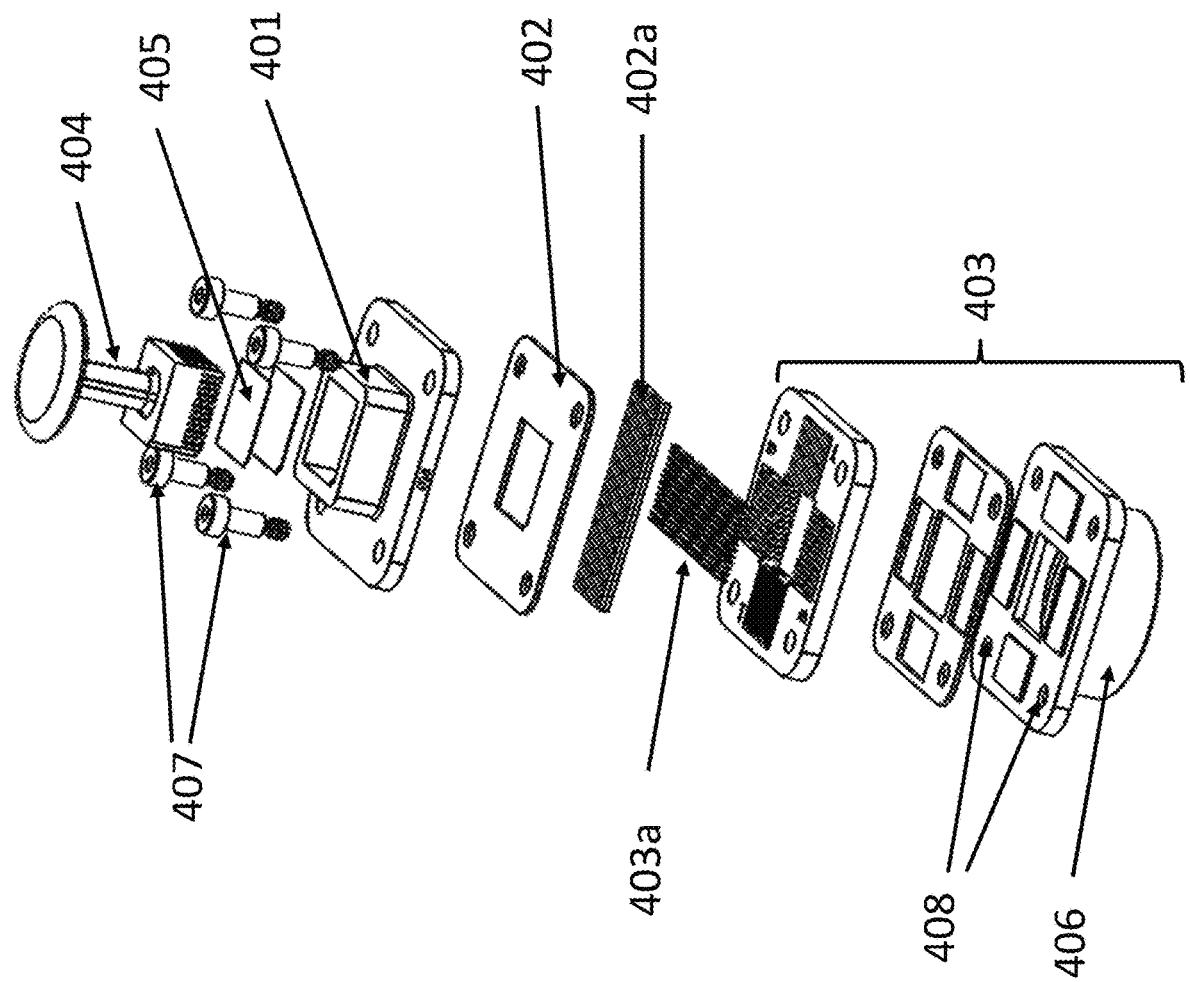
FIG. 4 depicts a tissue dissociator according to another embodiment of the present disclosure.

FIG. 4 depicts a tissue dissociator according to another embodiment of the present disclosure. Tissue dissociator 400 includes sample holder and cap 401, flexible gasket 402 with cap cutting blades 402a, mount 403 with mount cutting blades 403a and tissue actuator 404 with distal end pliable stopper 405. The distal end of tissue actuator 404, pliable stopper 405, sample holder and cap 401, gasket 402 and mount 403 each have a square cross-section. The proximal end of tissue actuator 404 has a circular handle. Mount 403 includes a blade holder for positioning mount cutting blade 403a as well as connector 406 configured for coupling tissue dissociator 400 to a container. Flexible gasket 402 is fastened to sample holder and cap 401 and mount 403 with screws 407 through holes 408 in each component.

Figure 5:
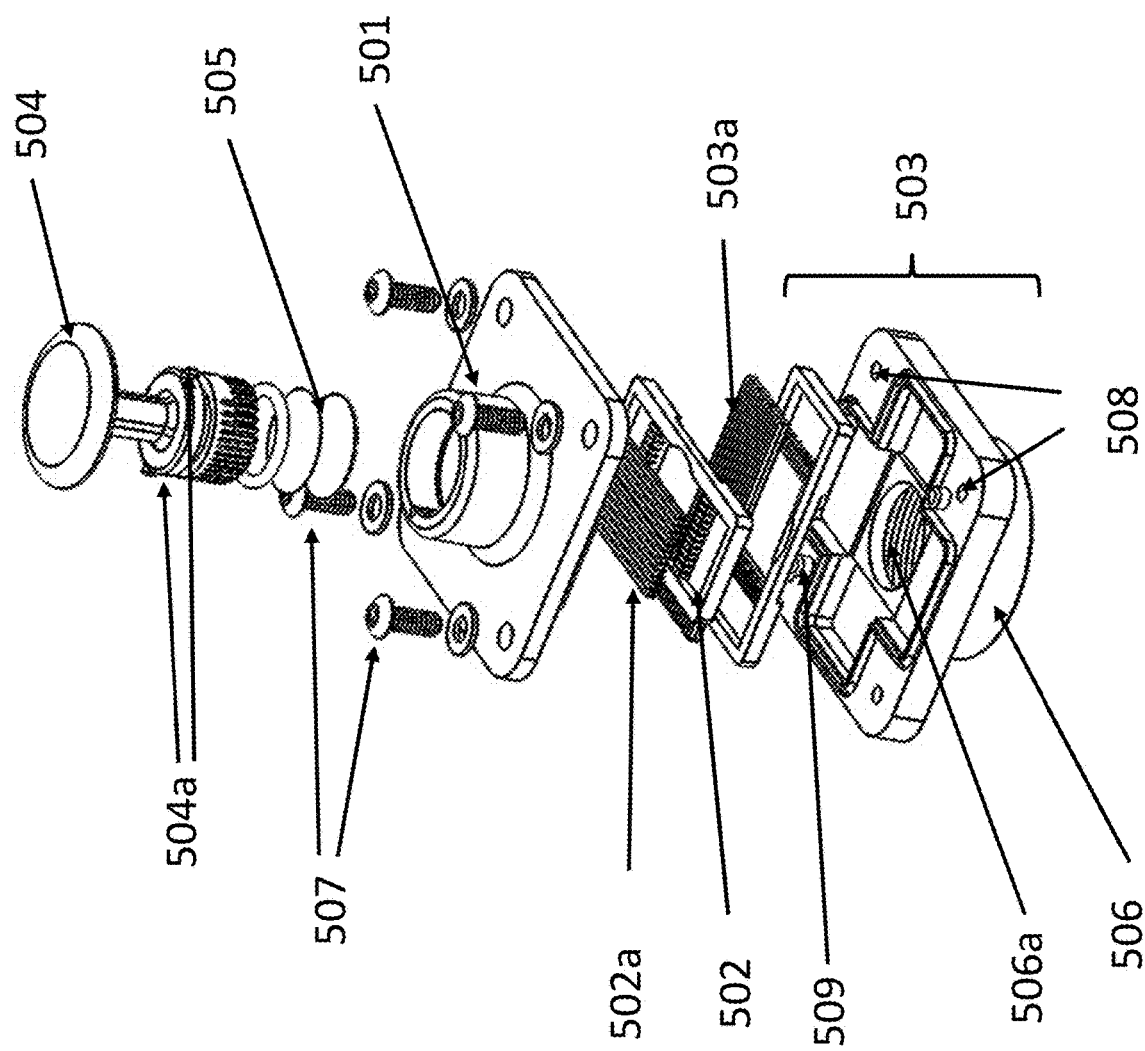
FIG. 5 depicts a tissue dissociator according to another embodiment of the present disclosure.

FIG. 5 depicts a tissue dissociator according to another embodiment of the present disclosure. Tissue dissociator 500 includes sample holder and cap 501, cutting blade holder 502 with cap cutting blades 502a, mount 503 with mount cutting blades 503a and tissue actuator 504 with distal end pliable stopper 505. Distal end pliable stopper is attached to the tissue actuator with an adhesive, in some instances with an O-ring (e.g., to provide a fluidic seal). Tissue actuator 504 includes protrusions 504a for aligning the tissue actuator during displacement in sample holder and cap 501. The distal end of tissue actuator 504 has a circular cross-section. Mount 503 includes a blade holder so that mount cutting blade 503a is positioned in a recess in mount 503. Cutting blade holder 502 is recessed into mount 503. Mount 503 is configured with connector 506 for coupling tissue dissociator 500 to a container. Connector 506 has an internal screw threaded wall 506a and is configured to be connected by screw-threading mount 503 to a container (e.g., conical tube, falcon tube, etc.) Mount 503 includes alignment protrusions 509 that couples with holes (not shown) on sample holder 501 to maintain alignment of sample holder and cap 501, cutting blade holder 502 and mount 503. Sample holder and cap 501 is fastened to cutting blade holder 502 and mount 503 with screws 507 through holes 508 in each component.

Figure 6:
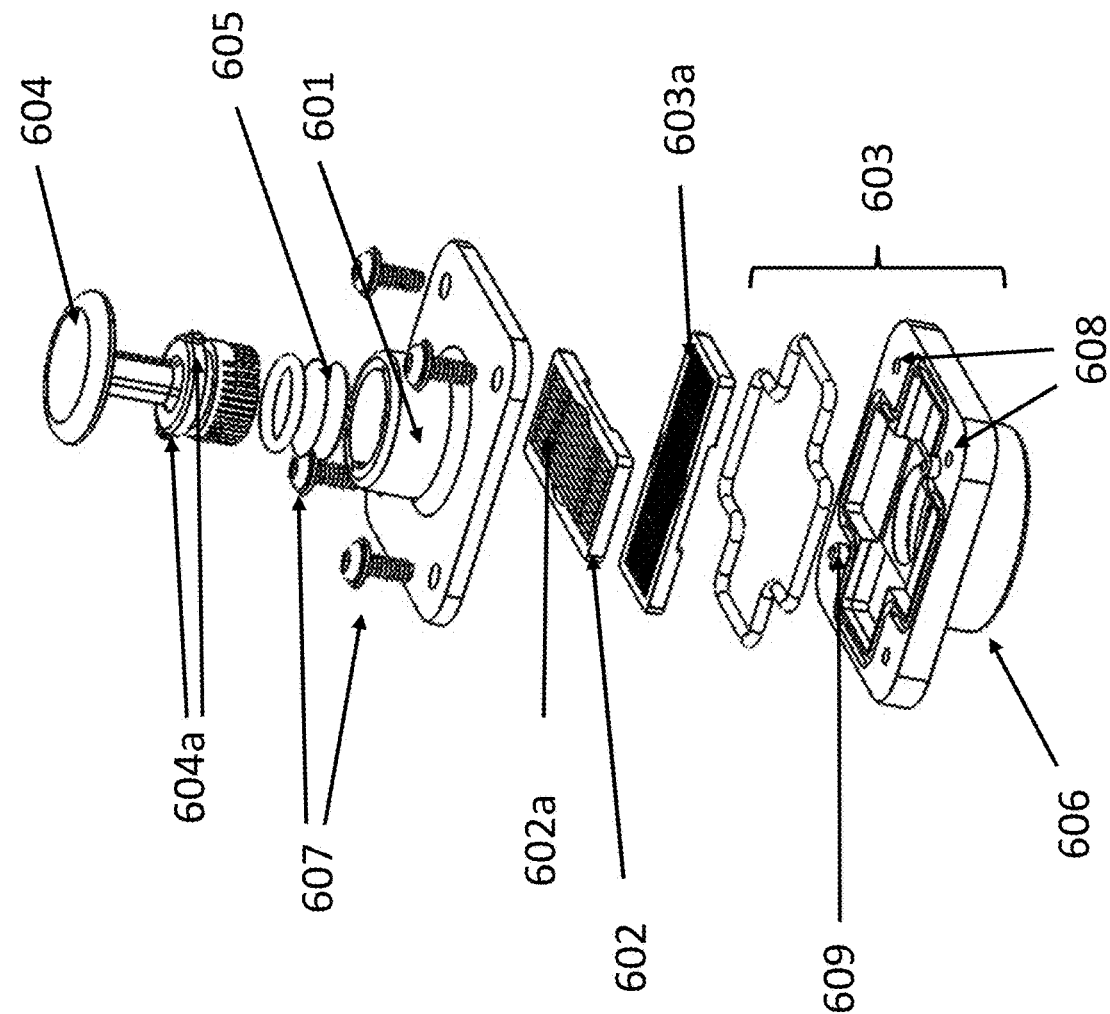
FIG. 6 depicts a tissue dissociator according to another embodiment of the present disclosure.

FIG. 6 depicts a tissue dissociator according to another embodiment of the present disclosure. Tissue dissociator 600 includes sample holder and cap 601, cutting blade holder 602 with cap cutting blades 602a, mount 603 with mount cutting blades 603a and tissue actuator 604 with distal end pliable stopper 605. Distal end pliable stopper is attached to the tissue actuator with an adhesive, in some instances with an O-ring (e.g., to provide a fluidic seal). Tissue actuator 604 includes protrusions 604a for maintaining alignment during displacement in sample holder and cap 601. Cutting blade holder 602 is recessed into mount 603. Mount 603 includes a blade holder for positioning mount cutting blade 603a as well as connector 606 configured for coupling tissue dissociator 600 to a container. Connector 606 is configured to connect mount 603 to a container (e.g., conical tube, falcon tube, etc.) Mount 603 includes alignment protrusions 609 that couples with holes (not shown) on sample holder 601 to maintain alignment of sample holder and cap 601, cutting blade holder 602 and mount 603. Sample holder and cap 601 is fastened to cutting blade holder 602 and mount 603 with screws 607 through holes 608 in each component.

Figure 7:
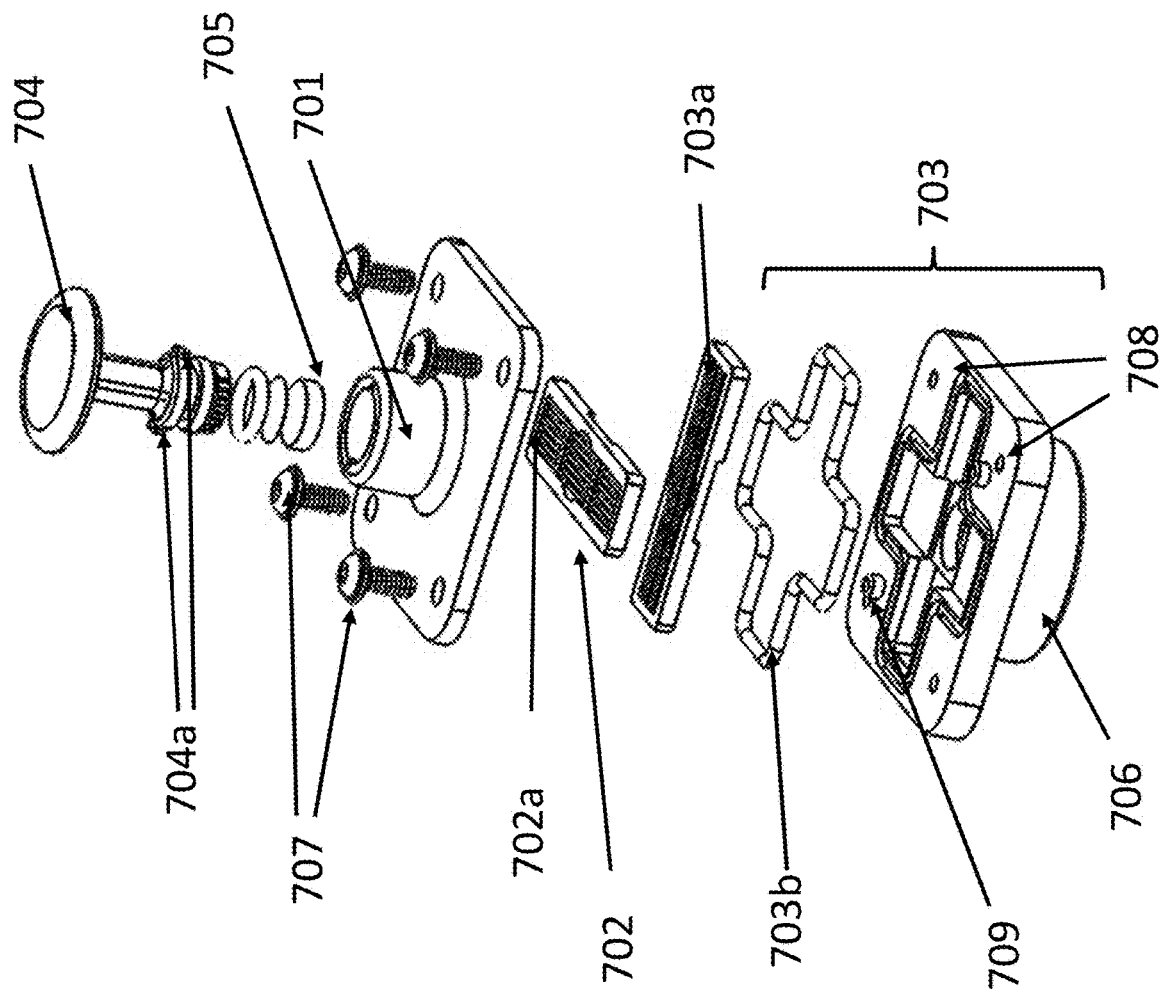
FIG. 7 depicts a tissue dissociator according to another embodiment of the present disclosure.

FIG. 7 depicts a tissue dissociator according to another embodiment of the present disclosure. Tissue dissociator 700 includes sample holder and cap 701, cutting blade holder 702 with cap cutting blades 702a, mount 703 with mount cutting blades 703a and tissue actuator 704 with distal end pliable stopper 705. Distal end pliable stopper is attached to the tissue actuator with an adhesive, in some instances with an O-ring (e.g., to provide a fluidic seal). Mount 703 includes a blade holder for positioning mount cutting blade 703a and insert o-ring 703b for securing and forming a fluidic seal for both cutting blade 702, cutting blades 702a and mount cutting blades 703a with mount 703. Mount 703 is configured with connector 706 for coupling tissue dissociator 700 to a container. Connector 706 is configured to connect mount 703 to a container (e.g., conical tube, falcon tube, etc.) Sample holder and cap 701 is fastened to cutting blades 702 and mount 703 with screws 707 through holes 708 in each component. To maintain alignment, mount 703 includes alignment protrusions 709 that are complimentary to holes (not shown) on sample holder 701. Tissue actuator 704 includes protrusions 704a for maintaining alignment during displacement in sample holder 701. The distal end of tissue actuator 704 has a circular cross-section that is smaller than the cross-section of the distal end of tissue actuator 604 in FIG. 6. In addition, the pliable stopper in FIG. 7 is thicker than that in FIG. 6.

Figure 8:
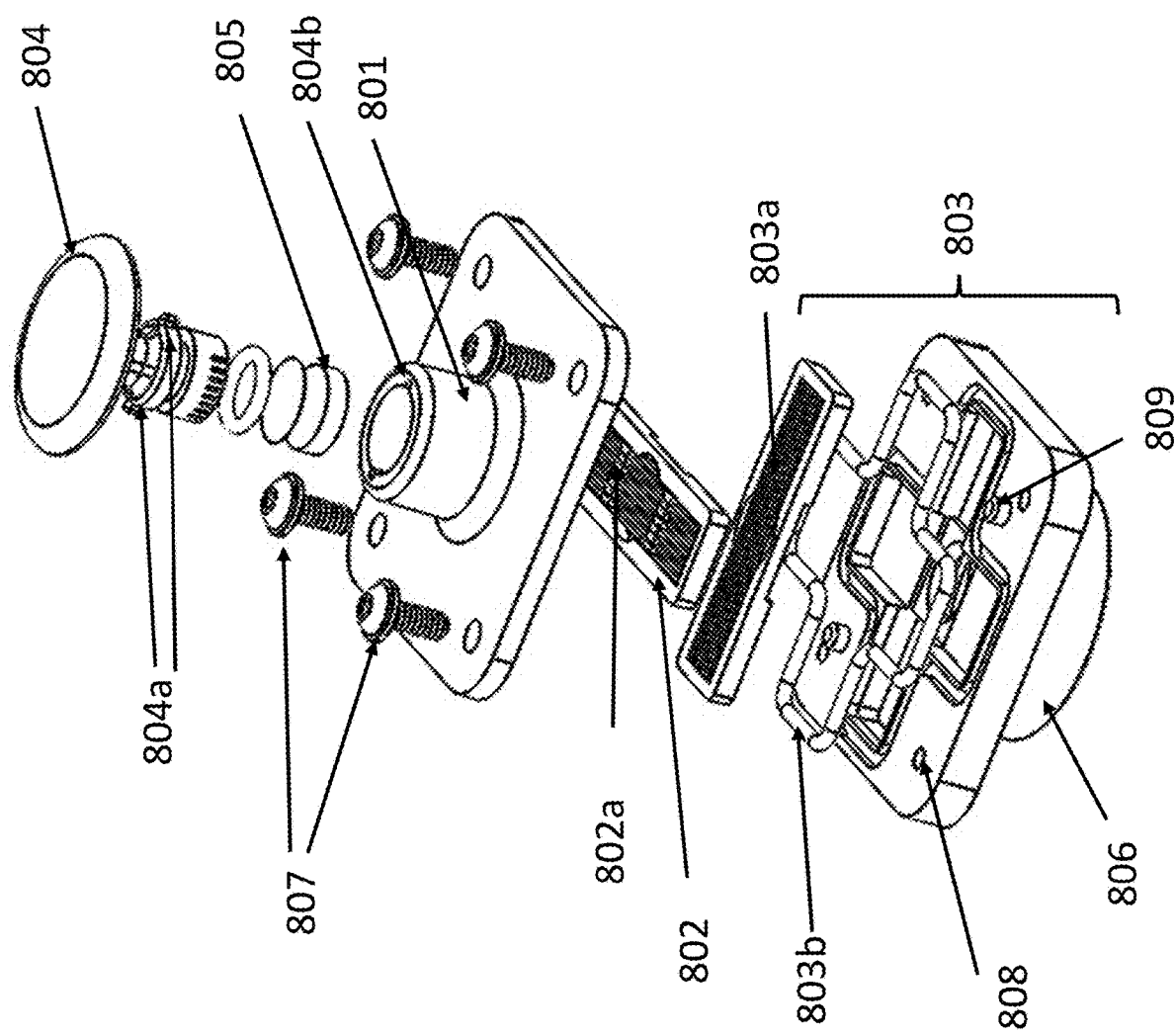
FIG. 8 depicts a tissue dissociator according to another embodiment of the present disclosure.

FIG. 8 depicts a tissue dissociator according to another embodiment of the present disclosure. Tissue dissociator 800 includes sample holder and cap 801, cutting blade holder 802 with cap cutting blades 802a, mount 803 with mount cutting blades 803a and tissue actuator 804 with distal end pliable stopper 805. Distal end pliable stopper is attached to the tissue actuator with an adhesive, in some instances with an O-ring (e.g., to provide a fluidic seal). Mount 803 includes a blade holder for positioning mount cutting blade 803a and insert 803b for securing both cutting blade holder 802, cap cutting blades 802a and mount cutting blades 803a with mount 803. Mount 803 is configured with connector 806 for coupling tissue dissociator 800 to a container. Connector 806 is configured to connect mount 803 to a container (e.g., conical tube, falcon tube, etc.) Sample holder and cap 801 is fastened to cutting blade holder 802 and mount 803 with screws 807 through holes 808 in each component. To maintain alignment, mount 803 includes alignment protrusions 809 that are complimentary to holes (not shown) on sample holder 801. Tissue actuator 804 includes protrusions 804a for maintaining alignment during displacement in sample holder 801. Sample holder 801 includes grooves 804b which maintain alignment with protrusions 804a on tissue actuator 804 during displacement. In this embodiment, tissue actuator 804 has a shorter longitudinal length and a distal end having a larger diameter than tissue actuator 704 in FIG. 7.

Figure 9:
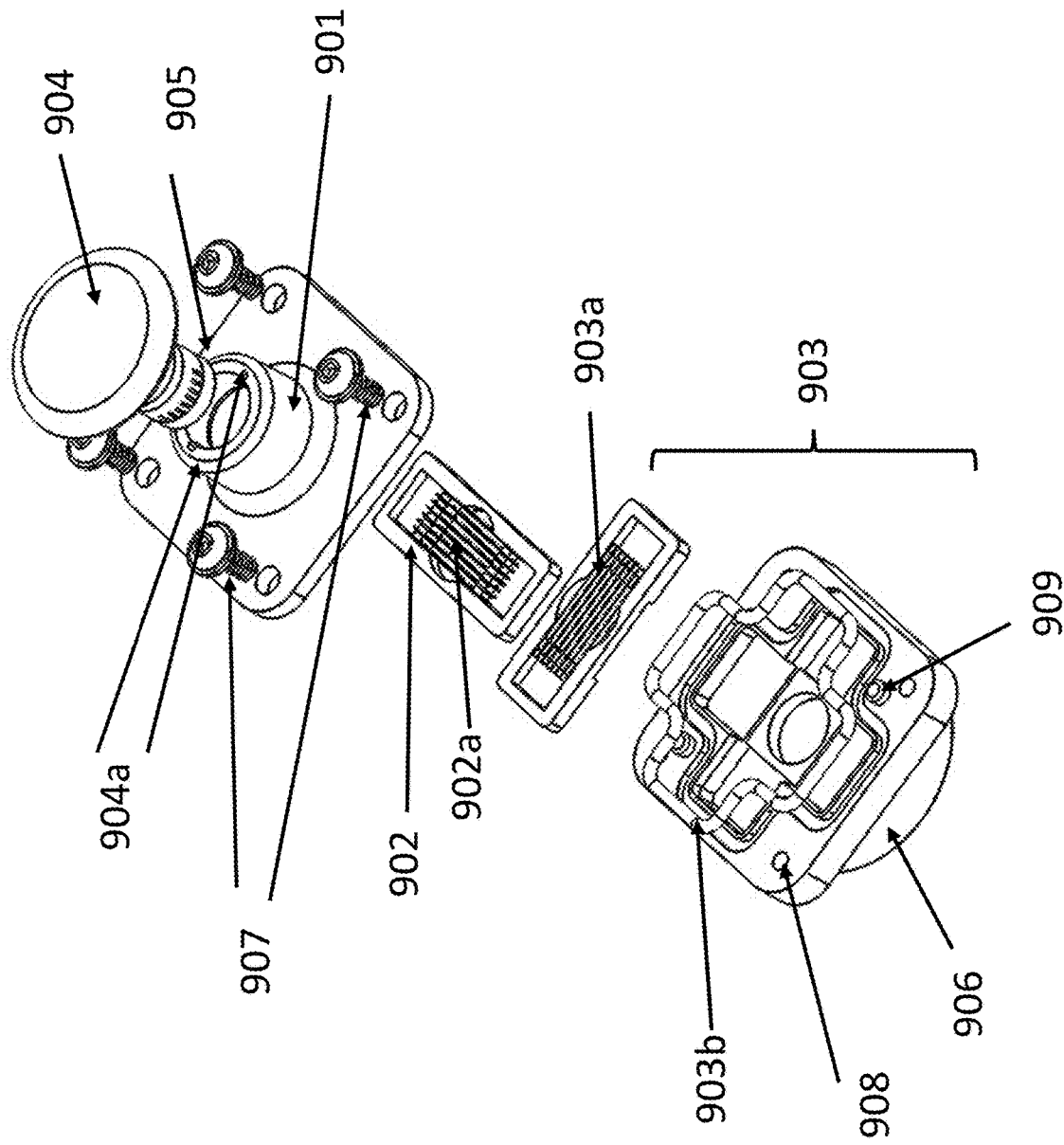
FIG. 9 depicts a top view of a tissue dissociator according to another embodiment of the present disclosure.

FIG. 9 depicts a top view of a tissue dissociator according to another embodiment of the present disclosure. Tissue dissociator 900 includes sample holder and cap 901, cutting blade holder 902 with cap cutting blades 902a, mount 903 with mount cutting blades 903a and tissue actuator 904 with distal end pliable stopper 905. Mount 903 includes a blade holder for positioning mount cutting blade 903a and insert 903b for securing both cutting blade holder 902, cap cutting blades 902a and mount cutting blades 903a with mount 903. Mount 903 is configured with connector 906 for coupling tissue dissociator 900 to a container. Sample holder and cap 901 is fastened to cutting blade holder 902 and mount 903 with screws 907 through holes 908 in each component. To maintain alignment, mount 903 includes alignment protrusions 909 that are complimentary to holes (not shown) on sample holder and cap 901. Sample holder and cap 901 includes grooves 904a which maintain alignment with protrusions (not shown) on tissue actuator 904 during displacement. Protrusions on tissue actuator 904 also include tabs that provide feedback at the distal end of grooves 904a indicating that the tissue actuator has reached the distal end of sample holder and cap 901 or that the cutting stroke is complete. In this embodiment, cap cutting blades 902a and mount cutting blades 903a are shorter than the blades 702a and 703a in tissue actuator 704a in FIG. 7 and the blades 802a and 803a in tissue actuator 804a in FIG. 8.

Figure 10:
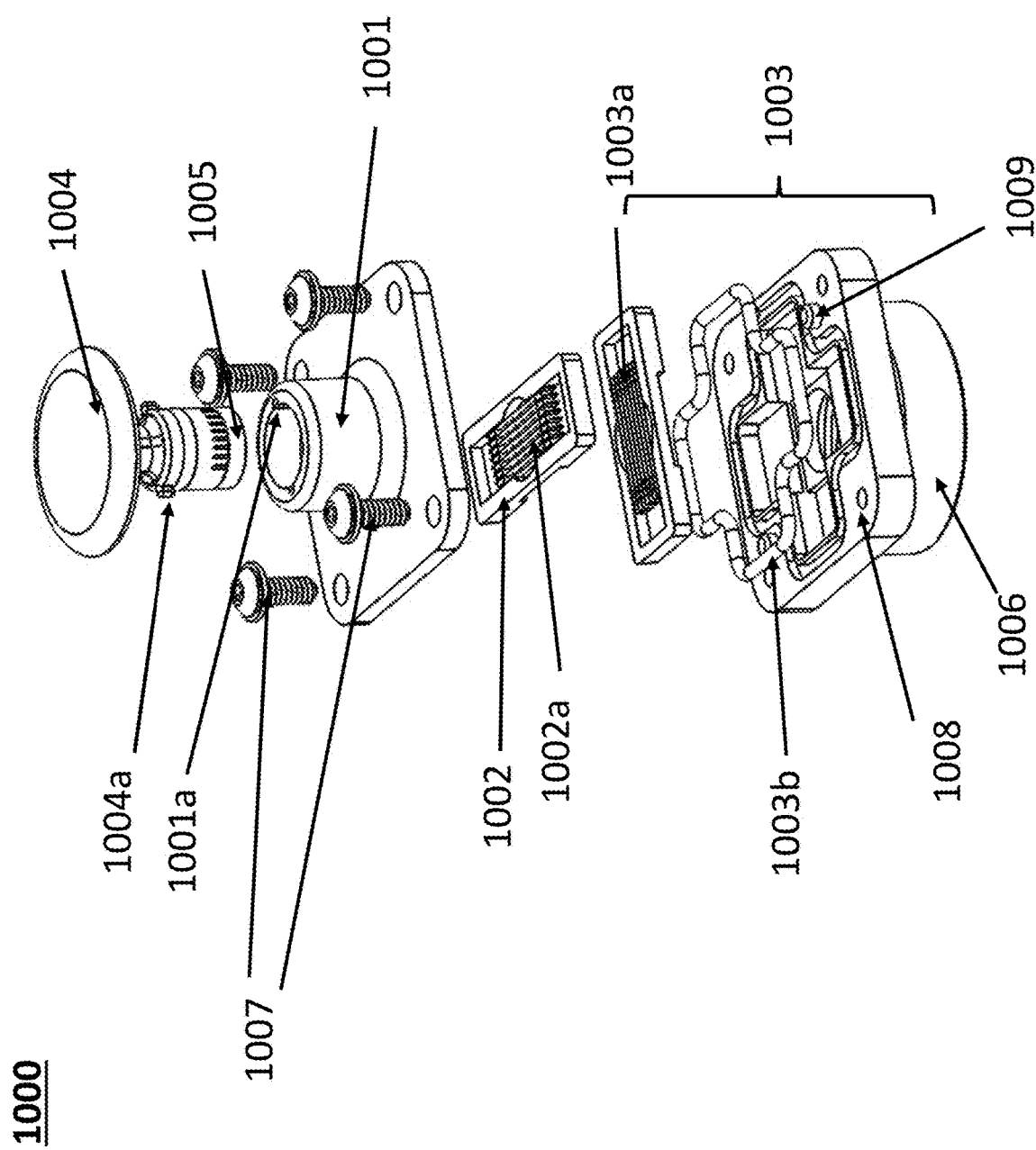
FIG. 10 depicts a tissue dissociator according to another embodiment of the present disclosure.

FIG. 10 depicts a tissue dissociator according to another embodiment of the present disclosure. Tissue dissociator 1000 includes sample holder and cap 1001, cutting blade holder 1002 with cap cutting blades 1002a, mount 1003 with mount cutting blades 1003a and tissue actuator 1004 with distal end pliable stopper 1005. Mount 1003 includes a blade holder for positioning mount cutting blade 1003a and insert 1003b for securing both cutting blade holder 1002, cap cutting blades 1002a and mount cutting blades 1003a with mount 1003. Mount 1003 is configured with connector 1006 for coupling tissue dissociator 1000 to a container. Sample holder and cap 1001 is fastened to cutting blade holder 1002 and mount 1003 with screws 1007 through holes 1008 in each component. Tissue actuator 1004 includes protrusions 1004a which couple with grooves 1001a on sample holder 1001 to maintain alignment during tissue dissociation. Protrusions 1004a provide audible or tactile feedback when tissue actuator 1004 has reached a predetermined distance along the longitudinal axis of sample holder and cap 1001 in grooves 1001a. This audible or tactile feedback can also indicate that the cutting motion is complete and the tissue is dissociated through one or more of cutting blades 1002a and 1003a. To maintain alignment, mount 1003 includes alignment protrusions 1009 that are complimentary to holes (not shown) on sample holder and cap 1001.

Figure 11:
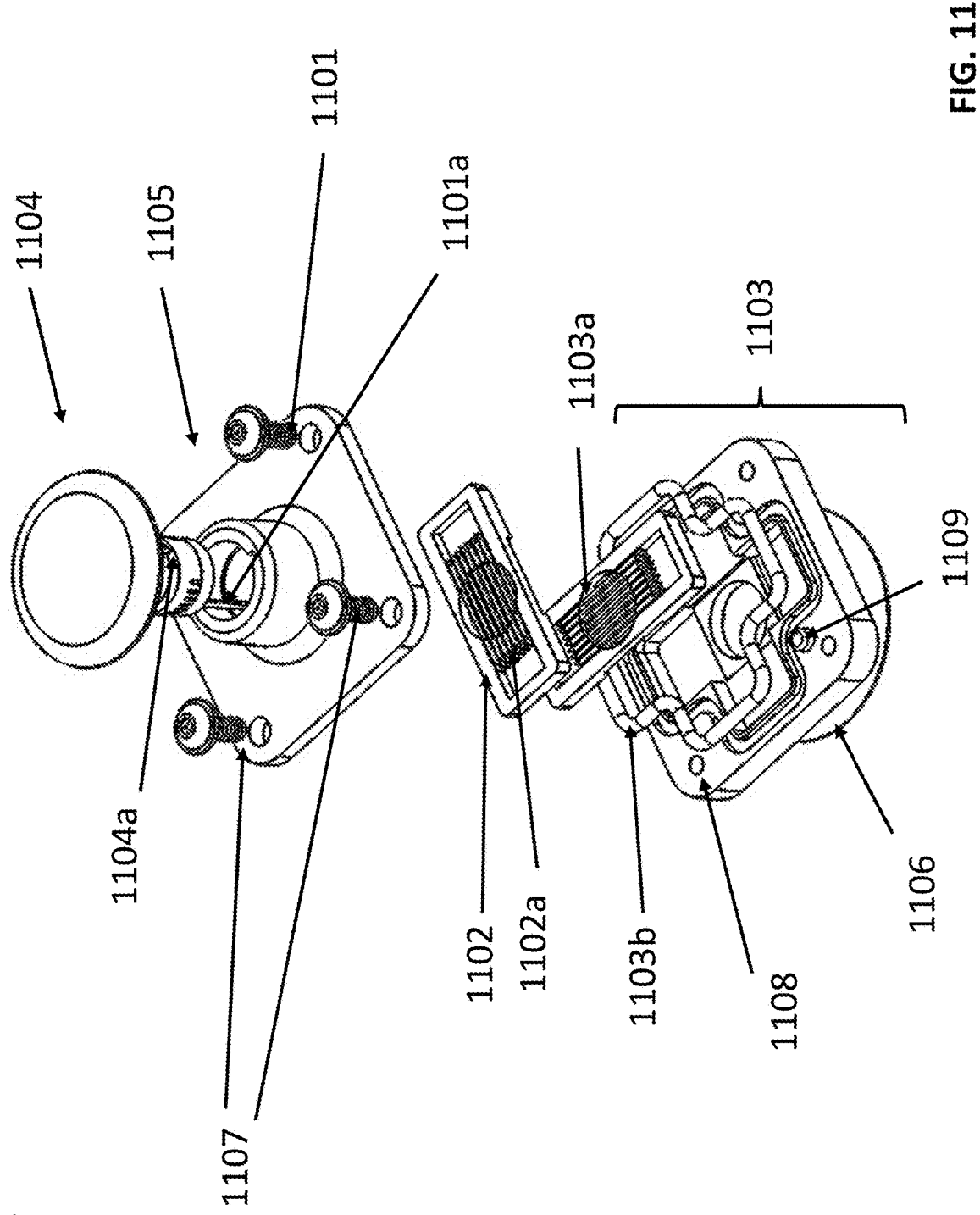
FIG. 11 depicts a top view of a tissue dissociator according to another embodiment of the present disclosure.

FIG. 11 depicts a top view of a tissue dissociator according to another embodiment of the present disclosure. Tissue dissociator 1100 includes sample holder and cap 1101, cutting blade holder 1102 with cap cutting blades 1102a, mount 1103 with mount cutting blades 1103a and tissue actuator 1104 with distal end pliable stopper 1105. Tissue actuator 1104 includes protrusions 1104a which couple with grooves 1101a on sample holder and cap 1101 to maintain alignment during tissue dissociation. Protrusions 1104a provide audible or tactile feedback when tissue actuator 1104 has reached a predetermined distance along the longitudinal axis of sample holder and cap 1101 in grooves 1101a or to indicate that a cutting motion is complete. Mount 1103 includes a blade holder for positioning mount cutting blade 1103a and insert 1103b for securing both cutting blade holder 1102, cap cutting blades 1102a and mount cutting blades 1103a with mount 1103. Mount 1103 is configured with connector 1106 for coupling tissue dissociator 1100 to a container. Sample holder and cap 1101 is fastened to cutting blade holder 1102 and mount 1103 with screws 1107 through holes 1108 in each component. To maintain alignment, mount 1103 includes alignment protrusions 1109 that are complimentary to holes (not shown) on sample holder and cap 1101.

Figure 12:
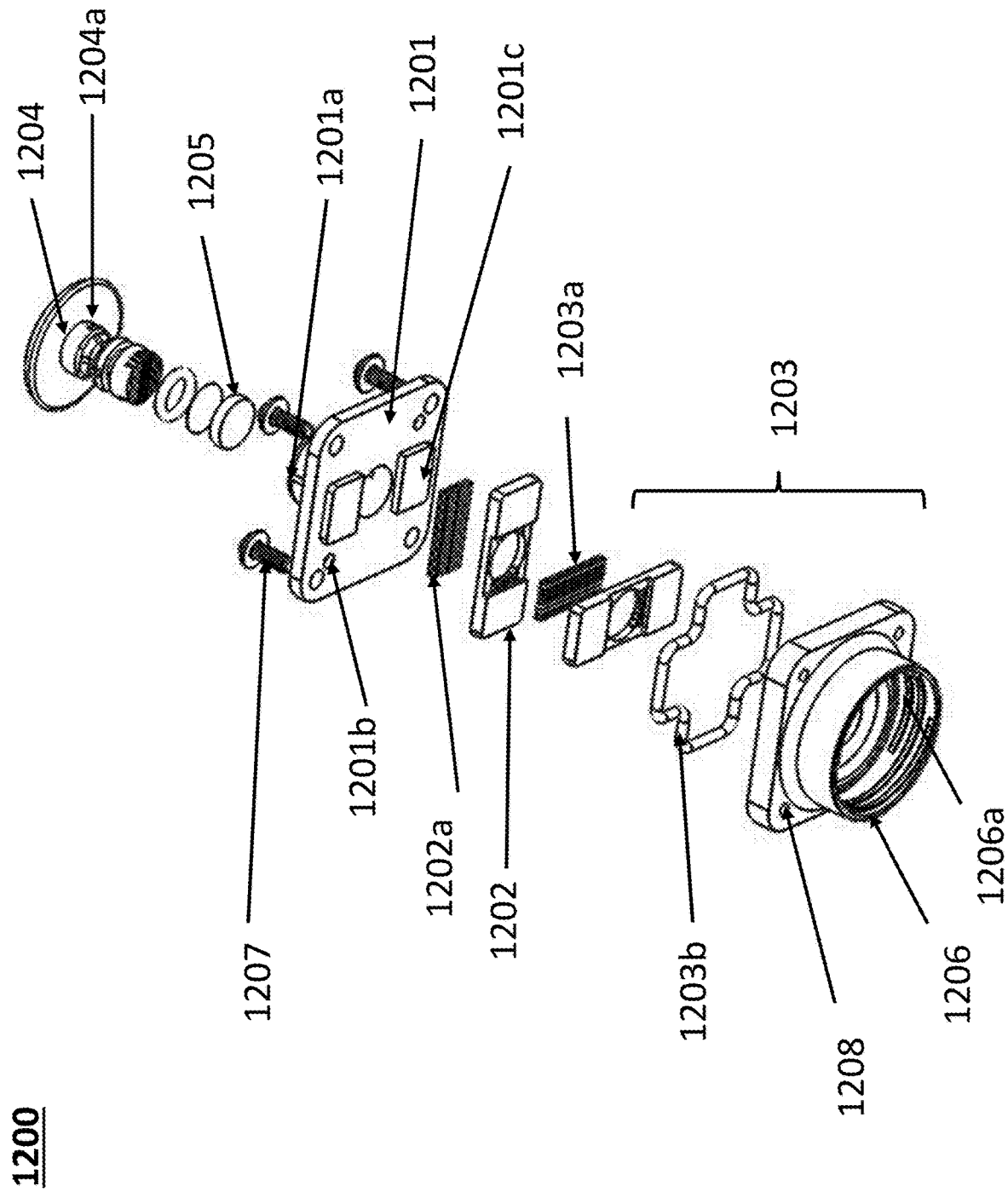
FIG. 12 depicts a bottom view of a tissue dissociator according to another embodiment of the present disclosure.

FIG. 12 depicts a bottom view of a tissue dissociator according to another embodiment of the present disclosure. Tissue dissociator 1200 includes sample holder and cap 1201, cutting blade holder 1202 with cap cutting blades 1202a, mount 1203 with mount cutting blades 1203a and tissue actuator 1204 with distal end pliable stopper 1205. Distal end pliable stopper is attached to the tissue actuator with an adhesive, in some instances with an O-ring (e.g., to provide a fluidic seal). Tissue actuator 1204 includes protrusions 1204a which couple with grooves 1201a on sample holder and cap 1201 to maintain alignment during tissue dissociation. Two tabs 1204a are also present on tissue actuator 1204 to provide audible or tactile feedback indicating that tissue actuator 1204 has reached a predetermined distance along the longitudinal axis of sample holder and cap 1201 or to indicate that a cutting motion is complete. Sample holder and cap 1201 includes holes 1201b for maintaining alignment between sample holder 1201, cutting blade holder 1202 and mount 1203. Holes 1201b are complimentary to protrusions (not shown) on mount 1203. Sample holder and cap 1201 also includes protrusions 1201c which contact the blade holder of mount 1203 and press fit with cutting blade holder 1202 to secure each component together. Sample holder and 1201 is fastened to cutting blade holder 1202 and mount 1203 with screws 1207 through holes 1208 on mount 1203. Mount 1203 includes a blade holder for positioning mount cutting blade 1203a and insert 1203b for securing both cutting blade holder 1202, cap cutting blades 1202a and mount cutting blades 1203a with mount 1203. Mount 1203 is configured with connector 1206 for coupling tissue dissociator 1200 to a container. Connector 1206 includes an internal screw thread 1206a for connecting mount 1203 to a container by screw threading with the top of the container (e.g., screw-threaded falcon tube).

Methods for Dissociating a Biological Tissue Sample

Aspects of the disclosure also include methods for dissociating a biological tissue sample. Methods according to certain embodiments include: 1) inserting a biological tissue into the sample holder of a tissue dissociator where the tissue dissociator includes a blade holder having a blade and a sample holder having a tissue actuator with a distal end pliable stopper where the tissue actuator is configured to be displaced along a longitudinal axis within the sample holder; and 2) pressing the biological tissue against the cutting blades by displacing the tissue actuator from the proximal end of the sample holder to the distal end of the sample holder in a manner sufficient dissociate the biological tissue and cut the pliable stopper with at least one of the cutting blades.

In embodiments of the present disclosure, the biological tissue sample may be a whole organism, plant, fungi or a subset of tissues or component parts of the organism. Biological tissue samples may be obtained from an in vitro source (e.g., tissue grown in laboratory culture) or from an in vivo source (e.g., a mammalian subject, a human subject, etc.). In some embodiments, the tissue sample is obtained from an in vitro source. In some embodiments, the tissue sample is obtained from an in vivo source, where in some instances, tissues derived from a subject are cultured, stored, or manipulated prior to evaluation. In vivo sources include living multi-cellular organisms and can yield non-diagnostic or diagnostic tissue samples. In still other embodiments, the tissue sample is a patient derived xenograph, such as a human tissue (e.g., tumor tissue) grown in a different host animal (e.g., mouse, rat, rabbit, etc.)

In certain embodiments the source of the tissue sample is a "mammal" or "mammalian", where these terms are used broadly to describe organisms which are within the class Mammalia, including the orders Carnivore (e.g., dogs and cats), Rodentia (e.g., mice, guinea pigs, and rats), and Primates (e.g., humans, chimpanzees, and monkeys). In some instances, the subjects are humans. Biological tissue samples may include tissue from human subjects of both genders and at any stage of development (i.e., neonates, infant, juvenile, adolescent, adult), where in certain embodiments the human subject is a juvenile, adolescent or adult. While the present disclosure may be applied to samples from a human subject, it is to be understood that the methods may also be carried out on samples from other animal subjects (that is, in "non-human subjects") such as, but not limited to, birds, mice, rats, dogs, cats, livestock and horses.

In some embodiments, methods include dissociating tissue from a component part of a human subject, such as organs including but not limited to integumentary tissue (e.g. sections of the skin), oral tissue (e.g., buccal, tongue, palatal, gums), respiratory tissue (e.g., pharynx, larynx, trachea, bronchi, lungs, diaphragm) gastrointestinal tissue (e.g., esophagus, stomach, liver, gallbladder, pancreas, intestines, colon, rectum and anus), cardiovascular tissue (e.g., heart, blood vessels), endocrine tissue (e.g., hypothalamus, pituitary gland, pineal body or pineal gland, thyroid, parathyroids, adrenal glands) and genitourinary tissue (kidneys, ureters, bladder, urethra, ovaries, fallopian tubes, uterus, vagina, mammary glands, testes, vas deferens, seminal vesicles, prostate, penis), muscular tissue, nervous tissue (e.g., brain, spinal cord, nerves) as well as soft skeletal tissue (cartilage, ligaments, tendons). Biological samples may be any type of organismic tissue, including both healthy and diseased tissue (e.g., cancerous, malignant, necrotic, etc.)

The size of tissue dissociated by the subject methods may vary, depending on the type and source of tissue as well as the tissue dissociator employed. For example, the length of biological tissue samples may range may range from 0.01 cm to 5 cm, such as from 0.02 cm to 4.5 cm, such as from 0.03 cm to 4 cm, such as from 0.04 cm to 3.5 cm, such as from 0.05 cm to 3 cm, such as from 0.06 cm to 2.5 cm, such as from 0.07 cm to 2 cm, such as from 0.08 cm to 1.5 cm, such as from 0.09 cm to 1 cm and including from 0.1 cm to 0.5 cm. The width of the biological sample may range from 0.01 cm to 5 cm, such as from 0.02 cm to 4.5 cm, such as from 0.03 cm to 4 cm, such as from 0.04 cm to 3.5 cm, such as from 0.05 cm to 3 cm, such as from 0.06 cm to 2.5 cm, such as from 0.07 cm to 2 cm, such as from 0.08 cm to 1.5 cm, such as from 0.09 cm to 1 cm and including from 0.1 cm to 0.5 cm. The thickness of biological tissue samples may also vary, ranging from 0.001 mm to 50 mm, such as from 0.002 mm to 25 mm, such as from 0.003 mm to 22.5 mm, such as from 0.004 mm to 20 mm, such as from 0.005 mm to 15 mm, such as from 0.005 mm to 12.5 mm and including from 0.01 mm to 10 mm. such as from 0.05 mm to 10 mm and including from 0.1 mm to 5 mm. For example, tissue dissociator devices of interest may be configured to dissociate biological tissue samples having a surface area ranging from 0.001 to 100 $cm^2$, such as from 0.05 to 100 $cm^2$, 0.01 to 100 $cm^2$, such as 0.05 to 50 $cm^2$, such as 0.1 to 25 $cm^2$, such as 0.5 to 15 $cm^2$, such as 0.75 to 10 $cm^2$, such as 1 to 7.5 $cm^2$, and including 2 to 5 $cm^2$. In some embodiments, methods include dissociating biological tissue samples having a volume ranging from 0.001 to 10 $cm^3$, such as from 0.005 to 9 $cm^3$, such as from 0.0075 to 8 $cm^3$, such as from 0.01 to 7 $cm^3$, such as 0.02 to 6 $cm^3$, such as 0.05 to 5 $cm^3$, such as 0.1 to 4 $cm^3$, such as 0.5 to 3 $cm^3$, and including 0.75 to 2 $cm^3$.

In practicing the subject methods tissue is pressed into contact and through the cutting blades at the distal end of the tissue actuator. In certain embodiments, the tissue actuator is displaced in a manner sufficient to press the pliable stopper through one or more of the cutting blades. For example, in one instance, methods include displacing the tissue actuator to dissociate the tissue sample and to press the pliable stopper through the cap cutting blades. In other instances, methods include displacing the tissue actuator to dissociate the tissue sample and to press the pliable stopper through the cap cutting blades and the mount cutting blades. In some cases pressing the pliable stopper through the cutting blades is sufficient to cut the pliable stopper. Depending on the thickness of the distal end pliable stopper, the tissue actuator may be displaced such that 10% or more of the distal end pliable stopper is pressed through the cutting blades, such as 15% or more, such as 25% or more, such as 50% or more, such as 75% or more, such as 90% or more, such as 95% or more, such as 97% or more and including 99% or more of the distal end pliable stopper. In certain embodiments, the tissue actuator is displaced such that the entire distal end pliable stopper is pressed through the cutting blades (i.e., the blades cut completely (100%) through the pliable stopper) and contact the tissue actuator.

In some embodiments, the pliable stopper contacts the side edges (i.e., are flush) of the cutting blades when displacing the tissue actuator and pressing the pliable stopper through the cutting blades. In certain instances, the pliable stopper forms a fluidic seal with the side edges of the cutting blade as the pliable stopper is pressed through the cutting blade. In these embodiments, methods include removing (i.e., pressing through the cutting blades) remaining tissue or fluid from the dissociated biological tissue sample on the cutting blades.

In embodiments, methods include pressing the pliable stopper through the cutting blades in a manner such that little to no tissue or fluid from the dissociated biological tissue sample remains on the cutting blades, such as 50% by weight or less of the total amount of biological tissue being dissociated, such as 45% by weight or less, such as 40% by weight or less, such as 35% by weight or less, such as 30% by weight or less, such as 25% by weight or less, such as 20% by weight or less, such as 15% by weight or less, such as 10% by weight or less, such as 9% by weight or less, such as 8% by weight or less, such as 7% by weight or less, such as 6% by weight or less, such as 5% by weight or less, such as 4% by weight or less, such as 3% by weight or less, such as 2% by weight or less, such as 1% by weight or less, such as 0.5% by weight or less, such as 0.1% by weight or less, such as 0.01% by weight or less, such as 0.001% by weight or less and including 0.0001% by weight or less of the total amount of biological tissue being dissociated remains on the cutting blades after the pliable stopper is pressed through the cutting blades. In certain embodiments, methods include pressing the pliable stopper through the cutting blades leaving no biological tissue on the cutting blades.

As described above, a biological tissue sample is inserted into the sample holder of the tissue dissociator and the biological tissue sample is displaced along a longitudinal axis within the inner chamber of the housing with a tissue actuator and contacted with cutting blades of the blade holder. The tissue actuator may be displaced along all or part of the length inner chamber of the sample to dissociate the biological tissue sample. For example, the tissue actuator may be displaced along 25% or more of the length of the housing to dissociate the biological tissue sample, such as 35% or more, such as 50% or more, such as 60% or more, such as 75% or more, such as 90% or more, such as 95% or more, such as 97% or more and including 99% or more of the length of the housing. In certain embodiments, the tissue actuator is displaced along the entire (i.e., 100%) length of the sample holder to dissociate the biological tissue sample.

The tissue actuator may be displaced continuously or in discrete increments. In some embodiments, the tissue actuator is displaced continuously. In other embodiments, the tissue actuator is displaced in one or more discrete increments, such as in 2 or more discrete increments, such as 3 or more, such as 4 or more, such as 5 or more, such as 10 or more and including in 25 or more discrete increments. Depending on the size of the tissue dissociator sample holder as well as the type of biological tissue sample, each discrete increment may vary in length. For example, each discrete increment may be 1 mm or more, such as 2 mm or more, such as 5 mm or more, such as 10 mm or more, such as 25 mm or more and including 50 mm or more.

In certain embodiments, tissue actuator is displaced in a back-and-forth motion along a longitudinal axis within the sample holder, such as moving from a distal part to a proximal part of the housing and back from the proximal part to the distal part of the sample holder. In some instances, tissue actuator is displaced in a back-and-forth motion along only a portion of the inner chamber of the sample. For example, the tissue actuator is displaced in a back-and-forth motion along 99% or less of the length of the inner chamber of the sample holder, such as 95% or less, such as 90% or less, such as 85% or less, such as 80% or less, such as 75% or less, such as 70% or less, such as 65% or more, including displacing the tissue actuator in a back-and-forth motion along 50% or less of the length of the inner chamber of the sample holder. Where the tissue actuator is moved in a back-and-forth motion, the movement of the tissue actuator may be repeated one or more times to dissociate the biological tissue sample as desired, such as 2 or more times, such as 5 or more times, such as 10 or more times, such as 15 or more times and including 25 or more times.

Depending on the type of biological tissue sample and size of tissue dissociator employed, the rate that the tissue actuator is displaced may vary. For example, the tissue actuator may be displaced within the housing at a rate of 1 mm/second or more, such as 2 mm/second or more, such as 3 mm/second or more, such as 5 mm/second or more, such as 10 mm/second or more and including displacing the tissue actuator at a rate of 25 mm/second or more.

In embodiments, tissue dissociation can be carried out at any suitable temperature so long as the viability of the biological tissue sample and dissociated tissue fragments are preserved as desired. As such, the temperature according to embodiments of the disclosure may vary, such as from 0° C. to 100° C., such as from 0° C. to 75° C., such as from 0° C. to 50° C., such as from 0° C. to 25° C., such as from 0° C. to 10° C., and including from 0° C. to 37° C., such as from 18° C. to 25° C.

In certain embodiments, methods further include coupling the subject tissue dissociator to a container and dissociating the biological tissue sample into the coupled container. In some instances, methods include connecting the container to the blade holder. In other instances, methods include connecting the container to the sample holder. In yet other instances, the sample holder and the cap component of the blade holder are a single integrated unit and methods include connecting the container to the integrated sample holder cap component. The container may be coupled to the tissue dissociator by any convenient fastener, such as with a latch, notch, groove, pin, tether, hinge, non-permanent adhesive or a combination thereof. In certain instances, the inner wall of the cap is threaded and methods include screw threading the container to the cap. As described above, containers of interest may vary, including but are not limited to a test tube, centrifuge tube, culture tube, falcon tube, microtube, Eppendorf tube, specimen collection container, specimen transport container and petri dish.

In some embodiments, the container contains an amount of a fluidic composition and the biological tissue sample is dissociated into the fluidic composition. In certain embodiments, the fluidic composition is a buffer. Example buffers may include but are not limited to PBS (phosphate) buffer, acetate buffer, N,N-bis(2-hydroxyethyl)glycine (Bicine) buffer, 3-{[tris(hydroxymethyl)methyl]amino}propanesulfonic acid (TAPS) buffer, 2-(N-morpholino)ethanesulfonic acid (MES) buffer, citrate buffer, tris(hydroxymethyl)methylamine (Tris) buffer, N-tris(hydroxymethyl)methylglycine (Tricine) buffer, 3-[N-Tris(hydroxymethyl)methylamino]-2-hydroxypropanesulfonic Acid (TAPSO) buffer, 4-2-hydroxyethyl-1-piperazineethanesulfonic acid (HEPES) buffer, 2-{[tris(hydroxymethyl)methyl]amino}ethanesulfonic acid (TES) buffer, piperazine-N,N'-bis(2-ethanesulfonic acid) (PIPES) buffer, dimethylarsinic acid (Cacodylate) buffer, saline sodium citrate (SSC) buffer, 2(R)-2-(methylamino)succinic acid (succinic acid) buffer, potassium phosphate buffer, N-Cyclohexyl-2-aminoethanesulfonic acid (CHES) buffer, among other types of buffered solutions. Depending on the size of the container and the biological tissue dissociated, the amount of fluidic composition (e.g., buffer) in the container may vary, ranging from 1 mL to 500 mL, such as from 2 mL to 450 mL, such as from 3 mL to 400 mL, such as from 4 mL to 350 mL, such as from 5 mL to 300 mL, such as from 6 mL to 250 mL, such as from 7 mL to 200 mL, such as from 8 mL to 150 mL and including from 9 mL to 100 mL.

In some embodiments, the fluidic composition includes a digestive enzyme. The term "digestive enzyme" is used herein in its conventional sense to refer to enzymes which break down macromolecules (e.g., biomolecules) such as proteins, lipids, nucleic acids and polysaccharides. As such, digestive enzymes of interest include proteolytic enzymes, lipolytic enzymes, amylolytic enzymes and nucleolytic enzymes. Example digestive enzyme may include, but are not limited to ptyalin, amylase, betaine, bromelain, pepsin, gastric amylase, gelatinase, rennin, gastric lipase, pancreatic lipase, phospholipase, trypsin, steapsin, chymotrypsin, collagenase, hyaluroidase, carboxypeptidase, pancreatic amylase, elastases, nucleases, DNase I, sucrase, maltase, lactase, isomaltase, papin, dispase and deoxyribonuclease, neutral protease, pronase, among other digestive enzymes. The amount of digestive enzyme present in the subject compositions may vary depending on the type of biological tissue dissociated and macromolecule breakdown desired and may be $10^2$ enzyme units or greater, such as $10^3$ enzyme units or greater, such as $10^4$ enzyme units or greater, such as $10^5$ enzyme units or greater, such as $10^6$ enzyme units or greater, such as $10^7$ enzyme units or greater, such as $10^8$ enzyme units or greater, such as $10^9$ enzyme units or greater and including $10^{10}$ enzyme units or greater. In these embodiments, the amount of fluidic composition containing digestive enzyme in the container may vary, ranging from 1 mL to 500 mL, such as from 2 mL to 450 mL, such as from 3 mL to 400 mL, such as from 4 mL to 350 mL, such as from 5 mL to 300 mL, such as from 6 mL to 250 mL, such as from 7 mL to 200 mL, such as from 8 mL to 150 mL and including from 9 mL to 100 mL.

In certain embodiments, methods include dissociating a biological tissue sample by displacing the tissue actuator to press the tissue through the cutting blades and agitating (e.g., rocking, shaking, vortexing, etc.) the container to rinse the cutting blades with a fluidic composition, such as a buffer solution. By agitating the container, the fluidic composition (e.g., buffer solution) rinses the cutting blades and may remove any remaining tissue sample from the cutting blades. In certain embodiments, the pliable stopper may be pressed through the cutting blades and shaking the container with the fluidic composition is sufficient to rinse the pliable stopper of remaining tissue sample from the cutting blades and pliable stopper. The container is agitated for an amount of time sufficient to rinse the cutting blades and pliable stopper, such as from 3 seconds or longer, such as 5 seconds or longer, such as 10 seconds or longer, such as 15 seconds or longer, such as 30 seconds or longer, such as 45 seconds or longer, such as 60 seconds or longer, such as 2 minutes or longer, such as 3 minutes or longer, such as 5 minutes or longer and including agitating the container for 10 minutes or longer. The container may be agitated one or more times as necessary, such as two or more times, such as three or more times, such as five or more times and including ten or more times.

In certain embodiments, methods also include monitoring the plurality tissue fragments produced while dissociating the biological tissue sample. Monitoring dissociation of the biological tissue sample may include assessing the produced plurality of tissue fragments. For example, monitoring dissociation of the biological tissue sample may include evaluating the homogeneity of sizes of the produced tissue fragments. Monitoring dissociation of the biological tissue sample may also include evaluating the homogeneity of the shape of the produced tissue fragments. Any convenient protocol may be employed to monitor dissociation of the biological tissue sample, such as by visual inspection (either with the unaided eye, a magnification protocol (e.g., microscope assessment) or with the assistance of a computer utilizing photographic or video protocols)

In some instances, monitoring includes visually inspecting the dissociated tissue fragments in real-time. In other instances, monitoring includes assessing the dissociated tissue fragments at regular intervals, such as every 0.01 minutes, every 0.05 minutes, every 0.1 minutes, every 0.5 minutes, every 1 minute, every 5 minutes or some other interval.

Methods of the present disclosure may also include a step of assessing the dissociated tissue fragments to identify any desired adjustments to the subject protocol. In other words, methods in these embodiments include providing feedback based evaluating the tissue fragments, where adjustments to the protocol may vary in terms of goal, where in some instances the desired adjustment are adjustments that ultimately result in an improved size homogeneity of shape homogeneity of the dissociated tissue fragments.

As described above, the subject tissue dissociators are configured to dissociate a biological tissue sample in a manner sufficient to facilitate the preparation of a single cell composition from the dissociated tissue fragments. In certain embodiments, the methods include assessing the dissociated tissue fragments to determined that the tissue fragments are suitable for further treatment (e.g., with a digestive enzyme) to prepare a single cell composition (e.g., suspension) of the target tissue sample. In some instances, methods include determining that the produced tissue fragments are suitable for further treatment for preparing a single cell composition from the tissue fragments when the dissociated tissue sample has a total cumulative surface area that is 2-fold greater than the undissociated tissue sample, such as 5-fold or greater, such as 10-fold or greater, such as 25-fold or greater, such as 50-fold or greater, such as 100-fold or greater, such as 1000-fold or greater, such as 5000-fold or greater, such as 10,000-folder or greater, such as 100,000-fold or greater and including tissue fragments having a total cumulative surface area that is 1,000,000-fold greater than the undissociated tissue sample. In other instances, methods include determining that the dissociated tissue sample does not contain components of the tissue that would be detrimental or prohibit preparation of a single cell composition from the tissue fragments, such as unwanted connective tissue, adipose tissue or other tissue fragments having an undesired size.

In some embodiments, methods further include preparing a single cell composition (e.g., a single cell suspension) from the tissue fragments. In some instances, preparing a single cell composition includes dissociating a tissue sample as described above and contacting the dissociated tissue fragments with a digestive enzyme composition. In certain instances, the dissociated tissue fragments contacted with the digestive enzyme composition have a cell viability of 75% or greater, such as 80% or greater, such as 85% or greater, such as 90% or greater, such as 95% or greater, such as 97% or greater, such as 99% or greater and including tissue fragments having a cell viability of 99.9% or greater.

Where provided feedback indicates that a particular protocol is less than optimal, such as where dissociated tissue fragments have unsatisfactory size homogeneity, shape homogeneity or surface area, methods may include changing one or more parts of the subject protocols. For example, one or more parameters for pressing the biological tissue sample through the cutting blade may be adjusted. In one example, methods include adjusting the rate that the biological tissue sample is pressed through the cutting blades. In some instances, the rate is increased, such as by increasing the rate of displacing the tissue actuator by 1 mm/second or greater, such as 2 mm/second or greater, such as by 5 mm/sec or greater, such as by 10 mm/second or greater and by increasing the displacement rate of the tissue actuator by 25 mm/second or greater. In other instances, the rate is decreased, such as by decreasing the rate of displacing the tissue actuator by 1 mm/sec or greater, such as 2 mm/second or greater, such as by 5 mm/second or greater, such as by 10 mm/second or greater and by decreasing the displacement rate of the tissue actuator by 25 mm/second or greater. In other embodiments, methods include adjusting the configuration of one or more of the mount cutting blades and the cap cutting blades. For example, methods may include adjusting the angle of the mount cutting blades with respect to the cap cutting blades, such as to change (e.g., increase or decrease) the angle by 1° or more, such as by 3° or more, such as by 5° or more, such as by 10° or more and including by 15° or more.

In another example, the temperature while dissociating the biological tissue sample may be adjusted. For example, the temperature may be decreased, such as by 1° C. or more, such as by 2° C. or more, such as by 3° C. or more, such as by 5° C. or more, such as by 10° C. or more and including decreasing the temperature by 15° C. or more. In other embodiments, the temperature is increased by 1° C. or more, such as by 2° C. or more, such as by 3° C. or more, such as by 5° C. or more, such as by 10° C. or more and including increasing the temperature by 15° C. or more.

In some embodiments, where a single interval is not sufficient to provide the desired dissociated tissue fragments, methods may include conducting one or more additional intervals. In these embodiments, protocols described herein for dissociating a biological tissue sample into a plurality of tissue fragments are repeated one or more times in a sequential manner. In practicing the subject methods, multiple interval protocols may include two or more intervals, such as three or more intervals, such as four or more intervals, such as five or more intervals, including ten or more intervals.

Kits

Aspects of the invention further include kits, where kits include one or more sample holders, blade holders, cutting blades, tissue actuators, pliable stoppers as described herein. In some instances, the kits can include one or more additional components. In some instances, the kits may further include a biological tissue sample collection device, e.g., a lance, needle or scalpel configured to a sample of integumentary tissue, oral tissue, respiratory tissue, gastrointestinal tissue, cardiovascular tissue, endocrine tissue, genitourinary tissue, muscular tissue, nervous tissue or soft skeletal tissue, as described above. In some instances, kits of interest include components for conducting a tissue biopsy such as a tweezer, needle, scalpel or scissor. In other instances, kits include a microscope slide. In some embodiments, kits include a fluidic composition, such as a digestive enzyme composition or buffer solution. Example buffers may include but are not limited to PBS (phosphate) buffer, acetate buffer, N,N-bis(2-hydroxyethyl)glycine (Bicine) buffer, 3-{[tris(hydroxymethyl)methyl]amino}propanesulfonic acid (TAPS) buffer, 2-(N-morpholino)ethanesulfonic acid (MES) buffer, citrate buffer, tris(hydroxymethyl)methylamine (Tris) buffer, N-tris(hydroxymethyl)methylglycine (Tricine) buffer, 3-[N-Tris(hydroxymethyl)methylamino]-2-hydroxypropanesulfonic Acid (TAPSO) buffer, 4-2-hydroxyethyl-1-piperazineethanesulfonic acid (HEPES) buffer, 2-{[tris(hydroxymethyl)methyl]amino}ethanesulfonic acid (TES) buffer, piperazine-N,N'-bis(2-ethanesulfonic acid) (PIPES) buffer, dimethylarsinic acid (Cacodylate) buffer, saline sodium citrate (SSC) buffer, 2(R)-2-(methylamino)succinic acid (succinic acid) buffer, potassium phosphate buffer, N-Cyclohexyl-2-aminoethanesulfonic acid (CHES) buffer, among other types of buffered solutions. In certain instances, the fluidic composition is a cytometer-grade solution.

In still other embodiments, kits include a labelling reagent composition. For example, the labelling reagent composition may be a fluorophore, chromophore, enzyme, redox label, radiolabels, acoustic label, Raman (SERS) tag, mass tag, isotope tag, magnetic particle, microparticle or nanoparticle or a combination thereof. In some cases, the labelling reagent includes a labelled biomolecule, such as a polypeptide, a nucleic acid and a polysaccharide that is labelled with a fluorophore, chromophore, enzyme, redox label, radiolabels, acoustic label, Raman (SERS) tag, mass tag, isotope tag, magnetic particle, microparticle or nanoparticle or a combination thereof.

Kits may also include one or more containers for coupling to the subject tissue dissociators. Example containers include, but are not limited to test tubes, centrifuge tubes, culture tubes, falcon tubes, microtubes, Eppendorf tubes, specimen collection containers, specimen transport containers and petri dishes.

The various components of the kits may be present in separate containers, or some or all of them may be pre-combined. For example, in some instances, one or more components of the kit, e.g., housings, cutting blades and tissue actuators, are present in a sealed pouch, e.g., a sterile foil pouch or envelope.

In addition to the above components, the subject kits may further include (in certain embodiments) instructions for assembling the subject kit components as well as for practicing the methods for dissociating a biological tissue sample as described herein. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), portable flash drive, and the like, on which the information has been recorded. Yet another form of these instructions that may be present is a website address which may be used via the internet to access the information at a removed site.

Utility

The subject devices, methods, and kits find use in applications where tissue fragments prepared from a biological sample may be desired for research, laboratory testing or for use in therapy. The present disclosure also finds use in a variety of different applications where it is desirable to obtain biological tissue fragments having high size and shape homogeneity from a biological tissue sample. In some embodiments, the subject methods and devices may facilitate the obtaining a large amount of tissue fragments to be used as a research or diagnostic specimen for diseases such as cancer. Methods and devices of the present disclosure allow for preparing a plurality of tissue fragments from a biological tissue samples that are highly homogenous in size, shape with little waste and at a low cost.

EXPERIMENTAL

The following experimental examples are offered by way of illustration and not by way of limitation. Efforts have been made to ensure accuracy with respect to numbers used, but some experimental error and deviation should, of course, be allowed for.

Example 1

An enzyme solution is poured into a 50 ml Falcon centrifuge tube and a tissue dissociator is securely screwed onto the centrifuge tube. A tumor was dissociated into pieces and rinsed directly into an enzyme solution with no additional manual handling of the tumor. Additional handling that has been observed in some methods such as those that require mincing the tumor in a petri dish prior to introduction into the enzyme solution have a tendency to leave cells in the petri dish or experience cell loss in the transfer process resulting in fewer cells available for downstream analysis. The distal end pliable stopper forced all cut tumor pieces completely through the cutting blades. After shaking and a 30 second rinsing process is performed little to no cells remain in the tissue dissociation device. A study was conducted using a PDX mouse tumor sample (breast cancer model BRC-15, tumor ID T302) cut into six pieces with three pieces minced in three tissue dissociation devices. The minced samples were then processed thru the standard method of enzyme digestion, activity quenching and wash while the three devices were rinsed with a buffer (DPBS) and the effluent captured in a centrifuge tube. A small sample from each of the three cell suspensions as well as a small sample of the stopper effluent was read on a Beckman Coulter Vi-CELL Cell Counter. Only 1 cell was found in the stopper effluent while almost 800 cells were found in the cell suspensions.

Example 2

Studies were conducted to demonstrate that mincing a tumor into an enzyme solution with scissors and a scalpel in a petri dish produces tumor pieces that provide lower cell yield as compared to tissue cell yield from tissue dissociation devices of the present disclosure. Two different tissue dissociation studies were conducted comparing swine kidney tissue cell yield results obtained using the subject tissue dissociation devices to the cells yield results obtained by both chopping the tissue into with scissors and mincing the tissue with a scalpel. After dissociation, all tissue pieces were processed thru the standard method of enzyme digestion, activity quenching and wash described above.

Figure 13A:
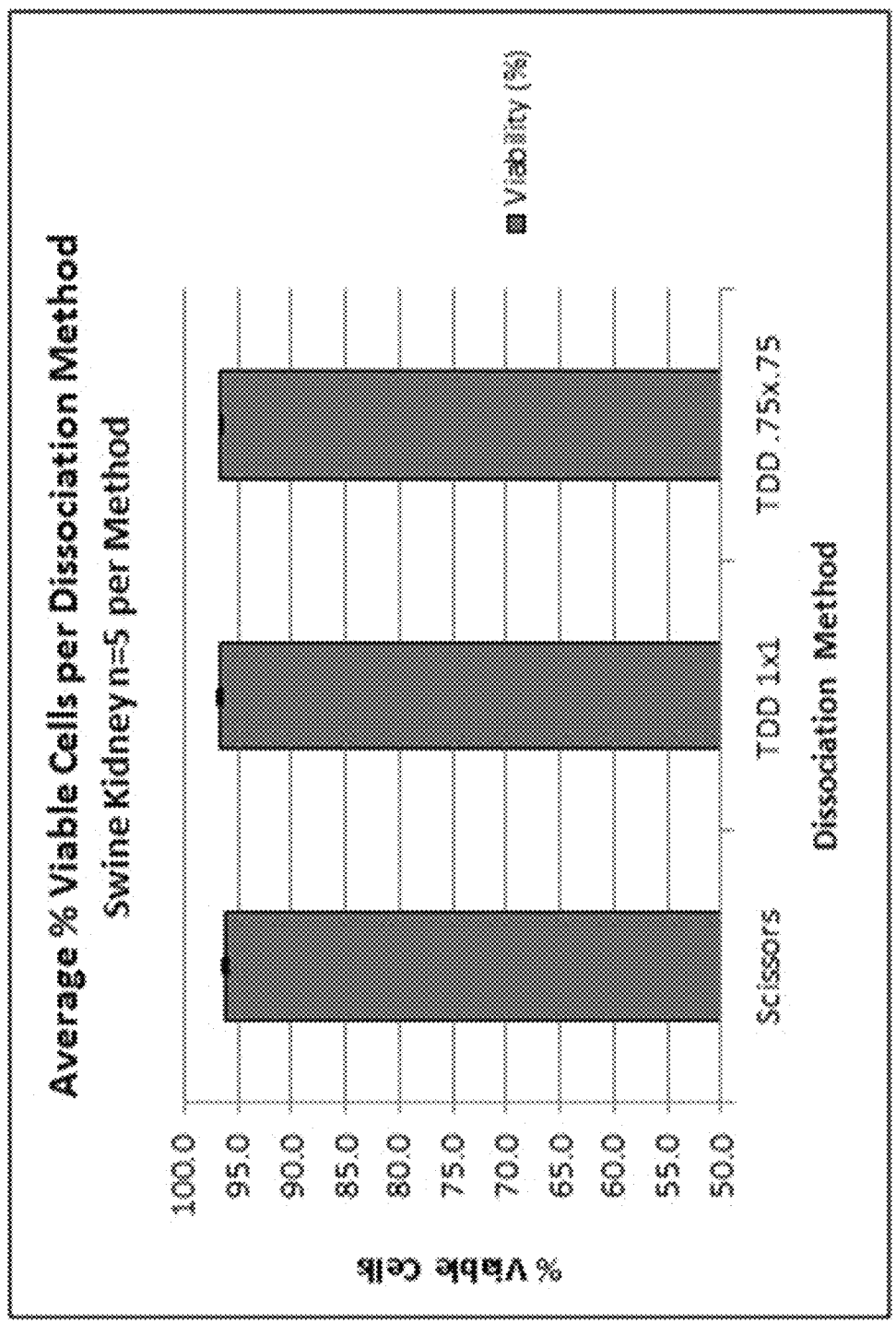
FIG. 13A depicts the cell viability of cells obtained from dissociation of swine kidney tissue manually with scissors and with tissue dissociator devices according to certain embodiments.
Figure 13B:
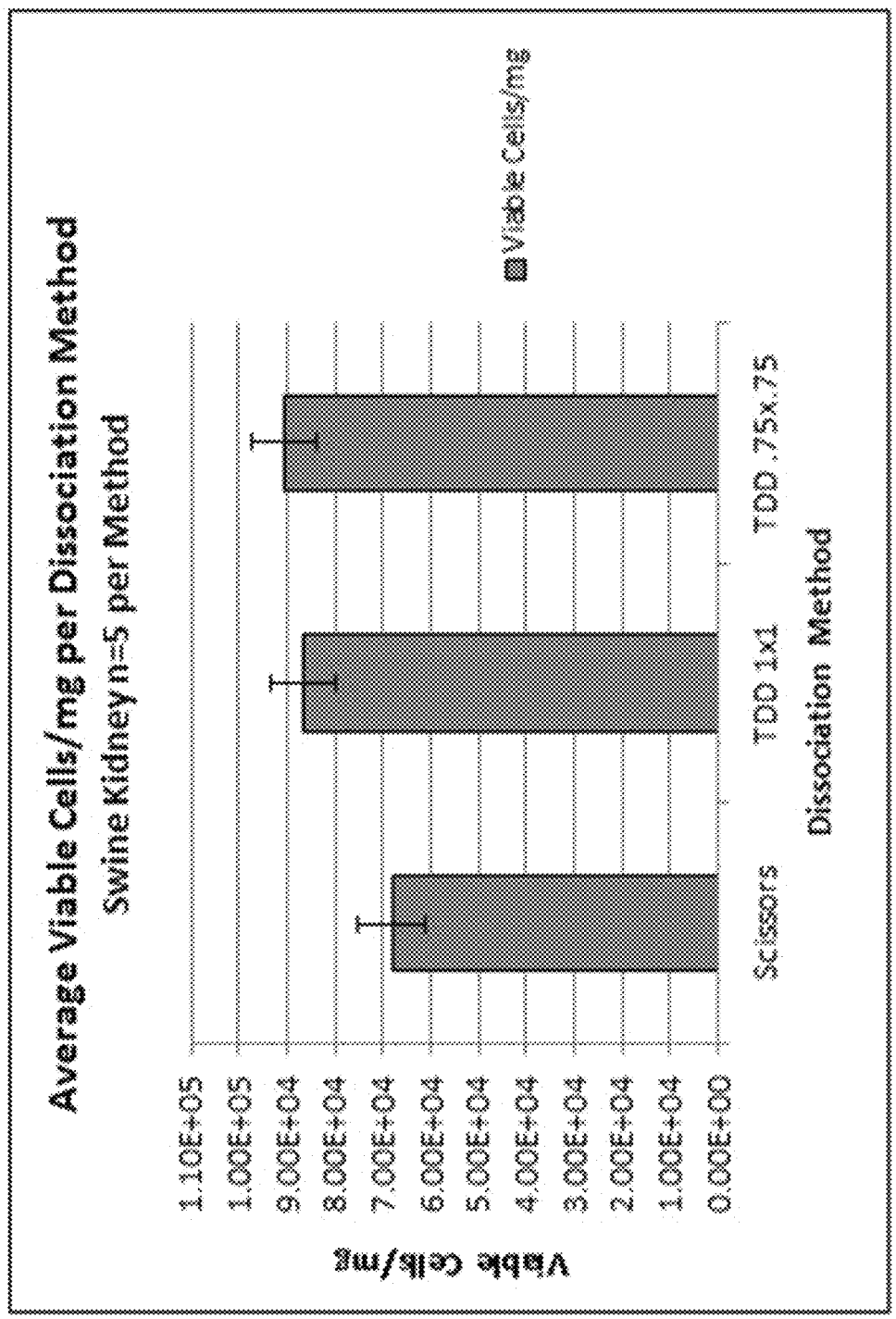
FIG. 13B depicts the yield of viable cells obtained from dissociation of swine kidney tissue manually with scissors and with tissue dissociator devices according to certain embodiments.

In the first study, cell yields from two different cutting blade arrays (0.75 mm×0.75 mm and 1 mm×1 mm) in the subject tissue dissociation devices were compared to the scissors chopping method. Cell viabilities were approximately the same for all three methods (FIG. 13A). However, cell yields obtained from the subject tissue dissociators were significantly higher than those obtained by manual dissociation with scissors (FIG. 13B). FIG. 13B also demonstrates that the subject tissue dissociators provide consistent cell yields, exhibiting cell yields that are nearly equivalent.

Figure 14A:
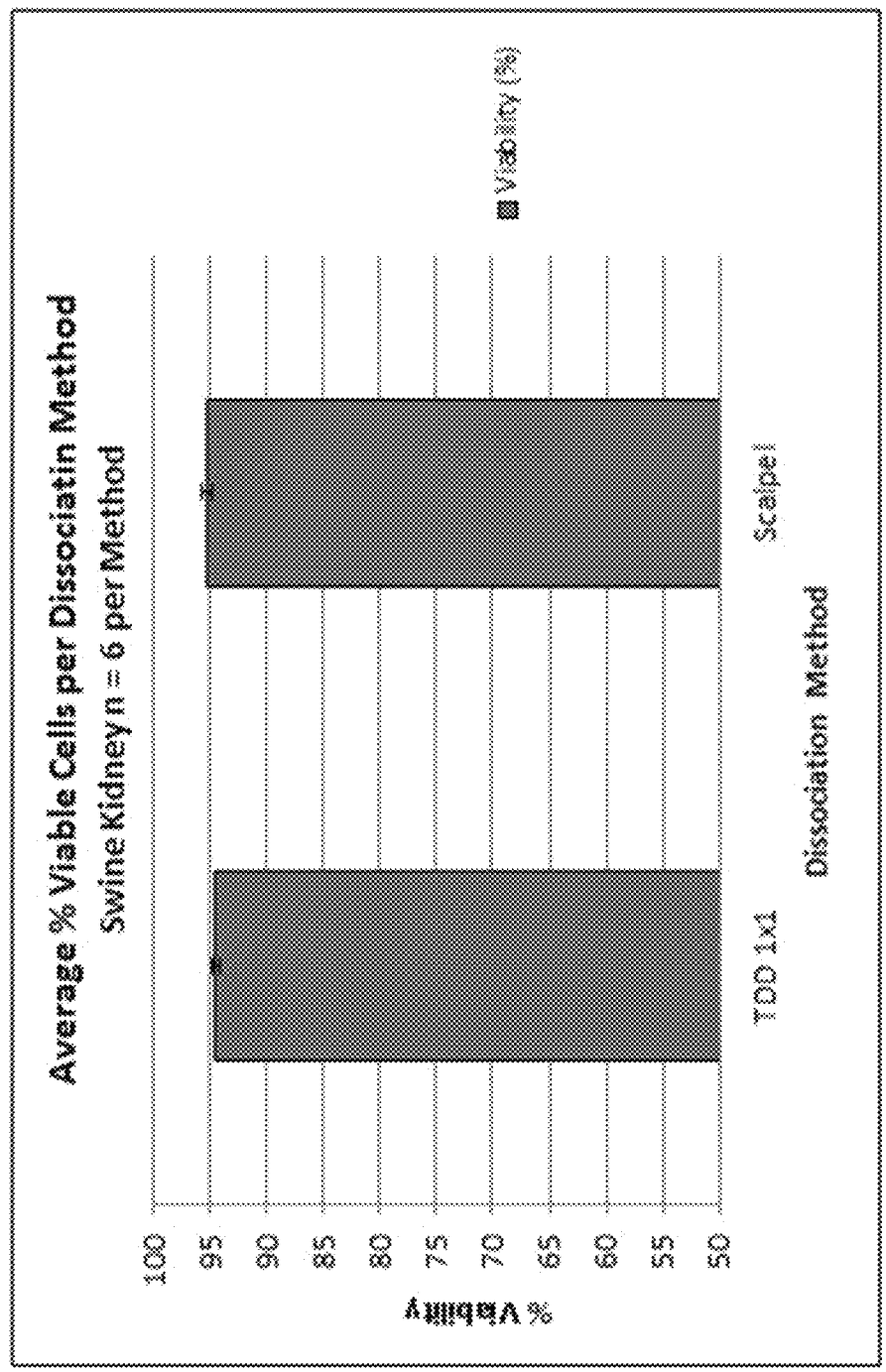
FIG. 14A depicts the cell viability of cells obtained from dissociation of swine kidney tissue manually with a scalpel and with tissue dissociator devices according to certain embodiments.
Figure 14B:
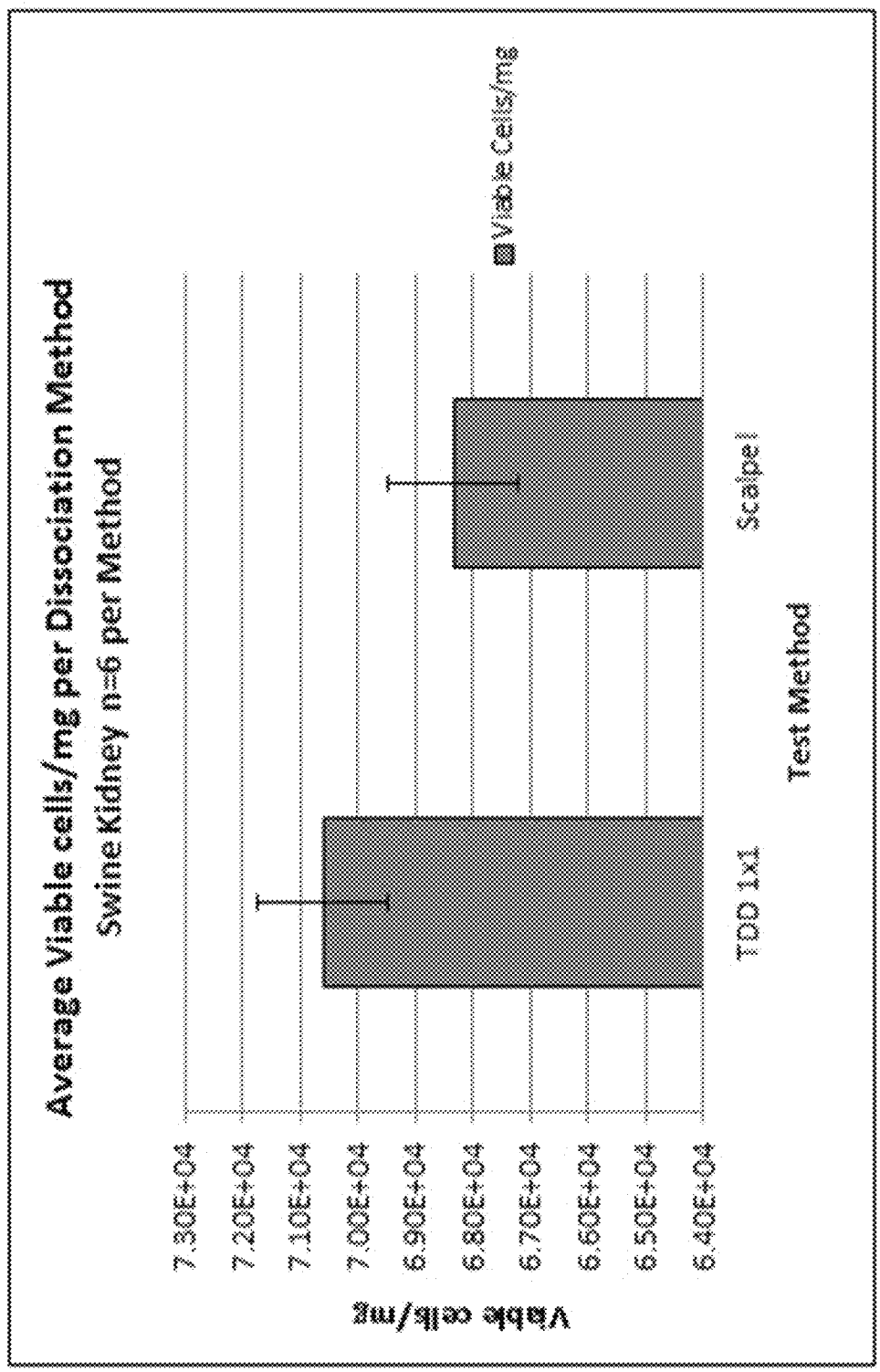
FIG. 14B depicts the yield of viable cells obtained from dissociation of swine kidney tissue manually with a scalpel and with tissue dissociator devices according to certain embodiments.

In the second study, cell yields from a tissue dissociator employing cap and mount cutting blades the form a 1 mm×1 mm array were compared to a scalpel mincing method. Cell viabilities were approximately the same for both methods (FIG. 14A). However, cell yields for the subject tissue dissociators were significantly higher than those obtained by manual dissociation with a scalpel (FIG. 14B)

Figure 15A:
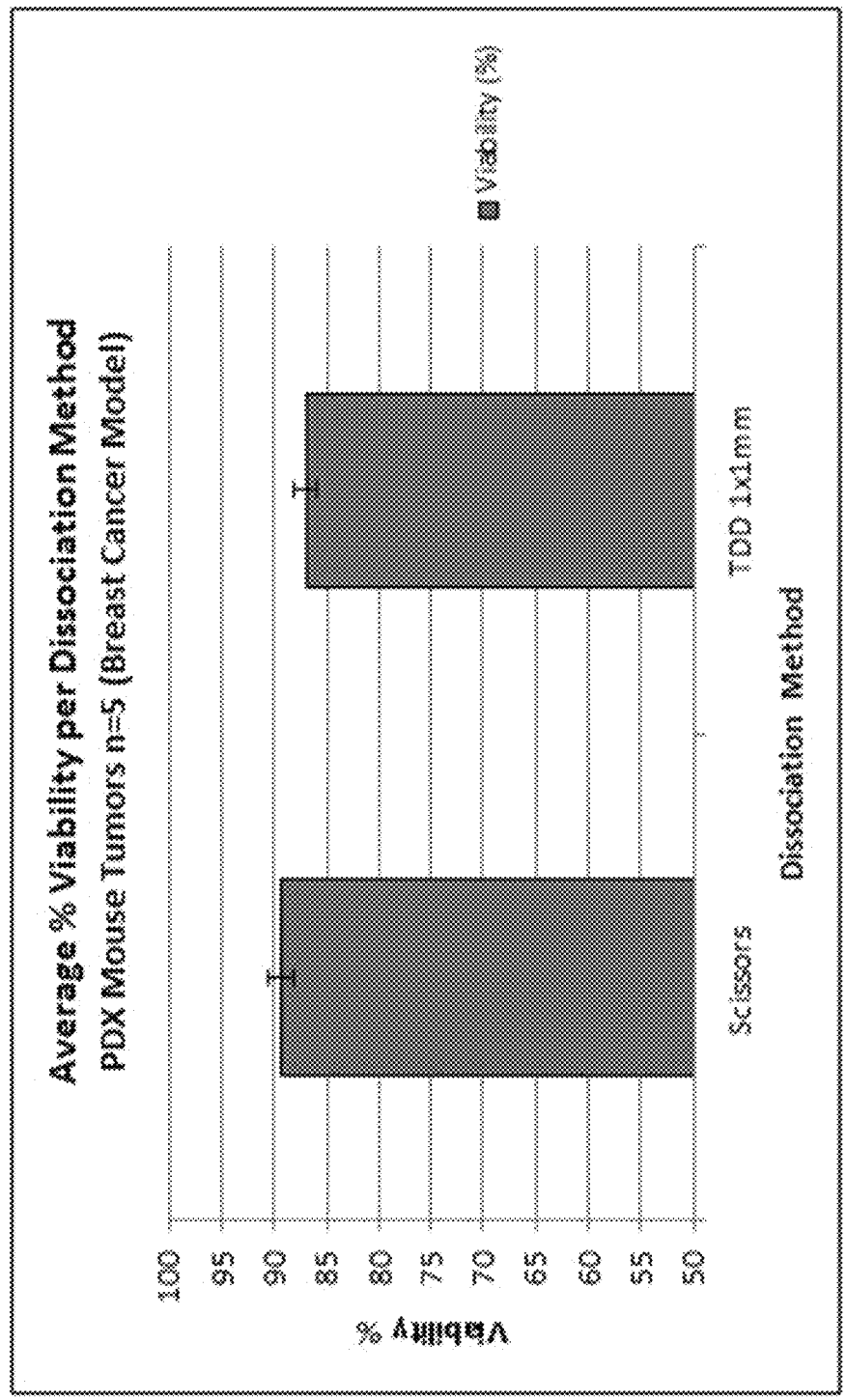
FIG. 15A depicts the cell viability of cells obtained from dissociation of PDX (Patient Derived Xenograph) mouse tumors manually with scissors and with tissue dissociator devices according to certain embodiments.
Figure 15B:
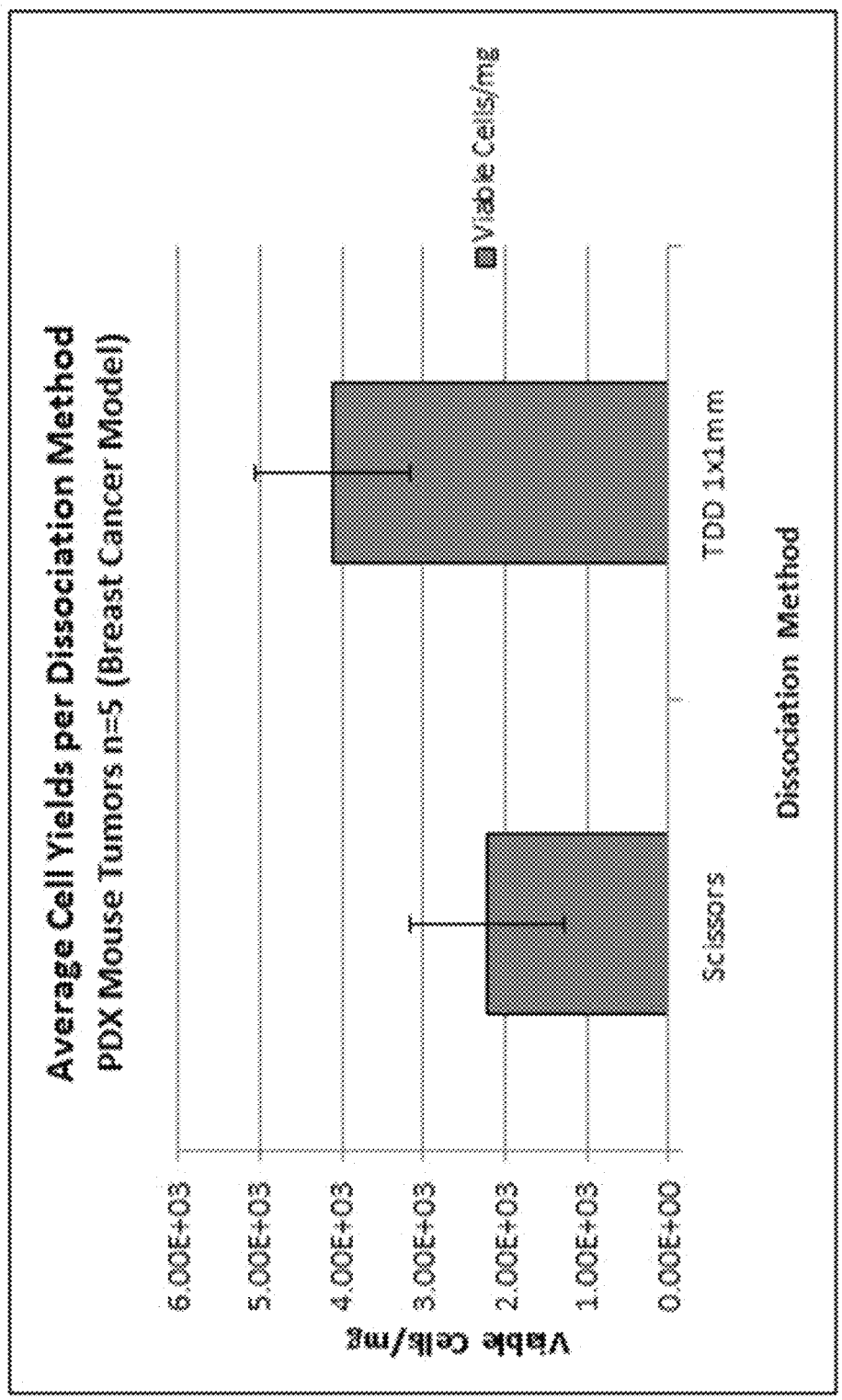
FIG. 15B depicts the yield of viable cells obtained from dissociation of PDX mouse tumors manually with scissors and with tissue dissociator devices according to certain embodiments.

In a third study, PDX mouse tumor (breast cancer model) cell yields were compared between using the subject tissue dissociation devices to the cells yield results obtained by chopping the tumor with scissors. After mincing, all tumor pieces were processed thru the standard method of enzyme quenching and wash as described above. Cell viability between the two methods (FIG. 15A) were nearly equivalent. However, cell yields for the subject tissue dissociators were significantly higher than those obtained by manual dissociation with a scissors (FIG. 15B).

Example 3

Figure 16:
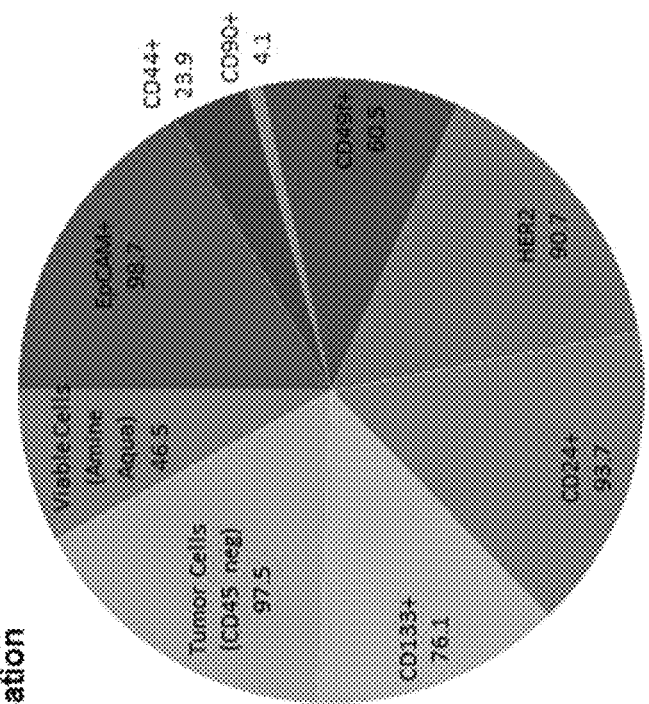
FIG. 16 depicts a comparison between the distribution of tumor cells that contain surface marker phenotypes for PDX mouse tumors dissociated manually by scissors and with tissue dissociation devices according to certain embodiments.
Figure 16:
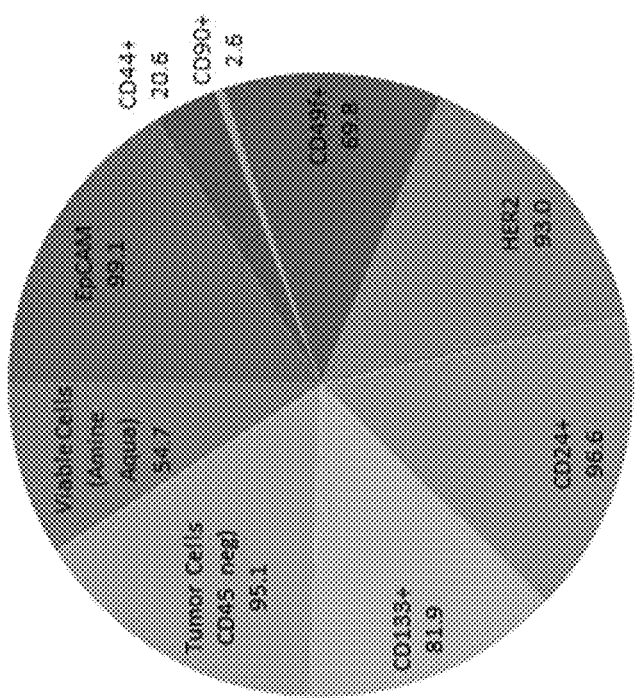
Figure 17:
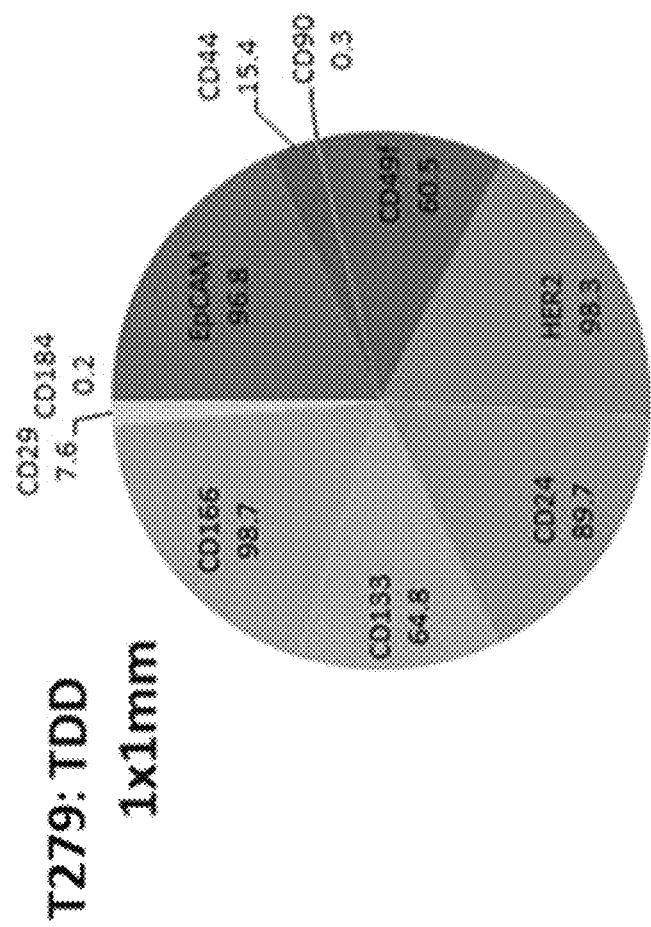
FIG. 17 depicts a comparison between the distribution of tumor cells that contain surface marker phenotypes for PDX mouse tumors dissociated manually by scissors and with tissue dissociation devices according to certain embodiments.
Figure 17:
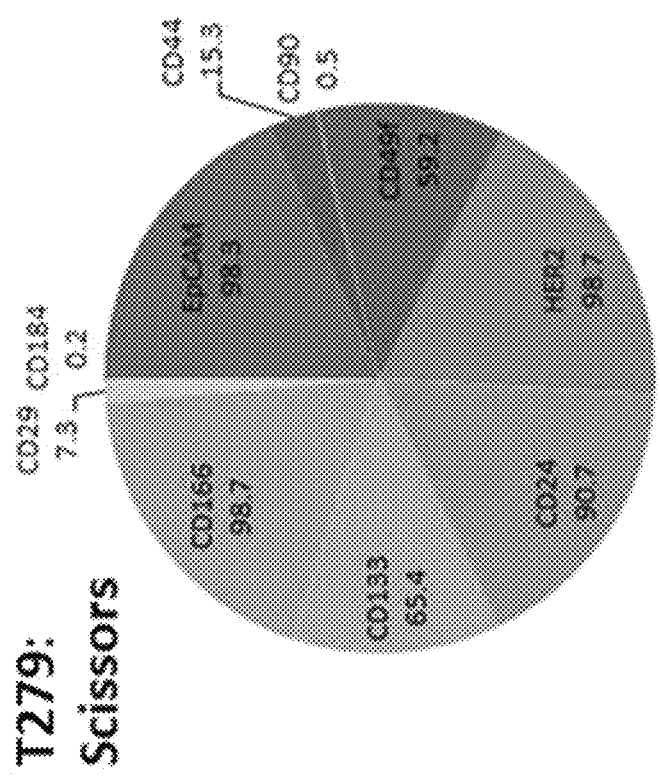
Figure 18:
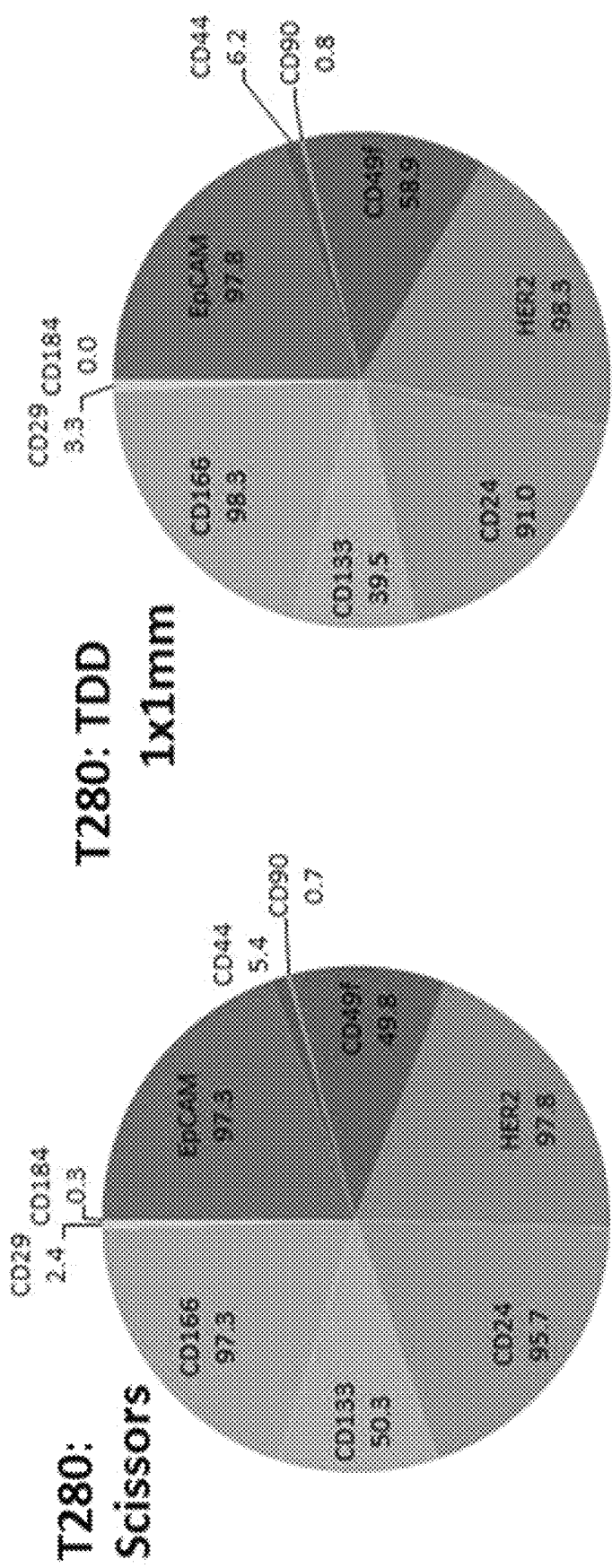
FIG. 18 depicts a comparison between the distribution of tumor cells that contain surface marker phenotypes for PDX mouse tumors dissociated manually by scissors and with tissue dissociation devices according to certain embodiments.

Studies were also conducted to demonstrate that tissue dissociation with the subject tissue dissociators preserved important cell surface markers, such as those used in cell sorting and analysis. Three PDX mouse tumors (T274, T279 and T280) were dissociated with the subject tissue dissociators as well as manually with scissors. Cells from both samples were analyzed on a BD LSRII flow cytometer to evaluate the effect of tissue dissociation on cell surface marker phenotypes. Approximately 95% to 97% percent of the cells identified as being human tumor cells within the viable cell populations were analyzed for surface marker integrity (FIGS. 16-18). The value in surface marker pie slices (CD24, CD44, etc.) is the percentage of tumor cells that contain that particular surface marker phenotype. FIG. 16 depicts a comparison between the distribution of tumor cells that contain surface marker phenotypes for T274 PDX mouse tumors dissociated manually by scissors and with the subject tissue dissociation devices. FIG. 17 depicts a comparison between the distribution of tumor cells that contain surface marker phenotypes for T279 PDX mouse tumors dissociated manually by scissors and with the subject tissue dissociation devices. FIG. 18 depicts a comparison between the distribution of tumor cells that contain surface marker phenotypes for T280 PDX mouse tumors dissociated manually by scissors and with the subject tissue dissociation devices. The surface marker results in all three tumor types exhibited no adverse effects on cell surface marker integrity. Notwithstanding the appended clauses, the disclosure set forth herein is also defined by the following clauses:

1. A tissue dissociator comprising:
   a blade holder comprising a blade; and
   a sample holder comprising a tissue actuator having a distal end pliable stopper, the tissue actuator being configured to be displaced along a longitudinal axis within the sample holder.

2. The tissue dissociator according to clause 1, wherein the pliable stopper comprises polydimethylsiloxane.

3. The tissue dissociator according to any one of clauses 1-2, wherein the pliable stopper has a compressive strength of from 10 N to 100 N.

4. The tissue dissociator according to any one of clauses 1-3, wherein the pliable stopper is configured to be cut by at least one of the blades of the blade holder when the tissue actuator is displaced to the distal end of the sample holder.

5. The tissue dissociator according to any one of clauses 1-4, wherein the blade holder comprises:
   a mount comprising a first cutting blade; and
   a cap comprising a second cutting blade.

6. The tissue dissociator according to clause 5, wherein the pliable stopper is configured to be cut by the second cutting blade when the tissue actuator is displaced to the distal end of the sample holder.

7. The tissue dissociator according to clause 5, wherein the pliable stopper is configured to be cut by the first cutting blade and the second cutting blade when the tissue actuator is displaced to the distal end of the sample holder.

8. The tissue dissociator according to clause 5, wherein the mount is configured to be coupled to the cap.

9. The tissue dissociator according to clause 8, wherein the mount comprises one or more aligners that are configured for coupling to one or more aligners on the cap.

10. The tissue dissociator according to clause 9, wherein the aligners are configured to position the mount cutting blade at an angle of from 1° to 90° with respect to the cap cutting blade.

11. The tissue dissociator according to clause 9, wherein the aligners are configured to position the mount cutting blade to be orthogonal with respect to the cap cutting blade.

12. The tissue dissociator according to any one of clauses 5-11, wherein the mount comprises an orifice and the first cutting blade extends across the mount orifice.

13. The tissue dissociator according to clause 12, wherein the first cutting blade extends across the center of the mount orifice.

14. The tissue dissociator according to clause 12, wherein the first cutting blade is coupled to the mount with one or more fasteners.

15. The tissue dissociator according to clause 12, wherein the first cutting blade is co-molded with the mount.

16. The tissue dissociator according to any one of clauses 5-15, wherein the mount comprises two or more parallel cutting blades.

17. The tissue dissociator according to clause 16, wherein the mount cutting blades are equidistantly spaced.

18. The tissue dissociator according to clause 17, wherein the mount cutting blades are spaced apart from each other by 0.5 mm to 10 mm.

19. The tissue dissociator according to clause 16, wherein the mount cutting blades are spaced apart from each other by 1 mm.

20. The tissue dissociator according to any one of clauses 5-19, wherein the cap comprises an orifice and the second cutting blade extends across the cap orifice.

21. The tissue dissociator according to clause 20, wherein the cap orifice is the same size as the mount orifice.

22. The tissue dissociator according to clause 20, wherein the second cutting blade extends across the center of the cap orifice.

23. The tissue dissociator according to clause 22, wherein the second cutting blade is coupled to the cap with one or more fasteners.

24. The tissue dissociator according to clause 22, wherein the second cutting blade is co-molded with the cap.

25. The tissue dissociator according to any one of clauses 5-24, wherein the cap comprises two or more parallel cutting blades.

26. The tissue dissociator according to clause 25, wherein the cap cutting blades are equidistantly spaced.

27. The tissue dissociator according to clause 26, wherein the cap cutting blades are spaced apart from each other by 1 mm.

28. The tissue dissociator according to any one of clauses 5-27, wherein the mount cutting blades are positioned at an angle of from 1° to 90° with respect to the cap cutting blades.

29. The tissue dissociator according to clause 28, wherein the mount cutting blades are positioned orthogonally with respect to the cap cutting blades.

30. The tissue dissociator according to any one of clauses 5-29, wherein the sample holder is coupled to the cap.

31. The tissue dissociator according to clause 30, wherein the sample holder is an integrated part of the cap.

32. The tissue dissociator according to any one of clauses 5-31, wherein the sample holder comprises a proximal end and a distal end and wherein the sample holder is coupled to the cap and the second cutting blade is positioned at the distal end of the sample holder.

33. The tissue dissociator according to any one of clauses 1-32, wherein the sample holder has a volume of 0.25 cm$^3$ or more.

34. The tissue dissociator according to any one of clauses 1-33, wherein the blade holder is configured to be releasably coupled to a container.

35. The tissue dissociator according to clause 34, wherein the blade holder comprises threaded walls configured to be screw threaded with a container.

36. The tissue dissociator according to clause 34, wherein the container is selected from the group consisting of a blood collection tube, test tube, centrifuge tube, culture tube, microtube, Eppendorf tube and syringe.

37. A tissue dissociator comprising:
a container;
a blade holder releasably coupled to the container, the blade holder comprising a blade; and
a sample holder comprising a tissue actuator having a distal end pliable stopper, the tissue actuator being configured to be displaced along a longitudinal axis within the sample holder.

38. The tissue dissociator according to clause 37, wherein the pliable stopper comprises polydimethylsiloxane.

39. The tissue dissociator according to any one of clauses 37-38, wherein the pliable stopper has a compressive strength of from 10 N to 100 N.

40. The tissue dissociator according to any one of clauses 37-39, wherein the pliable stopper is configured to be cut by at least one of the blades of the blade holder when the tissue actuator is displaced within the sample holder.

41. The tissue dissociator according to any one of clauses 37-40, wherein the blade holder comprises:
a mount comprising a first cutting blade; and
a cap comprising a second cutting blade.

42. The tissue dissociator according to clause 41, wherein the pliable stopper is configured to be cut by the second cutting blade when the tissue actuator is displaced within the sample holder.

43. The tissue dissociator according to clause 41, wherein the pliable stopper is configured to be cut by the first cutting blade and the second cutting blade when the tissue actuator is displaced within the sample holder.

44. The tissue dissociator according to any one of clauses 37-43, wherein the container is selected from the group consisting of a blood collection tube, test tube, centrifuge tube, culture tube, microtube, Eppendorf tube and syringe.

45. The tissue dissociator according to any one of clauses 37-44, wherein the container is screw-threaded to the blade holder.

46. A method of dissociating biological tissue, the method comprising:
positioning a biological tissue into a sample holder of a tissue dissociator, wherein the tissue dissociator comprises:
a blade holder comprising a blade; and
a sample holder comprising a tissue actuator having a distal end pliable stopper, the tissue actuator being configured to be displaced along a longitudinal axis within the sample holder;

pressing the biological tissue against the cutting blades by displacing the tissue actuator from the proximal end of the sample holder to the distal end of the sample holder in a manner sufficient dissociate the biological tissue and cut the pliable stopper with at least one of the cutting blades.

47. The method according to clause 46, wherein the pliable stopper comprises polydimethylsiloxane.

48. The method according to any one of clauses 46-47, wherein the pliable stopper has a compressive strength of from 10 N to 100 N.

49. The method according to clause 46, wherein the pliable stopper contacts the outer walls of the blade when the tissue actuator is displaced to the distal end of the sample holder.

50. The method according to clause 49, wherein the pliable stopper is configured to force the biological tissue completely through the blades when the tissue actuator is displaced to the distal end of the sample holder.

51. The method according to clause 49, wherein the pliable stopper is configured such that no biological tissue remains in contact with the blades when the tissue actuator is displaced to the distal end of the sample holder.

52. The method according to any one of clauses 46-51, wherein the tissue actuator is displaced in discrete increments.

53. The method according to any one of clauses 46-52, wherein the tissue actuator is displaced continuously.

54. The method according to any one of clauses 46-53, wherein the tissue actuator is displaced in a back and forth motion.

55. The method according to clause 54, wherein the back and forth motion is sufficient to remove biological tissue from the blades with the pliable stopper.

56. The method according to any one of clauses 46-55, wherein the blade holder is configured to be releasably attached to a container.

57. The method according to clause 56, wherein the method further comprises coupling the blade holder to the container.

58. The method according to clause 57, wherein the container comprises a fluid.

59. The method according to clause 58, wherein the fluid is buffer.

60. The method according to any one of clauses 46-59, wherein the method further comprises shaking the container to release dissociated tissue from the cutting blades.

61. The method according to any one of clauses 46-60, wherein the blade holder comprises:
 a mount comprising a first cutting blade; and
 a cap comprising a second cutting blade.

62. The method according to clause 61, wherein the pliable stopper is configured to be cut by the second cutting blade when the tissue actuator is displaced to the distal end of the sample holder.

63. The method according to clause 61, wherein the pliable stopper is configured to be cut by the first cutting blade and the second cutting blade when the tissue actuator is displaced to the distal end of the sample holder.

64. The method according to clause 61, wherein the mount is configured to be coupled to be coupled to the cap.

65. The method according to clause 64, wherein the mount comprises one or more aligners that are configured for coupling to one or more aligners on the cap.

66. The method according to clause 65, wherein the aligners are configured to position the mount cutting blade at an angle of from 1° to 90° with respect to the cap cutting blade.

67. The method according to clause 66, wherein the aligners are configured to position the mount cutting blade to be orthogonal with respect to the cap cutting blade.

68. The method according to any one of clauses 61-67, wherein the mount comprises an orifice and the first cutting blade extends across the mount orifice.

69. The method according to clause 68, wherein the first cutting blade extends across the center of the mount orifice.

70. The method according to clause 69, wherein the first cutting blade is coupled to the mount with one or more fasteners.

71. The method according to clause 69, wherein the first cutting blade is co-molded with the mount.

72. The method according to any one of clauses 61-68, wherein the mount comprises two or more parallel cutting blades.

73. The method according to clause 72, wherein the mount cutting blades are equidistantly spaced.

74. The method according to clause 73, wherein the mount cutting blades are spaced apart from each other by 0.5 mm to 10 mm.

75. The method according to clause 73, wherein the mount cutting blades are spaced apart from each other by 1 mm.

76. The method according to any one of clauses 61-75, wherein the cap comprises an orifice and the second cutting blade extends across the cap orifice.

77. The method according to clause 76, wherein the cap orifice is the same size as the mount orifice.

78. The method according to clause 76, wherein the second cutting blade extends across the center of the cap orifice.

79. The method according to any one of clauses 61-78, wherein the second cutting blade is coupled to the cap with one or more fasteners.

80. The method according to any one of clauses 61-78, wherein the second cutting blade is co-molded with the cap.

81. The method according to any one of clauses 61-78, wherein the cap comprises two or more parallel cutting blades.

82. The method according to clause 81, wherein the cap cutting blades are equidistantly spaced.

83. The method according to clause 82, wherein the cap cutting blades are spaced apart from each other by 1 mm.

84. The method according to any one of clauses 61-83, wherein the mount cutting blades are positioned at an angle of from 1° to 90° with respect to the cap cutting blades.

85. The method according to clause 84, wherein the mount cutting blades are positioned orthogonally with respect to the cap cutting blades.

86. The method according to any one of clauses 61-85, wherein the sample holder is coupled to the cap.

87. The method according to clause 86, wherein the sample holder is an integrated part of the cap.

88. The method according to any one of clauses 61-87, wherein the sample holder comprises a proximal end and a distal end and wherein the sample holder is coupled to the cap and the second cutting blade is positioned at the distal end of the sample holder.

89. The method according to any one of clauses 46-88, wherein the sample holder has a volume of 0.25 $cm^3$ or more.

90. A kit comprising:
a sample holder comprising a tissue actuator configured to be displaced along a longitudinal axis within the sample holder; and
a pliable stopper for positioning at the distal end of the tissue actuator.

91. The kit according to clause 90, further comprising a blade holder comprising two or more cutting blades positioned at an angle with respect to each other.

92. The kit according to clause 90, wherein the pliable stopper comprises polydimethylsiloxane.

93. The kit according to any one of clauses 90-92, wherein the pliable stopper has a compressive strength of from 10 N to 100 N.

94. The kit according to any one of clauses 90-93, wherein the pliable stopper is configured to be cut by at least one of the blades of the blade holder when the tissue actuator is displaced within the sample holder.

95. The kit according to any one of clauses 91-94, wherein the sample holder is coupled to the blade holder.

96. The kit according to any one of clauses 91-95, wherein the blade holder comprises:
a mount component comprising a first cutting blade; and
a cap component comprising a second cutting blade.

97. The kit according to clause 96, wherein the pliable stopper is configured to be cut by the second cutting blade when the tissue actuator is displaced to the distal end of the sample holder.

98. The kit according to clause 96, wherein the pliable stopper is configured to be cut by the first cutting blade and the second cutting blade when the tissue actuator is displaced to the distal end of the sample holder.

99. The kit according to any one of clauses 96-98, wherein the mount is configured to couple to the cap and position the mount cutting blade at an angle of from 1° to 90° with respect to the cap cutting blade.

100. The kit according to any one of clauses 96-99, wherein the kit comprises two or more mount cutting blades.

101. The kit according to any one of clauses 96-99, wherein the kit comprises two or more cap cutting blades.

102. The kit according to any one of clauses 90-101, further comprising a tissue biopsy utensil selected from the group consisting of a tweezer, needle, scalpel and scissor.

103. The kit according to clause 102, wherein the kit comprises a needle and syringe.

104. The kit according to any one of clauses 90-103, further comprising one or more of tissue preservative and tissue stain.

105. The kit according to any one of clauses 90-104, further comprises a microscope slide.

106. The kit according to any one of clauses 90-105, further comprising a digestive enzyme composition.

107. The kit according to any one of clauses 90-106, further comprising a buffer solution.

108. The kit according to clause 107, wherein the buffer solution is a cytometer-grade buffer solution.

109. The kit according to any one of clauses 90-108, further comprising a labelling reagent.

110. The kit according to clause 109, wherein the labelling reagent comprises a compound selected from the group consisting of fluorophore, chromophore, enzyme, redox label, radiolabels, acoustic label, Raman (SERS) tag, mass tag, isotope tag, magnetic particle, microparticle and nanoparticle.

111. The kit according to clause 109, wherein the labelling reagent comprises a labelled biomolecule.

112. The kit according to clause 111, wherein the labelled biomolecule is a compound selected from the group consisting of a polypeptide, a nucleic acid and a polysaccharide that is labelled with a compound selected from the group consisting of a fluorophore, chromophore, enzyme, redox label, radiolabels, acoustic label, Raman (SERS) tag, mass tag, isotope tag, magnetic particle, microparticle and nanoparticle.

113. The kit according to any one of clauses 90-112, further comprising a container configured to be coupled to the blade holder.

114. The kit according to clause 113, wherein the container is selected from the group consisting of a blood collection tube, test tube, centrifuge tube, culture tube, microtube, Eppendorf tube and syringe.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A tissue dissociator comprising:
a blade holder comprising one or more blades; and
a sample holder comprising a tissue actuator having a distal end pliable stopper, wherein
the tissue actuator is configured to be displaced along a longitudinal axis within the sample holder; and
the pliable stopper is configured to be cut by at least one of the blades of the blade holder when the tissue actuator is displaced to the distal end of the sample holder.

2. The tissue dissociator according to claim 1, wherein the blade holder comprises:
a mount comprising a first cutting blade; and
a cap comprising a second cutting blade.

3. The tissue dissociator according to claim 2, wherein the pliable stopper is configured to be cut by the first cutting blade and the second cutting blade when the tissue actuator is displaced to the distal end of the sample holder.

4. The tissue dissociator according to claim 2, wherein the mount is configured to be coupled to the cap.

5. The tissue dissociator according to claim 4, wherein the mount comprises one or more aligners that are configured for coupling to one or more aligners on the cap.

6. The tissue dissociator according to claim 5, wherein the aligners are configured to position the mount cutting blade at an angle of from 1° to 90° with respect to the cap cutting blade.

7. The tissue dissociator according to claim 5, wherein the aligners are configured to position the mount cutting blade to be orthogonal with respect to the cap cutting blade.

8. The tissue dissociator according to claim 2, wherein the mount comprises an orifice and the first cutting blade extends across the mount orifice.

9. The tissue dissociator according to claim 2, wherein the cap comprises an orifice and the second cutting blade extends across the cap orifice.

10. The tissue dissociator according to claim 2, wherein the cap comprises two or more parallel cutting blades.

11. The tissue dissociator according to claim 1, wherein the mount comprises two or more parallel cutting blades.

12. The tissue dissociator according to claim 1, wherein the blade holder is releasably coupled to a container.

13. A method of dissociating biological tissue, the method comprising:
    positioning a biological tissue into a sample holder of a tissue dissociator, wherein the tissue dissociator comprises:
        a blade holder comprising a blade; and
        a sample holder comprising a tissue actuator having a distal end pliable stopper, the tissue actuator being configured to be displaced along a longitudinal axis within the sample holder;
    pressing the biological tissue against the cutting blades by displacing the tissue actuator from the proximal end of the sample holder to the distal end of the sample holder in a manner sufficient dissociate the biological tissue and cut the pliable stopper with at least one of the cutting blades.

14. A kit comprising:
    a blade holder comprising two or more cutting blades positioned at an angle with respect to each other;
    a sample holder comprising a tissue actuator configured to be displaced along a longitudinal axis within the sample holder; and
    a pliable stopper for positioning at the distal end of the tissue actuator,
    wherein the pliable stopper is configured to be cut by at least one of the blades of the blade holder when the tissue actuator is displaced to the distal end of the sample holder.

15. The kit according to claim 14, wherein the blade holder comprises:
    a mount component comprising a first cutting blade; and
    a cap component comprising a second cutting blade.

16. The kit according to claim 14, further comprising a tissue biopsy utensil selected from the group consisting of a tweezer, needle, scalpel and scissor.

17. The kit according to claim 14, further comprising one or more of tissue preservative and tissue stain.

18. The kit according to claim 14, further comprising a digestive enzyme composition.

19. The kit according to claim 14, further comprising a container configured to be coupled to the blade holder.

* * * * *